(12) United States Patent
Allen et al.

(10) Patent No.: US 8,153,372 B2
(45) Date of Patent: Apr. 10, 2012

(54) METHOD FOR SIMULTANEOUSLY DETERMINING IN A SINGLE MULTIPLEX REACTION GENDER OF DONORS AND QUANTITIES OF GENOMIC DNA AND RATIOS THEREOF, PRESENCE AND EXTENT OF DNA DEGRADATION, AND PCR INHIBITION WITHIN A HUMAN DNA SAMPLE

(75) Inventors: Robert W. Allen, Tulsa, OK (US); Valerie Fuller, Tulsa, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 345 days.

(21) Appl. No.: 11/960,113

(22) Filed: Dec. 19, 2007

(65) Prior Publication Data

US 2008/0153099 A1 Jun. 26, 2008

Related U.S. Application Data

(60) Provisional application No. 60/870,770, filed on Dec. 19, 2006.

(51) Int. Cl.
*C12Q 1/68* (2006.01)
*C12P 19/34* (2006.01)

(52) U.S. Cl. ...................... 435/6.12; 435/91.2
(58) Field of Classification Search .............. 435/6, 91.2
See application file for complete search history.

(56) References Cited

U.S. PATENT DOCUMENTS

| | | | | | |
|---|---|---|---|---|---|
| 5,582,989 | A | * | 12/1996 | Caskey et al. ................ | 435/6 |
| 6,001,572 | A | * | 12/1999 | Toothman ................... | 435/6 |
| 6,479,235 | B1 | * | 11/2002 | Schumm et al. .............. | 435/6 |
| 7,067,249 | B2 | * | 6/2006 | Kung et al. .................. | 435/5 |
| 2006/0099620 | A1 | | 5/2006 | Walker et al. | |
| 2007/0048755 | A1 | * | 3/2007 | Di Fiore ..................... | 435/6 |
| 2007/0231803 | A1 | * | 10/2007 | Jensen ....................... | 435/6 |

OTHER PUBLICATIONS

Santos et al., Nature Genetics 18, 103 (1998).*
Steiper et al., Anthrop. Anz. 61, 1-5 (2003).*
Andreasson, et al. , "Real-Time DNA Quantification of Nuclear and Mitochondrial DNA in Forensic Analysis", "BioTechniques", Aug. 2002, pp. 402-411, vol. 33, No. 2, Publisher: Uppsala University, Published in: SE.
Fox, et al. , "Development, Characterization, and Validation of a Sensitive Primate-Specific Quantification Assay for Forensic Analysis", "BioTechniques", Feb. 2003, pp. 314-322, vol. 34, No. 2, Publisher: The Bode Technology Group, Published in: US.
Horsman, et al. , "Development of a Human-Specific Real-Time PCR Assay for the Simultaneous Quantitation of Total Genomic and Male DNA", "J Forensic Sci.", Jul. 2006, pp. 758-765, vol. 51, No. 4, Publisher: American Academy of Forensic Sciences, Published in: US.
Nicklas, et al. , "Development of an Alu-Based, QSY 7-Labeled Primer PCR Method for Quantitation of Human DNA in Forensic Samples", "J Forensic Sci.", Mar. 2003, pp. 1-10, vol. 48, No. 2, Publisher: ASTM International, Published in: US.
Nicklas, et al. , "Development of an Alu-based, Real-Time PCR Method for Quantitation of Human DNA in Forensic Samples", "J Forensic Sci.", Sep. 2003, pp. 1-9, vol. 48, No. 5, Publisher: ASTM International, Published in: US.
Richard, et al. , "Developmental Validation of a Real-Time Quantitative PCR Assay for Automated Quantification of Human DNA", "J Forensic Sci", Aug. 4, 2003, pp. 1041-1046, vol. 48, No. 5, Publisher: ASTM International, Published in: US.
Sifis, et al. , "A More Sensitive Method for the Quantitation of Genomic DNA by Alu Amplification", "J Forensic Sci", May 1, 2002, pp. 589-592, vol. 47, No. 3, Publisher: ASTM International , Published in: US.
Allen, et al. , "Quantitation of Human Genomic DNA Through Amplification of the Amelogenin Locus", "J Forensic Sci.", Dec. 26, 2005, pp. 76-81, vol. 51, No. 1, Publisher: American Academy of Forensic Sciences, Published in: US.

* cited by examiner

*Primary Examiner* — Kenneth R. Horlick
(74) *Attorney, Agent, or Firm* — Fellers, Snider, Blankenship, Bailey & Tippens, P.C.

(57) ABSTRACT

Methods are provided for determining, in a single polymerase chain reaction (PCR) reaction, the quantity, quality, and gender of origin of DNA in a sample, and whether or not the sample contains PCR amplification inhibitors. The methods involve carrying out a single PCR multiplex reaction utilizing primer sets specific for amplifying the human amelogenin locus, an X- and/or Y-chromosome specific gene that is shorter than the amelogenin gene, and a heterologous, non-human reporter gene.

18 Claims, 27 Drawing Sheets

Figure 14

Mock Female

| Sample | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | μ | σ | CV |
|---|---|---|---|---|---|---|---|---|---|---|---|---|---|---|---|---|---|---|---|---|---|---|---|---|---|---|
| Mock Female RFU (diluted 1/4) | 5250 | 7383 | 7294 | 7146 | 7267 | 7392 | 7703 | 7454 | 7554 | 6572 | 7607 | 7682 | 6243 | 4943 | 7717 | | | | | | | | | 7014 | 882 | 12.57% |
| IMA (X) total human est. pg of DNA | 353 | 490 | 405 | 475 | 483 | 491 | 511 | 495 | 501 | 438 | 505 | 510 | 417 | 334 | 512 | | | | | | | | | 467 | 57 | 12.14% |
| Mock Female RFU (diluted 1/8) | 4640 | 3645 | 3331 | 4315 | 5227 | 3872 | 3529 | 4919 | 5478 | 4216 | 5222 | 5835 | 5806 | 5250 | 6743 | 4641 | 7324 | 7731 | 2851 | 4404 | 4707 | 4200 | 5176 | 4916 | 1217 | 24.77% |
| IMA (X) total human est. pg of DNA | 314 | 250 | 230 | 293 | 352 | 265 | 243 | 332 | 368 | 287 | 352 | 391 | 389 | 353 | 449 | 314 | 487 | 513 | 199 | 299 | 319 | 286 | 349 | 332 | 78 | 23.59% |
| Mock Female RFU (diluted 1/16) | 1374 | 1529 | 2016 | 2557 | 2019 | 2576 | 3389 | 2996 | 2271 | 2819 | 1830 | 1338 | 1446 | 1879 | 1942 | | | | | | | | | 2132 | 624 | 29.27% |
| IMA (X) total human est. pg of DNA | 105 | 115 | 146 | 181 | 146 | 182 | 234 | 209 | 162 | 197 | 134 | 102 | 109 | 137 | 141 | | | | | | | | | 153 | 40 | 26.13% |
| Mock Female RFU (diluted 1/32) | 341 | 899 | 805 | 1262 | 889 | 836 | 820 | 812 | 970 | 647 | 1252 | 808 | 796 | 1376 | 1016 | | | | | | | | | 902 | 257 | 28.46% |
| IMA (X) total human est. pg of DNA | 38 | 74 | 68 | 97 | 73 | 70 | 69 | 69 | 79 | 58 | 97 | 68 | 63 | 105 | 82 | | | | | | | | | 74 | 17 | 22.26% |

Average σ of Total Human RFU: 745, 23.77%
Average σ of Total Human DNA (pg): 48, 21.03%

Mock Male — Total Human

| Sample | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | μ | σ | CV |
|---|---|---|---|---|---|---|---|---|---|---|---|---|---|---|---|---|---|---|---|---|---|---|---|---|---|---|
| Mock Male RFU (diluted 1/2) | 13213 | 13226 | 12071 | 14182 | 11796 | 10982 | 9984 | 12057 | 13282 | 8794 | | | | | | | | | | | | | | 11959 | 1660 | 13.88% |
| IMA (X) total human est. pg of DNA | 865 | 855 | 791 | 927 | 774 | 721 | 657 | 790 | 869 | 581 | | | | | | | | | | | | | | 784 | 107 | 13.60% |
| Mock Male RFU (diluted 1/4) | 3871 | 3749 | 3578 | 3780 | 3626 | 3642 | 3849 | 4020 | 3942 | 4036 | 4708 | 6101 | 8267 | 5659 | 6058 | 6914 | 5164 | 5346 | | | | | | 4795 | 1350 | 28.16% |
| IMA (X) total human est. pg of DNA | 265 | 257 | 246 | 259 | 249 | 250 | 263 | 274 | 269 | 276 | 319 | 408 | 547 | 380 | 405 | 460 | 341 | 367 | | | | | | 324 | 87 | 26.78% |
| Mock Male RFU (diluted 1/8) | 1734 | 4262 | 3303 | 3184 | 2229 | 2122 | 1157 | 3486 | 2686 | | | | | | | | | | | | | | | 2685 | 970 | 36.12% |
| IMA (X) total human est. pg of DNA | 120 | 290 | 228 | 221 | 160 | 153 | 91 | 240 | 189 | | | | | | | | | | | | | | | 189 | 62 | 32.85% |
| Mock Male RFU (diluted 1/16) | 1566 | 1240 | 1079 | 1561 | 1326 | 1478 | 1671 | 1792 | 1421 | 1591 | | | | | | | | | | | | | | 1475 | 213 | 14.46% |
| IMA (X) total human est. pg of DNA | 118 | 96 | 86 | 117 | 102 | 111 | 124 | 131 | 108 | 119 | | | | | | | | | | | | | | 111 | 14 | 12.20% |

Average σ of Total Human RFU: 1048, 23.16%
Average σ of Total Human DNA (pg): 67, 21.36%

Mock Male — Male-Only (SRY)

| Sample | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | μ | σ | CV |
|---|---|---|---|---|---|---|---|---|---|---|---|---|---|---|---|---|---|---|---|---|---|---|---|---|---|---|
| Mock Male RFU (diluted 1/2) | 6825 | 7312 | 7614 | 7425 | 7054 | 7657 | 7047 | 6333 | 6584 | 6277 | | | | | | | | | | | | | | 7013 | 501 | 7.15% |
| IMA (SRY) total male est. pg of DNA | 543 | 582 | 606 | 591 | 562 | 609 | 561 | 505 | 524 | 500 | | | | | | | | | | | | | | 558 | 40 | 7.10% |
| Mock Male RFU (diluted 1/4) | 2374 | 3642 | 2869 | 3412 | 2235 | 2901 | 2253 | 2178 | 2250 | 3219 | 2466 | 3189 | 3871 | 3231 | 3307 | 3926 | 4111 | 4250 | | | | | | 3094 | 693 | 22.39% |
| IMA (SRY) total male est. pg of DNA | 192 | 292 | 231 | 274 | 181 | 233 | 182 | 176 | 182 | 258 | 199 | 256 | 310 | 259 | 265 | 314 | 329 | 340 | | | | | | 249 | 55 | 22.01% |
| Mock Male RFU (diluted 1/8) | 2497 | 2575 | 1180 | 2720 | 1971 | 2189 | 1589 | 2118 | 2276 | | | | | | | | | | | | | | | 2124 | 491 | 23.10% |
| IMA (SRY) total male est. pg of DNA | 201 | 207 | 97 | 219 | 160 | 177 | 130 | 171 | 184 | | | | | | | | | | | | | | | 172 | 39 | 22.53% |
| Mock Male RFU (diluted 1/16) | 1129 | 1833 | 1065 | 1069 | 1458 | 1030 | 727 | 1327 | 578 | 1023 | | | | | | | | | | | | | | 1124 | 355 | 31.62% |
| IMA (SRY) total male est. pg of DNA | 93 | 149 | 88 | 89 | 119 | 85 | 61 | 109 | 50 | 85 | | | | | | | | | | | | | | 93 | 28 | 30.34% |

Average σ of Male-Only RFU: 510, 21.06%
Average σ of Male-Only DNA (pg): 40, 20.49%

Average σ pg of DNA in the male sample: 54, 20.93%

METHOD FOR SIMULTANEOUSLY DETERMINING IN A SINGLE MULTIPLEX REACTION GENDER OF DONORS AND QUANTITIES OF GENOMIC DNA AND RATIOS THEREOF, PRESENCE AND EXTENT OF DNA DEGRADATION, AND PCR INHIBITION WITHIN A HUMAN DNA SAMPLE

CROSS REFERENCE TO RELATED APPLICATION

This application claims the benefit of copending U.S. provisional application Ser. No. 60/870,770, filed 19 Dec. 2006, the complete contents of which are incorporated herein by reference.

SEQUENCE LISTING

This application includes as the Sequence Listing the complete contents of the accompanying text file "Sequence.txt", created Sep. 18, 2007, containing 2,562 bytes, hereby incorporated by reference.

FIELD OF THE INVENTION

This disclosure relates to genetic testing in general and, more specifically, to determining, in a single polymerase chain reaction (PCR) reaction, the quantity, quality, and gender of origin of DNA in a sample, and whether or not the sample contains PCR amplification inhibitors.

BACKGROUND OF THE INVENTION

It is common practice for forensic laboratories to quantitate the amount of human genomic DNA recovered from evidentiary biological samples. Motivation for the quantitation of the DNA, which is used as a polymerase chain reaction (PCR) template for multiplex amplification of short tandem repeat (STR) loci, include minimizing the amplification of partial DNA profiles, minimizing allele dropout or imbalance if template amounts are too low, or off-scale data, allelic/locus imbalance or other spurious artifacts when input template is too high (1-4). In addition, the laboratory is required to consume only what is needed to produce a result and retain the remaining evidence and/or DNA for independent testing by a different laboratory, should the court so order.

Standard 9.3 in the Quality Assurance Standards for Forensic DNA Testing Laboratories mandates that forensic DNA typing laboratories determine the amount of human genomic DNA recovered from samples (5). Any laboratory desiring accreditation/certification by accrediting agencies using these or other similar standards must quantitate human DNA recovered from biological evidence that is to be used for DNA typing.

Current non-specific methods available for DNA quantitation include the absorbance of ultraviolet light at 260 nm, quantitation of fluorescence in genomic DNA co-electrophoresed with known amounts of DNA in a "yield gel", and quantitation of fluorescence produced by intercalating fluorescent dyes (6). Specific methods for quantitating human chromosomal DNA include quantitative hybridization of human DNA probes to slot blots or dot blots of dilutions of DNA from unknowns and quantitation standards (7), quantitative measurement of fluorescence produced by dyes intercalating in Alu sequences amplified from human genomic DNA (8,9), and fluorescence produced by accumulating DNA product measured after each extension step in a PCR cycling program (i.e. real-time PCR) (10-13). Real time PCR methods incorporate primers that target specific genomic sequences in human DNA whose accumulation during repeated rounds of amplification can be measured and is proportional to the amount of input DNA template. Included among human loci targeted for real time PCR are Alu sequences scattered throughout the genome (8) or sites on the X and Y chromosomes (11) whose amplification can provide data not only on DNA quantity, but also on the sex of the sample and the possible existence of male:female mixtures in extracts. Information regarding the gender of the person(s) contributing the DNA can be of vital importance, especially in the investigation of sexual assault cases. For example, if a forensic sample from a female contains a mixture of both male and female DNA, this could support an allegation of assault, whereas the absence of male DNA in a sample might argue against an assault having occurred.

Of the methods described above, only those that employ the use of human specific probes or primers will meet the intent of the quality assurance standards in that they will produce an estimate of human DNA quantity. However, to date, the methods of doing so involve the use of materials and instrumentation other than that which is required for PCR amplification of the DNA. This means that a laboratory that is engaged in DNA forensic analysis must either invest in the necessary equipment and training, or subcontract the work to other labs that are so equipped, both of which options are inefficient.

Another problem that plagues DNA analysts is that sometimes, in spite of a sufficiently high concentration of DNA in a sample, amplification of the DNA is inadequate due to the presence of PCR inhibitors. Such inhibitors may originate from clothing, dirt, etc. to which the sample has been exposed. While samples can be "cleaned up" to remove inhibitors, valuable sample and time may be wasted in detecting the presence of inhibitors, especially when samples are dealt with on a case by case basis.

The prior art has thus-far filed to provide a convenient method to, in a single reaction, analyze a DNA sample with respect to quantity, quality, presence of inhibitors, and gender of donor. In particular the prior art has failed to provide a method to obtain this information that requires only the use of equipment and personnel trained to carry out routine PCR, without additional instrumentation, supplies or training.

SUMMARY OF THE INVENTION

The present invention provides methods for obtaining crucial information about the DNA content of a sample of interest (e.g. a forensic sample) in a rapid, efficient and sensitive manner. By utilizing a combination of oligonucleotide primers as described herein, it is possible to ascertain, in a single multiplex PCR reaction, the quantity of human genomic DNA present in the sample, the gender of the DNA donor (or donors), the "quality" of the DNA (i.e. the extent of DNA degradation that has occurred in the sample), and whether or not the sample contains significant levels of PCR inhibitors. The assay, which is referred to herein as "Q-TAT" for "Quantitative template amplification technology", is both sensitive and reproducible, and enables a forensic DNA typing lab to use existing technology and instrumentation in conjunction with a well characterized DNA standard to produce concentration estimates of DNA in biological samples. Q-TAT thus represents an alternate method useful for the quantitation of human genomic DNA prior to amplification of STR loci used for identity testing purposes. In addition, the actual cost of carrying out other similar methods is about $10.00, even though the charge to the consumer is about $40.00. In contrast, the cost of carrying out a Q-TAT reaction can be less than $1.00, so even with a commercial markup, the cost to the consumer will be significantly less than that of currently available methods.

The method, involves carrying out a single, PCR multiplex reaction utilizing primer sets specific for amplifying the human amelogenin locus, an X- and/or Y-chromosome specific gene that is shorter on the X chromosome, an additional Y chromosome specific marker known as SRY, and a heterologous, non-human reporter gene. DNA quantitation is accomplished by comparing the fluorescence of amplicons produced from the X and/or Y amelogenin locus or the SRY locus with fluorescence in a standard curve of fluorescence from amplicons obtained from known quantities of reference DNA. The gender of the DNA donor(s) can be determined by comparing the relative fluorescence of X and Y amplicons of amelogenin. The X chromosome version of amelogenin is shorter than the Y chromosome version, and the two can thus be readily distinguished from each other. The extent of degradation in the sample is determined by comparing the amount of fluorescence of amplicons of amelogenin with fluorescence from amplicons from a shorter X- and/or Y-chromosome specific gene, such as the Sex-Determining Region Y (SRY) gene. Use of an additional Y-chromosome specific gene also serves as a "back-up" indicator of the gender male DNA donors, if the male DNA donor has a mutation that prevents amelogenin amplification with primers specific for the predominant form of the gene. Finally, the presence of PCR inhibitors in the sample can be ascertained by comparing the fluorescence levels of amplicons of a non-human reporter DNA sequence that is added to and co-amplified with the sample, with fluorescence in a control reaction containing a known quantity of the reporter sequence and that is inhibitor-free.

The method involves the steps of obtaining a sample; creating a reaction mix by combining an aliquot of the sample and DNA encoding a non-human reporter sequence; and PCR amplifying the reaction mix in a single multiplex PCR reaction using a plurality of primer sets. The primer sets include a) a first primer set comprising synthetic oligonucleotide primers directed against a human amelogenin gene; b) a second primer set comprising synthetic oligonucleotide primers directed against a human Y-chromosome specific gene or a human X-chromosome specific gene, or both; and c) a third primer set comprising synthetic oligonucleotide primers directed against said non-human reporter sequence. Finally, the method involves the step of detecting PCR amplicons produced in said step of PCR amplifying. Results obtained in said detecting step are indicative of the genomic DNA quantity, the extent of genomic DNA degradation, the gender of the genomic DNA donor(s), and the presence of PCR inhibitors in the sample. In general, amplicons produced by PCR amplification of the human Y-chromosome specific gene and the human X-chromosome specific gene are shorter than amplicons produced by PCR amplification of the human amelogenin locus. In one embodiment of the invention, the Y-chromosome specific gene is Sex-Determining Region Y (SRY). In another embodiment of the invention, the non-human reporter sequence is a luciferase gene, e.g. Sea pansy luciferase. The synthetic oligonucleotides typically include a detectable label, e.g. a fluorescent label.

A kit for carrying out the method is also provided. Such a kit typically comprises:

a) a first primer set comprising synthetic oligonucleotide primers directed against a human amelogenin locus;

b) a second primer set comprising synthetic oligonucleotide primers directed against a human Y-chromosome specific gene or a human X-chromosome specific gene, or both;

c) a third primer set comprising synthetic oligonucleotide primers directed against a non-human reporter genetic sequence; and d) a reporter gene. In general, amplicons produced by PCR amplification of the human Y-chromosome specific gene and the human X-chromosome specific gene are shorter than amplicons produced by PCR amplification of the human amelogenin locus. In one embodiment of the invention, the Y-chromosome specific gene is Sex-Determining Region Y (SRY). In another embodiment of the invention, the non-human reporter sequence is a luciferase gene. The synthetic oligonucleotide typically includes a detectable label, e.g. a fluorescent label.

BRIEF DESCRIPTION OF THE DRAWINGS

FIG. 14. Reproducibility of Estimation of DNA Content of Unknown Samples by the Repetitive Analysis of Pure Male and Pure Female Unknowns. A pure female mock evidence sample and a pure male mock evidence sample was diluted by halves as described in Materials and Methods. Each dilution was amplified multiple times and injected for five seconds on a 310 genetic analyzer. The height RFU for the amelogenin and SRY amplicon from each amplification was averaged and the standard deviation and coefficient of variation was calculated. The height RFU values were compared to a standard curve and the estimation of total human and total male DNA was determined for each sample. The average, standard deviation and coefficient of variation for each estimated amount of DNA was calculated. The standard deviation and coefficient of variation for both the height RFU and estimated amount of DNA for each dilution was calculated as well as the average standard deviation and coefficient of variation in the male sample from the averages of the male-only and total human from the male sample.

FIG. 15. Size-Calling Precision and Peak-Height Quantification Precision in Five 310 CEFD devices. To determine the percent CV for a CEFD device, we serially injected (eighteen times in a row) one sample of the amplification products from an AmpFlSTR® Identifiler™ DNA profiling reaction performed on the Identifiler™ female positive control 9947A sample provided with the Identifiler™ kit on five different CEFD devices. By analyzing the average peak-height fluorescence data and size-calling data of only the TH01 9.3 allele peak, we determined the percent CV of a CEFD device for size-calling and for electrokinetic injection and fluorescence detection of a sample by averaging this data and calculating percent CV over the eighteen serial injections of this single sample. Because a single sample was analyzed over eighteen injections, no pipetting error would be included in the CV value determined. The lower five segments of this table describe the data gathered over ten serial injections of a sample exhibiting the TH01 9.3 allele for just the first CEFD device from the top segment of the table. The conditions of the CEEFD device during the collection of the data for each grouping of ten serial injections is described above each segment. We concluded that with proper attention to CEFD maintenance issues that effect quantification precision, any CEFD device can have a percent CV of 5% or less.

DETAILED DESCRIPTION OF THE PREFERRED EMBODIMENTS

Figure 1:
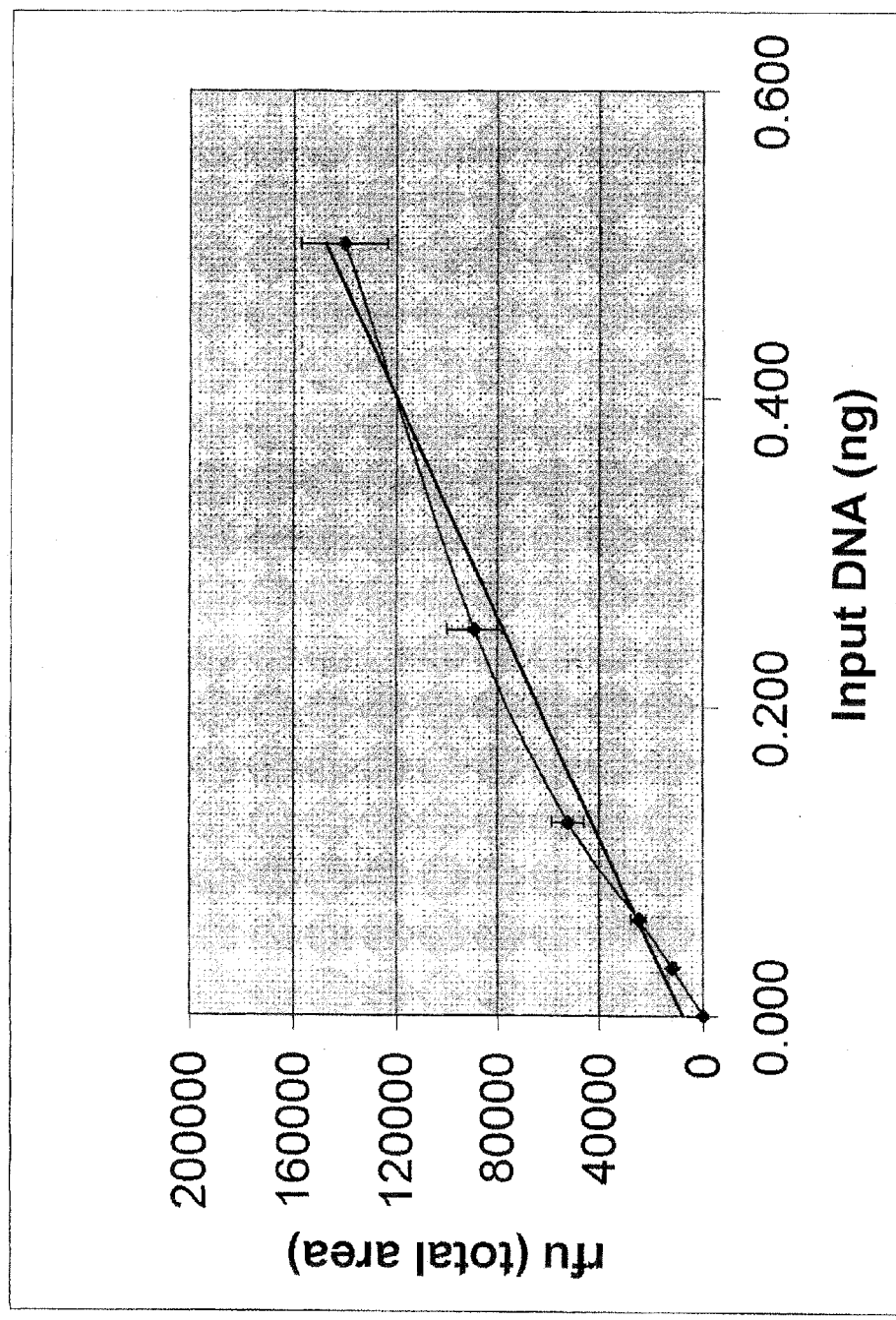
FIG. 1 is graph of standard curves produced using male reference DNA and Q-TAT in 10 independent assays.

The Q-TAT assay is a PCR based assay that provides useful information about a DNA sample. The assay permits an investigator to determine, in a single PCR reaction: 1) the amount of total human DNA present in the sample; 2) the quality (i.e. extent of degradation) of the DNA 3) whether the sample contains DNA from a male donor, a female donor, or both; and 4) whether or not PCR inhibitors are present in the sample.

The ability to determine the quantity of DNA allows the investigator to design appropriate conditions for carrying out PCR reactions to identify the donor without using either too little DNA (and thus risking an insufficient signal for analysis) or too much DNA (and thus wasting the sample and interfering with the signal that is to be analyzed). Thus, the method allows an investigator to choose among several samples to send for further DNA profiling, or to select the best conditions for profiling, or to further prepare samples for profiling, i.e. to send the best possible sample, a sample that is likely to produce reliable, useful results when further DNA typing is carried out.

Forensic samples are sometimes recovered from a scene in which the degradation of the DNA template is accelerated. For example, numerous DNA samples from the World Trade Center disaster were badly degraded due to the heat of the fire. The ability to determine the quality (i.e. to provide an estimate of the integrity and/or degradation) of DNA in a sample is accomplished through the inclusion of primers in the reaction that direct the amplification of two differently sized templates. If the DNA is degraded, the smaller template would be expected to be less affected than the larger template, and thus the quantity of amplicons produced from the smaller product would be greater than the amount produced from the larger template. This analysis allow an investigator to more accurately predict the successful amplification of longer alleles suitable for DNA profiling of the sample, and to adjust PCR reaction conditions accordingly.

The ability to determine the gender of the DNA donor can be extremely helpful. For example, is sexual assault cases, a sample taken from a female would logically contain both female and male DNA if an assault has actually occurred. Absence of male DNA in a sample may indicate that there was, in fact, no assault. In other words, Q-TAT provides the forensic community with the ability to terminate analysis of non-probative evidentiary samples (i.e. no male DNA present) before expending resources for unnecessary DNA profiling.

Finally, DNA recovered from certain types of forensic substrates (blue jeans, blood, or soil for example) often contains chemicals that will inhibit the PCR reaction. Thus, the Q-TAT assay includes a non-human control DNA template whose amplification is expected unless a forensic DNA sample contains inhibitors. The ability to detect the presence/absence of PCR inhibitors is a boon in that an investigator will then know whether or not extra clean-up steps should be carried out to rescue the DNA in a sample to make it useful for DNA typing, thereby avoiding needless waste of samples and resources.

A particular advantage of the invention is that the Q-TAT assay is carried out in a single PCR reaction and requires the same equipment, supplies and personnel training that already exist in facilities that conduct DNA testing (e.g. DNA profiling or typing) using PCR technology. No stand alone procedures are required. In other words, the assay utilizes PCR and electrophoresis with fluorescent detection/quantitation as used in typical DNA profiling, precluding the need for new instrumentation, methodology, or quality assurance associated with slot-blot or real-time PCR. To perform the Q-TAT assay, a commercially available human sex typing kit, a thermal cycler, and a genetic analyzer are all that are required Q-TAT thus bridges the information gap between biological screening and final DNA profiling. Further, while the assay is suitable for use on a sample by sample basis, it may be advantageously used to screen large numbers of samples prior to subjecting them to a detailed PCR analysis. This is especially helpful given the large number of samples that are currently backlogged at DNA analysis facilities. For example, the assay may be used to initially screen several hundred or several thousand samples to obtain the information described above. The samples can then be divided into categories such as those which must be further processed to remove PCR inhibitors prior to final PCR analysis, and those which do not need further processing. In addition, for cases where such knowledge is pivotal, samples that are putative sexual assault evidence and that contain male DNA even though obtained from a female could be classified as suitable for further analysis, whereas if no male DNA is detected, they could be eliminated. Finally, because the quantity and quality of the DNA in a sample has been determined by Q-TAT, PCR reaction conditions for samples deemed immediately suitable for further processing could be adjusted to maximize reliable signals in further PCR analysis, without wasting valuable sample.

The Q-TAT assay is a multiplex PCR reaction in which, in one embodiment, primers directed against the human amelogenin locus, the Sex-Determining RegionY (SRY) gene, and a non-human gene are included in a PCR reaction mix. The amelogenin locus is present in both the X and Y chromosomes, but the locus is longer in the Y chromosome. Therefore, amplification of amelogenin produces products of different size, depending on whether the locus on of the X or Y chromosome is amplified. Amplification of samples containing male or a mixture of male and female DNA will produce both products. Amelogenin thus serves as an indicator of the gender of the DNA donor(s). Further, comparison of the quantity of fluorescence produced by Q-TAT amplification of amelogenin to fluorescence produced by a known quantity of the locus indicates the concentration of DNA in the sample. The SRY gene is located only on the Y chromosome. Amplification of this gene confirms that male DNA is present in the sample and, because it is shorter than either the X or Y amelogenin locus, serves as an indicator of the quality of DNA in a sample that contains male DNA. Moreover, since amelogenin X and Y amplicons exhibit sizes of 210 bp and 216 bp respectively, integrity as well as concentration of the genomic DNA template can be assessed. The inclusion of a non-human gene of known quantity in the Q-TAT reaction mix allows an assessment of the presence/absence of PCR inhibitors. If no inhibitors are present, the gene will be amplified optimally and produce a predictable signal. If the expected signal is diminished, then PCR inhibitors are likely present. If no male DNA is present in the sample, the amount of female DNA can be quantitated and the presence of inhibitors can be detected as described, without estimating the extent of degradation.

In another embodiment of the invention, a human X-chromosome specific gene is amplified. Examples of X-chromosome specific genes include but are not limited to hypoxanthine-guanine phosphoribosyl transferase (HGPRT), coagulation factor VIII, etc. In yet another embodiment of the invention, primers for both a Y-chromosome specific gene and an X-chromosome specific gene are included in the reaction mixture.

To carry out the Q-TAT reaction, one member of each primer set is labeled. Many types of labels that are suitable for use in PCR reactions are known to those of skill in the art, including but not limited to fluorescent labels, radioactive labels, affinity labels, electromagnetic labels, etc. In one embodiment of the invention, the label is a fluorescent dye, examples of which include but are not limited to FAM (a derivative of fluorescein), Oregon Green®468, BODIPY FL, JOE, TAMRA, ROX, Texas Red, VIC, NED, the CY (cyanine) dyes, LIZ, etc. In a preferred embodiment, the label is the fluorescent dye FAM.

The Q-TAT PCR reaction mixture contains a suitable quantity of a non-human gene. In one embodiment of the invention, the non-human gene is a luciferase gene, e.g. luciferase from the Sea pansy, an ocean coelenterate. The probability that a biological sample from a mammal (e.g. human) would contain such DNA is vanishingly small. However, those of skill in the art will recognize that other non-human genes that are readily amplified and quantitated may also be used in the practice of the invention. In a preferred embodiment of the invention, the Q-TAT reaction mix contains about 0.5 to about 1.0 pg of a recombinant plasmid containing the Sea Pansy luciferase gene.

Each PCR reaction contains an aliquot of extract from a sample to be analyzed, plus a known quantity of non-human DNA and a DNA polymerase. Those of skill in the art will recognize that several DNA polymerases are commercially available and could be used in the practice of the invention, examples of which include but are not limited to *Thermus aquaticus* ("Taq") polymerases such as AmpliTaq® and AmpliTaq Gold®, commercially available blends of Taq DNA polymerase and proofreading enzymes, *Pyrococcus furiosus* ("Pfu") polymerases such as Pfu-X polymerase and/or commercially available genetically engineered Pfu-X polymerase; polymerases from species such as *Thermas flavus, Thermus themophilius, Thermus litoris, Thermaotoga maritima*, etc. In preferred embodiments, the DNA polymerase is AmpliTaq Gold® (Applied Biosystems, Inc.) or a preblended master mix containing Taq polymerase such as Go-Taq® from Promega Corp. (Madison, Wis.). Amplification is carried out during a thermal cycling program designed not to exhaust reactants. Those of skill in the art are well acquainted with the development of PCR cycling programs, which are described, for example, in Butler J M (2005). *Forensic DNA Typing. Biology, Technology and Genetics of STR Markers*. Burlington, Mass.: Elsevier Academic Press. Following completion of the cycling, aliquots of PCR products (amplicons) are separated and the associated signals are quantitated by any of several suitable methods known in the art. For example, amplicons may be separated by capillary electrophoresis (e.g. in an ABI 310 Prism Genetic Analyzer or other multi-capillary genetic analyzer platform). Signals associated with the non-human gene, SRY, and X+/−Y amplicons are captured and can be quantitated, for example, using standard curves amplified from known quantities of reference DNA (e.g. as relative fluorescent units (rfus) when fluorescent labels are used). The relative signal in X and Y amplicons can be compared with the signal in amplicons produced in reactions carried out with known amounts of human DNA and the gender(s) of origin of the sample can be determined. The presence of inhibitors is determined by the signal present in the amplicon produced from the non-human gene target present in a constant amount in each sample. Reduction or obliteration of the non-human signal in the unknown sample, compared to the signal in a control reaction known to contain no PCR inhibitors, would indicate the presence of inhibitors in the DNA sample, and the need for cleanup of the sample. Finally, if amelogenin-Y or SRY amplicons are detected, then the presence of male DNA in the sample is confirmed. In addition, the SRY amplicon is about one-half the size of the amelogenin products. Therefore, if the ratio of the amount of SRY amplicon signal to amelogenin amplicon signal is greater than 1, it would suggest degradation of the DNA template, suggesting the use of a DNA typing methodology that favors producing results from degraded templates.

Those of skill in the art will understand that experienced practitioners are frequently able to predict a reasonable range of likely DNA concentrations within an unknown sample, and may thus be able to select a suitable quantity of the unknown sample for analysis. However, in many instances it may be preferable to test several dilutions of the sample (e.g. from about 2 to about 5 or with the intention of "bracketing" optimal conditions for PCR amplification and signal capture. For example, testing a single 25 fold dilution along with an undiluted sample would extend the useful dynamic range of the Q-TAT assay from about 50 pg/µl up to over 10 ng/µl, a rnage useful for most crime scene samples consisting of biological evidence. The additional data points that are obtained can be helpful to confirm the quantity/concentration or DNA in the unknown, experimental sample, as well as to confirm the results obtained with the other amplified loci.

In a comparison study incorporating shared samples (see Examples below), Q-TAT was found to be more sensitive than widely used slot-blot methods but somewhat less sensitive than real time PCR. Nevertheless, incorporating the Q-TAT method into the normal workflow may be more attractive to some laboratories than making the commitment to add real time PCR technology, which will involve funding, space allocation, training, and other QA/QC issues. Among samples containing DNA concentrations ranging from 100 pg/ul to 2-4 ng/ul, Q-TAT produced DNA concentration estimates that agreed well with either Quantiblot® or real time PCR. Q-TAT was reproducible with a typical coincidence of variation of about 35%. Quantitation of human DNA in the studies involved summing fluorescence in amelogenin X and Y amplicons in unknowns and quantitation standards. However, analyzing fluorescence in X and Y amplicons individually could also allow estimates of male and female DNA present in mixtures to be made. The Q-TAT method will detect as little as 20-30 pg of human DNA and has a dynamic range that extends to about 500 pg.

Those of skill in the art will recognize that the methods of the invention can be applied to the analysis of DNA from many sources and for many reasons, examples of which include but are not limited to: analysis of forensic samples, especially samples associated with sexual assault cases, but also for identification of unidentified persons (either living or dead); paternity testing; genetic testing for genealogical purposes; genetic testing of any type of remains, e.g. fossilized, mummified, etc.; molecular testing for human genetic diseases, etc.

Samples that may be assayed by the methods include any that contain or are believed to contain DNA, such as swabs (e.g. vaginal, buccal, etc.); hair; blood; skin or skin cells; blood; prenatal samples (e.g. amniotic fluid); tissue biopsies, etc.

In a preferred embodiment, the assay is conducted on samples obtained from mammals such as humans. However, those of skill in the art will recognize that the methods may readily be adapted to analyze DNA samples from other mammals or other species as well.

EXAMPLE 1

Materials and Methods

DNA Extraction

DNA was extracted from non-probative forensic samples used in this study with standard methods employing SDS and proteinase K digestion followed by phenol:$CHCl_3$:isoamyl alcohol (9:0.96:0.04 vol/vol) extraction (14). Reference samples were extracted using the same methods, or, using inorganic extraction methods based on the original work of Miller et. al. (15). The male and female DNA used to produce the standard curves were extracted from blood samples supplied by lab workers and were dispensed in aliquots in 10 mM Tris-Cl pH 8.3+0.1 mM EDTA (TE-4) and stored at −20° C. for repetitive use. Quantities of DNA in these reference standards were established by absorbance at 260 nm as well as through the use of a yield gel, comparing ethidium bromide fluorescence produced by a range of known concentrations of lambda DNA co-electrophoresed with dilutions of the human genomic DNA samples to be used as quantitation standards. Concentration estimates of the human standards were further evaluated by amplifying what was calculated to be a 1 ng aliquot of reference DNA (based upon the A260 and yield gel estimates) with the Profiler Plus STR typing kit (Applied Biosystems, Foster City, Calif.) according to recommendations from the supplier. Peak relative fluorescence unit (rfu) measurements of alleles amplified from the reference template exhibited average peak heights of 1000-3000 rfu, which is consistent with expectations when using 1 ng of good quality DNA template.

PCR Amplification and Genetic Analysis

Samples were amplified by PCR using either a PTC-200 (MJ Research, Reno, Nev.) or an ABI 9700 thermal cycler (Applied Biosystems, Foster City, Calif.). Profiler Plus amplifications were set up following the instructions supplied with the STR typing kit (Applied Biosystems, Fullerton, Calif.).

Amplification of X and Y products using the amelogenin, sex typing kit (Promega Corp., Madison, Wis.) was performed as directed by the kit instructions except Ampli-Taq Gold DNA polymerase (Applied Biosystems, Foster City, Calif.) and GoldSTR reaction buffer (Promega Corp., Madison, Wis.) were substituted in place of the reagents recommended or supplied with the kit. In addition, 12.5 µl reaction volumes were substituted for the 25 µl volumes specified in the manufacturer's protocol. The primers in this kit are labeled with fluorescein and are reasonably specific for primate DNA although small amounts of product whose size differs from the human products can be produced with the genomic DNA from other species as well (16).

Amplification products produced either with the Amelogenin or Profiler Plus kits were mixed with formamide (Applied Biosystems, Foster City, Calif.) containing GS350 or GS500 size standards (Applied Biosystems, Foster City, Calif.) according to recommendations of the supplier. The samples were then subjected to electrophoresis and fluorescent analysis with the aid of an ABI Prism 310 Genetic Analyzer (Applied Biosystems, Foster City, Calif.).

Each Q-TAT assay incorporated the creation of a standard curve produced by quantitating fluorescence in X or X+Y amplicons produced with 0, 31.25 pg, 62.5 pg, 125 pg, 250 pg, or 500 pg of human reference DNA template. The standard curve was produced as follows: DNA serving as the human quantitation standard was diluted to 500 pg/µl in $dH_2O$ initially and then serially diluted 2 fold to establish the concentration range. One microliter aliquots of each dilution were then used as template for amplification of X, or X and Y alleles in a 12.5 µl PCR reaction. Each assay also included a 100 pg aliquot of positive control DNA contained within the Profiler Plus STR typing kit (Applied Biosystems, Foster City, Calif.) to serve as an internal quantitation control.

Data Analysis

For estimation of the DNA concentrations in unknowns, the relative fluorescence in the X (and possibly Y) amplicons were compared with the fluorescence in X+Y amplified from known amounts of reference DNA template using the following strategy: The area under the curves of the X/Y products in each dilution of reference DNA was summed and normalized for the different injections through comparison to the total rfu contained within the 200 bp standard present in the GS350 or GS500 size standards. Since the size standard mixture is present in constant amounts in each sample (due to the use of a master mix of formamide/size standard that is prepared and aliquoted into the sample tubes needed for each assay), variation in the fluorescence in X/Y amplicons resulting from subtle injection fluctuations or laser/CCD camera variability can be normalized across the run. Normalized fluorescence in X/Y amplicons per input ng of reference DNA could then be computed from the slope of the standard curve. Fluorescence in X/Y products from unknowns was simply plotted on the standard curve to estimate their respective template concentrations.

DNA Quantitation Using Quantiblot and Real Time PCR

Estimates of DNA concentration in samples processed by the Tulsa Police Laboratory were produced using blotting/hybridization methods incorporated into the Quantiblot kit available from Applied Biosystems (Foster City, Calif.). Quantiblot estimates were made following colorimetric visualization of probe hybridization to quantitation standards and unknowns slot-blotted onto nylon membrane according to manufacturer's instructions. The highest concentration of quantitation standard on the slot blot contained 8 ng/µl (the QA++ standard) of human genomic DNA supplied with the QB kit. Serial two-fold dilutions were made of this DNA sample and blotted on the membrane with the least concentrated sample corresponding to 0.0325 ng/µl (the QG sample). In estimating the DNA concentration in unknowns however, any sample producing a color fainter than the 0.125 ng/µl standard (the QE standard) was labeled as <QE and no attempt were made by the analyst to estimate concentration more accurately.

DNA was quantitated using a 7000SDS thermal cycler and the Quantifiler kit (both obtained from Applied Biosystems, Foster City, Calif.).

Results

The strategy for quantifying human genomic DNA in extracts was to generate a standard curve of fluorescence in amelogenin amplicons produced from known quantities of input human template DNA. Highly reproducible standard curves could be produced using either male or female reference human genomic DNA (FIG. 1). Substituting female rather than male DNA as the quantitation standard had no significant effect on the concentration estimates for unknowns (not shown). This is likely due to the comparable efficiency of amplification of the amelogenin gene on the X and Y chromosomes. Thus, each copy of the amelogenin gene on each of the two X chromosomes in a female would produce the same amount of total amplicon fluorescence as product amplified from one copy of the gene on X and the other located on Y in the male.

FIG. 1 is graph of standard curves produced using male reference DNA and Q-TAT in 10 independent assays. Standard curves were produced by amplifying 0, 31.25 pg, 62.5 pg, 125 pg, 250 pg, and 500 pg aliquots of male reference DNA using the sex typing kit as described in Materials and Methods. Shown at each data point is the mean fluorescence incorporated into the X and Y amplicons from 10 separate assays along with error bars reflecting a coincidence of variation of approximately 25% at all concentrations of input reference DNA. Also shown is a best fit of the data from the ten separate assays ($R^2$=0.9751).

Several features of the Q-TAT method are apparent from FIG. 1. The sensitivity of the method for reliably detecting human DNA is operationally about 20-30 picograms. This level of sensitivity should be adequate for most forensic applications. It is also apparent from FIG. 1 that one limitation of the assay is the dynamic range which extends only over a 10-20 fold span of concentration before the curve begins to plateau, possibly due to depletion of primers or other reactants in the amplification reaction, or for as yet undefined reasons as discussed by Morrison and Gannon (17). Reducing the number of cycles could help alleviate this problem, but sensitivity could be compromised as a consequence. As an alternative approach, a small dilution series of an extract would likely produce a result within the acceptable range of the standard curve. The PCR conditions chosen therefore represent a good working balance between sensitivity and usable concentration range for input DNA.

Figure 2A:
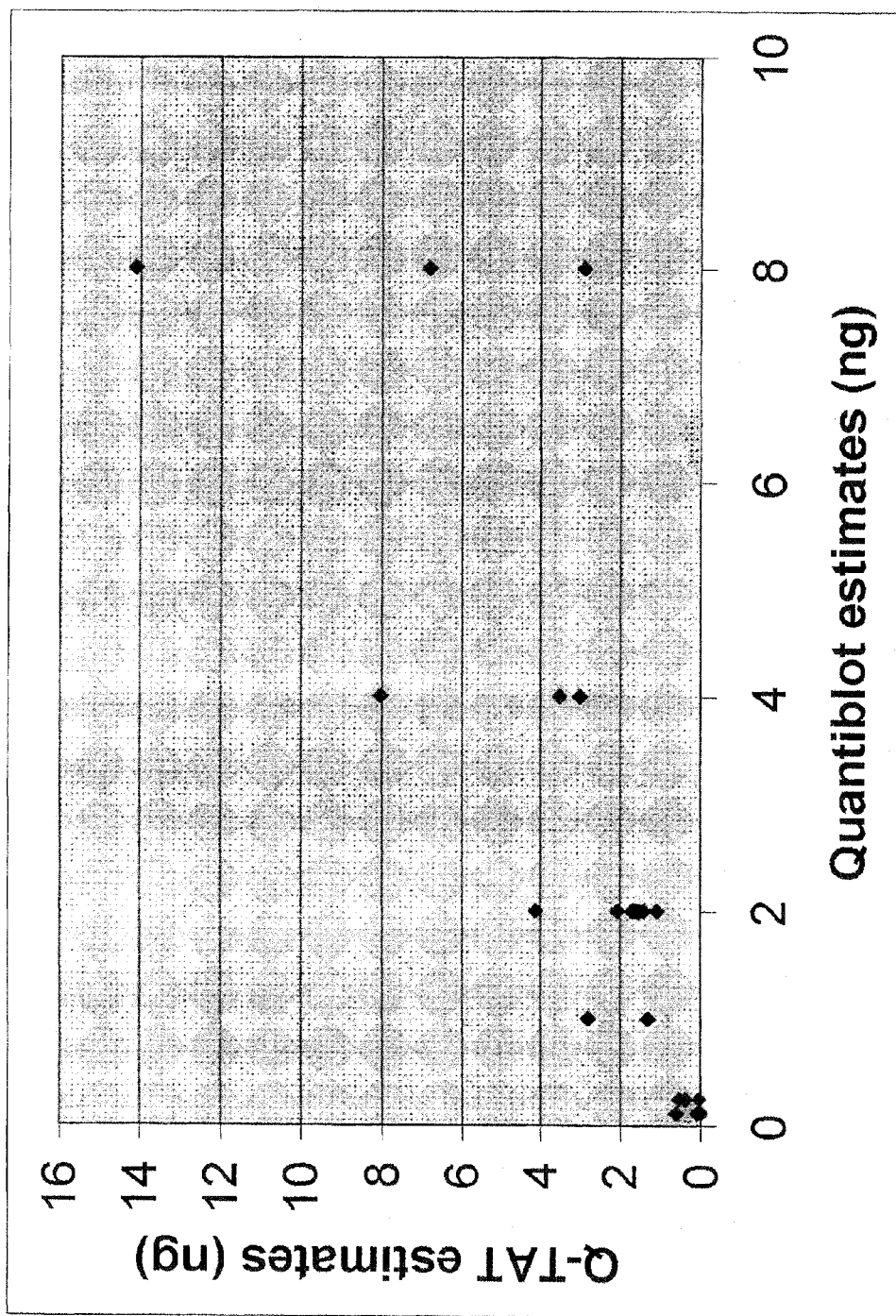
FIGS. 2A-B. A, graph of a comparison of Quantiblot® and Q-TAT quantitation methods with shared human DNA samples. B, graph of estimates of DNA quantity in the positive control sample in Profiler Plus and Identifiler STR typing kits.

FIG. 2A is a graph of a comparison of Quantiblot® and Q-TAT quantitation methods with shared human DNA samples. A group of 30 non-probative human DNA samples extracted from suspects, victims, and evidentiary item were quantitated with both QB and Q-TAT. Estimates of DNA concentration produced for each sample with the two methods were then plotted as a scatter plot. DNA concentration estimates were made using QB by an analyst with several years experience using the method and consisted of assigning unknowns to concentration categories spanning a range from QA++ (8.0 ng/ul) to <QE (<0.125 ng/ul). The analyst does not incorporate the QF (0.06 ng/ul) and QG (0.03 ng/ul) categories suggested in the instructions provided with the QB kit into concentration estimates of unknowns.

Figure 2B:
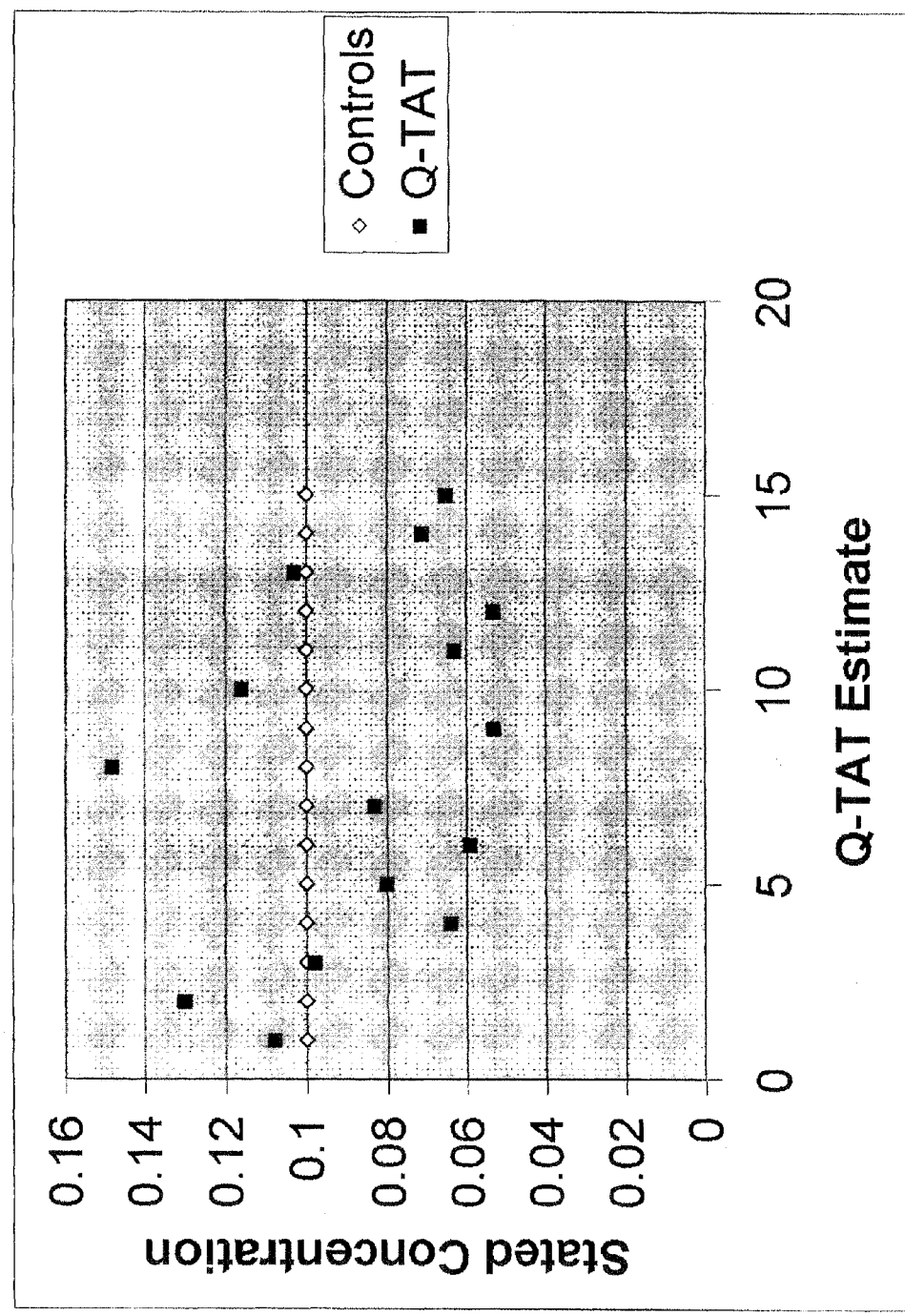

FIG. 2B is a graph of estimates of DNA quantity in the positive control sample in Profiler Plus and Identifiler STR typing kits. The vial of positive control DNA sample supplied with STR typing kits from Applied Biosystems was used as a quantitation control in each Q-TAT assay. Quantity estimates obtained by Q-TAT were plotted along with the quantity of DNA indicated on the vial in the STR typing kit.

Figure 3:
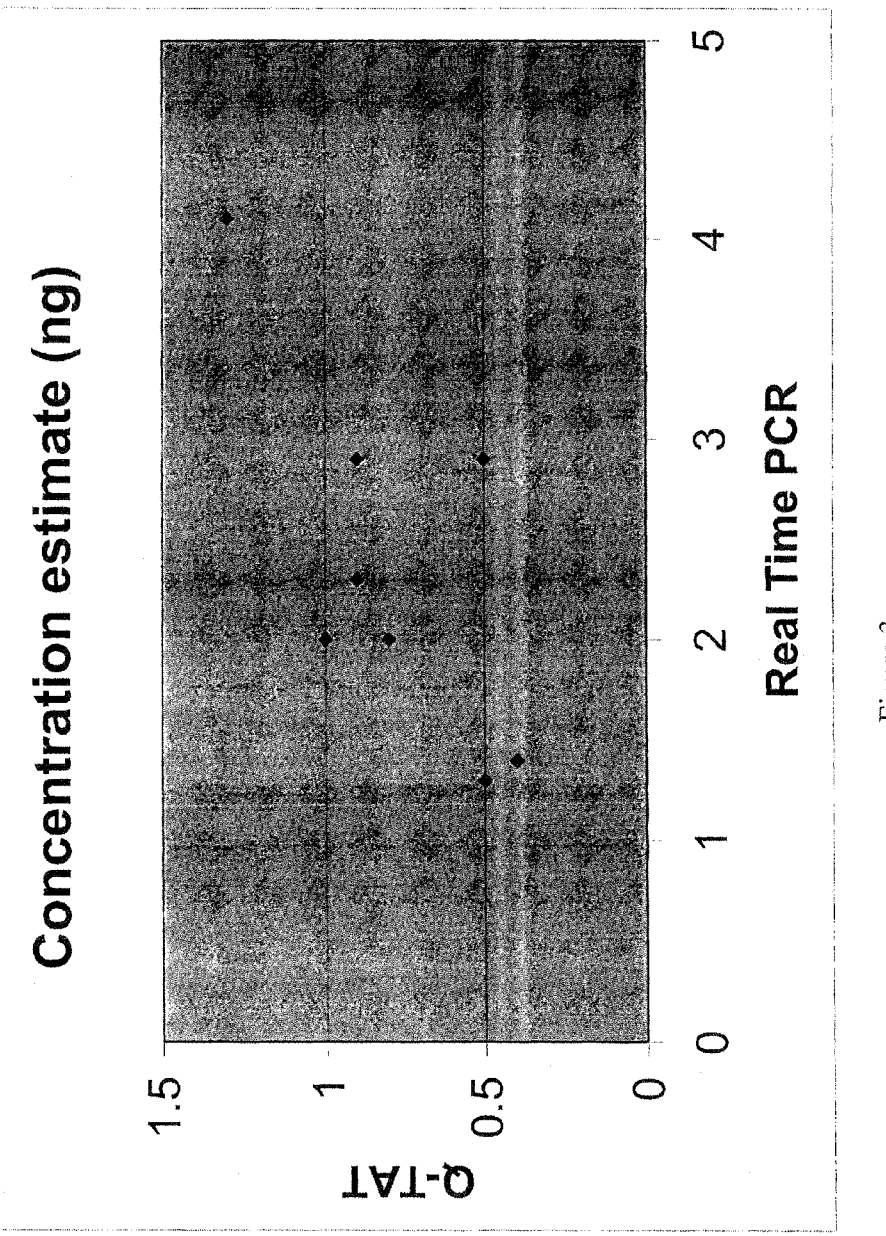
FIG. 3 is a graphical comparison of real time PCR and Q-TAT quantitation methods with shared human DNA samples.
Figure 4A:
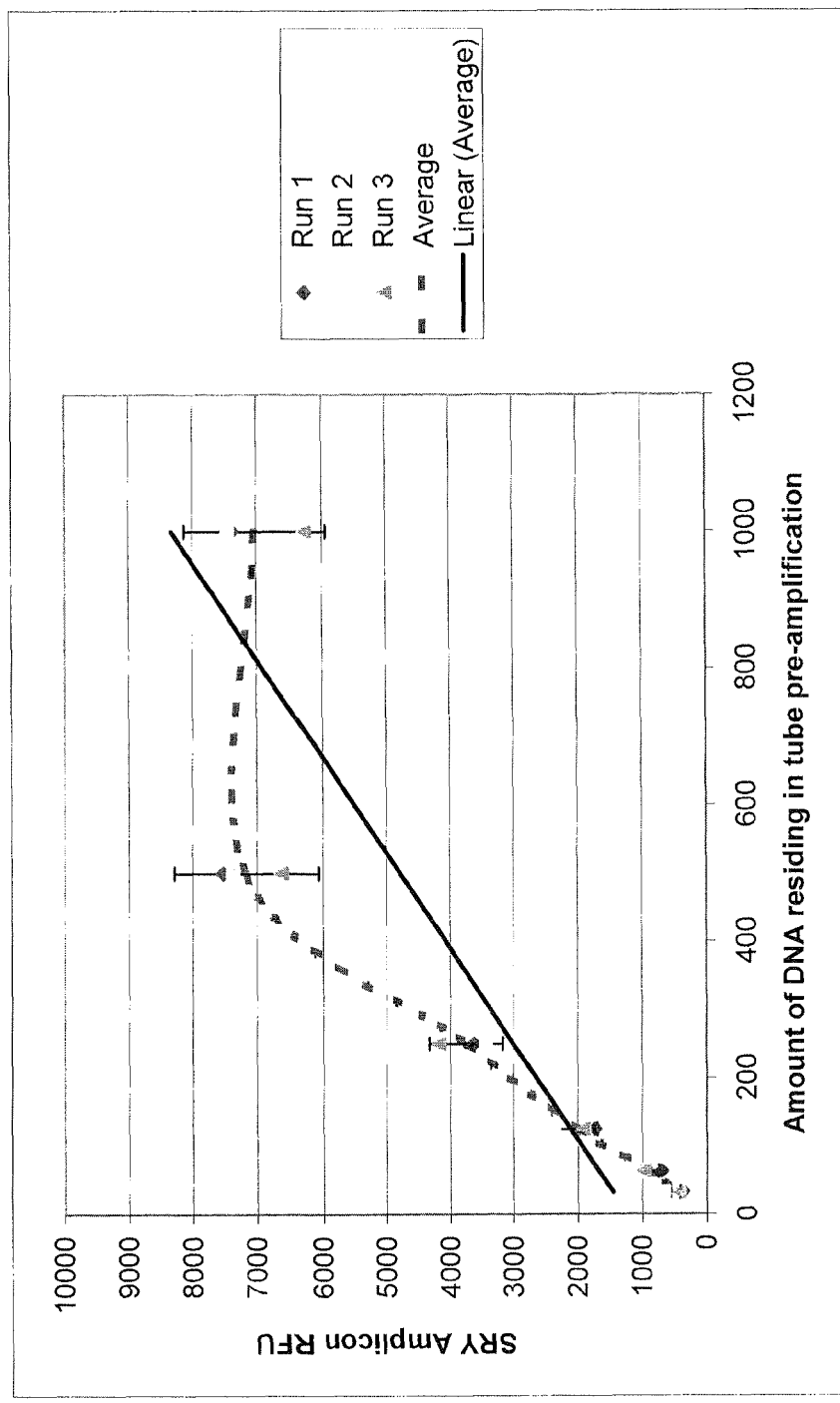
FIGS. 4A-B. Imperfect Standard Curve A, This standard curve was produced using the NIST SRM 2372 Standard A male sample assayed by the improved multiplex assay from three independent analyses. Standard curves were produced by amplifying a serial dilution of the Standard A male sample as described in Materials and Methods. At each data point, the fluorescence incorporated into the SRY amplicon from three separate assays and the mean of the three assays is shown along with error bars reflecting a coefficient of variation of 15.55% at all concentrations of input reference DNA. A linear regression line of the data from the average of the three separate assays ($R^2=0.784$) is also shown. Each data point was gathered by an ABI Prizm 310 Genetic Analyzer using GeneScan® Analysis version 3.1.2 with the default settings for peak analysis. We noted no difference in the estimation of peak height by changing the default peak analysis settings to "light" or "no" smoothing or by switching between the various size-calling settings. Changing these settings does, however, effect the estimation of peak area by causing broad, truncated peaks to have a lower RFU value because they are smoothed. B, This standard curve was produced using the NIST SRM 2372 Standard B male sample assayed by the improved multiplex assay from three independent analyses. Standard curves were produced by amplifying a serial dilution of the Standard B female sample as described in Materials and Methods. At each data point, the fluorescence incorporated into the X amplicon from three separate assays and the mean of the three assays is shown along with error bars reflecting a coefficient of variation of 22.13% at all concentrations of input reference DNA. A linear regression line of the data from the average of the three separate assays ($R^2=0.9288$) is also shown. Each data point was gathered by an ABI Prizm 310 Genetic Analyzer using GeneScan® Analysis version 3.1.2 with the default settings for peak analysis.
Figure 4B:
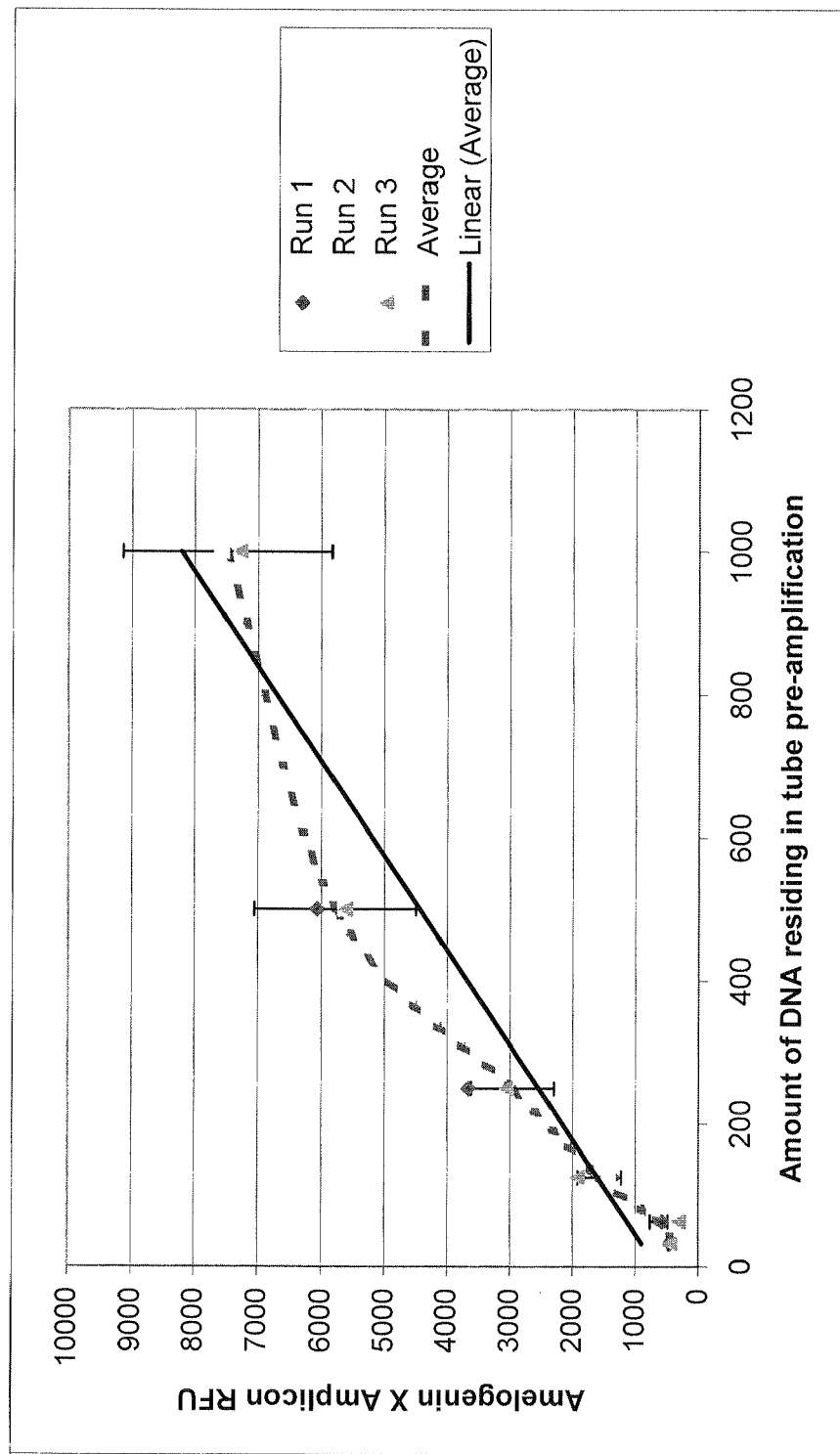

FIG. 3 is a graphical comparison of real time PCR and Q-TAT quantitation methods with shared human DNA samples. A group of 10 DNA samples previously quantitated using real time PCR (with the Quantifiler kit from Applied Biosystems, Inc.) were subjected to quantitation using Q-TAT.

An important test of any new method is whether it passes validation through comparison to existing, accepted methods. As part of the Q-TAT validation process, Q-TAT was used to quantitate DNA in a cohort of samples supplied by other labs that had been subjected to prior quantitation using Quantiblot® (QB) or real time PCR. The results of the comparisons are shown in FIGS. 2A, 2B, and 3. Comparison between DNA concentration estimates by QB and Q-TAT are shown as scatter plots in FIG. 2A. Most samples showed reasonable agreement in the estimates made by the two methods and there was no indication of a possible bias inherent in either method for estimating DNA concentration. As might be expected however, very low or very high concentrations of DNA exhibited the greatest disagreement between the two methods. Part of the explanation for the variation in estimates could be due to the more subjective nature of estimation using the QB method which directs an analyst to try and match the color intensity of an unknown to one of the twofold dilutions of the control DNA, a process very much like yield gel methods. If an unknown contained a DNA concentration lying in the middle of a two fold range bracketed by the quantitation standards, more variation might be expected in estimating the concentration of that sample. Moreover, unknowns exhibiting either very low or very high intensities of color would be expected to exhibit the greatest variability in concentration estimate in the same way as estimates made from yield gels.

An alternate approach to evaluate the accuracy of the Q-TAT method is to quantify DNA contained within known samples. As a normal component of every Q-TAT assay, a 100 pg aliquot of positive control DNA supplied with Profiler Plus or Identifiler STR typing kits was included as a "quantitation control". Results from 15 separate assays are shown in FIG. 2B. The average Q-TAT estimate of DNA in these assays was 86.2 picograms and the coincidence of variation was about 34%.

Shown in FIG. 3 are DNA concentration comparisons from real time PCR and Q-TAT. As was observed above, both methods produce concentration estimates that agree reasonably well. Interestingly, whereas concentration estimates from QB and Q-TAT exhibited variation that was random demonstrating no obvious bias, real time PCR consistently yielded an estimate that was higher than Q-TAT (FIG. 3).

It is also imperative for any method used for DNA quantitation to be reproducible. The coincidence of variation calculated for repeated measurements of DNA in a total of 10 samples (40 measurements) containing approximately 0.5-1.0 ng/ul using Q-TAT and 7 samples (28 measurements) in the 0.1 ng/ul range was about 35%. This is comparable to the reproducibility exhibited by Quantiblot® technology (not shown).

Discussion

Quality assurance standards upon which audits by ASCLAD-LAB and NFSTC are based mandate the quantitation of human DNA recovered from any evidentiary items subjected to STR analysis in the forensic laboratory. Reasons for the mandate revolve around ensuring the quality of the DNA-STR profiles produced since currently available multiplexes are affected by the quantity of input human DNA template (1-3). Since most items of biological evidence will serve as a growth substrate for micro-organisms, DNA quantitation methods that are not specific for human DNA and will not accurately quantify the amount of human template present in an extract that may also contain non-human DNA. An additional reason to quantify human DNA in an extract relates to the preservation of as much template as possible for repeat testing by another laboratory, should that be requested by the court.

Current methods for quantifying human DNA include slot blot/probe hybridization available currently in the Quantiblot® kit. This technology is one that stands alone in the forensic laboratory, requiring specialized methods and equipment not used for other procedures in a DNA section. Sensitivities for Quantiblot® technology range from approximately 150 picograms to 10 nanograms (package insert from the Quantiblot® kit) which is less sensitive than the Q-TAT technology, but which has a much broader dynamic range.

An approach to quantifying human DNA very similar to Q-TAT was reported by Sifis et al. in 2002 (7). Rather than using fluorescence incorporated into amelogenin amplicons, these authors measured fluorescence incorporated into amplicons amplified from the Alu family of short interspersed repeats. Like the amelogenin locus, the Alu sequences are primate specific thereby making the assay useful for quantifying human DNA. The assay reported by Sifis et al (7) exhibited a useful range of 2.5-100 pg of human genomic DNA. This level of sensitivity is higher than the sensitivity reported here, although the upper limit of DNA that can be estimated is a little higher in the Q-TAT assay. The principle difference between the two assays, and one advantage of Q-TAT, is that the technique quantitates fluorescence in PCR products from the X and Y chromosomes which creates the potential for identifying male:female mixtures of DNA present in extracts from forensic evidence. At a minimum, Q-TAT can suggest a male:female mixture of DNA is present in an extract, and with sufficient validation, it may be possible to use Q-TAT to estimate the relative proportions of male and female DNA in a mixed sample.

A new and rapidly growing technology for the quantitation of human DNA is real time PCR (8,10-12). Primers exist for several loci, including the X and Y chromosome, that make the amplification specific for primate DNA, and the incorporation of intercalating dyes into PCR product at the end of each PCR cycle, or the cleavage of quenched fluors attached to primers through a Taq-man strategy allows for quantitation of product buildup (8,10-12). Sensitivity of real time PCR is better than Q-TAT and the dynamic range is much higher because quantity estimates are in part based upon the slope of the rate of increase in PCR product with each successive round of amplification. Therefore, in amplifications containing a high concentration of DNA template, early rounds of amplification would demonstrate a dramatic rate of increase in PCR product and an accurate estimate of template quantity could be made after early rounds of the cycling program before primers and other reactants become limiting. Q-TAT technology, on the other hand, requires all cycles to be completed before quantitation occurs. For samples with a high concentration of DNA, reactants could become limiting making accurate quantitation impossible. Analysts must therefore examine concentration estimates from extracts demonstrating a high concentration of DNA carefully and perhaps re-quantitate the sample(s) using a dilution series to get an accurate estimate of the DNA present. While this may appear to be a significant limitation of the Q-TAT methodology, in our experience, analysts can incorporate features of an evidentiary sample being extracted into a theoretical estimate of how much DNA will be recovered from that sample and bracket a useful template input initially using several dilutions of the unknown to obtain a reliable estimate of DNA concentration. In fact, a lab may wish to amplify 2-3 dilutions of every unknown as a standard procedure. Amplifying a small dilution series can also reveal the presence of PCR inhibitors in evidentiary samples; the logic being that more diluted samples would reveal the presence of greater amounts DNA than less diluted or undiluted samples in the series.

The Q-TAT, Quantiblot®, and real time PCR quantitation methods all rely on comparing the amount of DNA in an unknown to some well characterized (and quantitated) reference standard. In the case of Q-TAT, a standard curve consisting of fluorescence contained within amelogenin products amplified from different amounts of reference DNA was used to estimate amounts in unknowns. Although the work reported here was performed using a male DNA sample to prepare the standard curve, use of a female reference sample produced comparable concentration estimates as long as the area under both the X and Y products was summed before comparison to the standard curve prepared from female DNA. This is not surprising since single copies of the amelogenin locus reside on the X and Y chromosomes and are amplified with roughly equal efficiency. Hence, the amelogenin locus on the two copies of the X chromosome in a female exhibit molar equivalence to amelogenin loci on the single copy of X and single copy of Y in the male.

The Q-TAT assay may also enable an estimate of male and female DNA in a mixed sample from a sexual assault by plotting on the fluorescence under the Y amplicon with comparison to Y amplicon fluorescence in a standard curve prepared from male DNA. Such validation is planned and would further enhance the utility of Q-TAT as a quantitation tool in a DNA typing laboratory.

Comparison of concentration estimates between real time PCR and Q-TAT indicated a consistently higher estimate made using real time PCR. Likewise, real time PCR consistently produced estimates that are higher on samples also tested using QB methods (not shown). In contrast, comparisons between Q-TAT and QB exhibited a random pattern of variation in concentration estimates among the shared samples. These results may indicate a bias of real time PCR to over estimate human DNA concentrations, or an under estimation bias characteristic of QB and Q-TAT. In this regard, replicate measurements of the positive control supplied with STR typing kits may suggest Q-TAT underestimates DNA quantities. Ultimately, the requirement for any quantitation assay is reliability. If a quantitation method underestimates or overestimates human DNA, the bias can be identified through validation and considered when amplifying a template for STR results. As long as the amount of DNA template amplified reliably produces a DNA profile that is of sufficient quality to interpret, the limitations of the assay used to quantitate DNA in a sample are not so critically important.

REFERENCES FOR EXAMPLE 1

1. The Perkin Elmer Corporation, AmpFlSTR® profiler plus, PCR amplification kit, user's manual. San Jose, Calif.: The Perkin Elmer Corporation, c1998.
2. Applied Biosystems. AmpFlSTR® identifiler PCR amplification kit, user's manual. Foster City, Calif.: Applied Biosystems, c2001.
3. Kline M C, Duewer D L, Redman J W, Butler J M. NIST mixed stain study 3: DNA quantitation accuracy and its influence on short tandem repeat multiplex signal intensity. Anal Chem 2003; 75:2463-2469.
4. Butler J M. Forensic DNA typing. Biology, technology, and genetics of STR markers. 2nd Edition, Burlington, Mass.: Elsevier Academic Press, c2005.
5. DNA Advisory Board, Federal Bureau of Investigation. Quality assurance standards for forensic DNA testing laboratories. Washington, D.C.: Federal Bureau of Investigation, c2000. Accessible at: http://www.fbi.gov/hq/lab/fsc/backissu/july2000/codis2a.htm#Introduction.
6. Singer V L, Jones L J, Yue S T, Haugland R P. Characterization of PicoGreen reagent and development of a fluorescent-based solution assay for double stranded DNA quantitation. Anal Biochem 1997; 249:228-238.
7. Walsh P, Varlaro J, Reynolds R. A rapid chemiluminescent method for quantitation of human DNA. Nucl Acids Res 1003; 20:5061-5065.
8. Nicklas J A, Buel E. Development of an Alu based, real-time PCR method for quantitation of human DNA in forensic samples. J Forensic Sci 2003; 48:936-944.
9. Sifis M E, Both K, Burgoyne L. A. A more sensitive method for the quantitation of genomic DNA by Alu amplification. J Forensic Sci 2002; 47:589-592.
10. Nicklas J A, Buel E. Development of an Alu based, QSY7-labeled primer PCR method for quantitation of human DNA in forensic samples. J Forensic Sci 2003; 48:282-291.
11. Alonso A., Marten P, Albarran C, Garcia P, Garcia O, Fernandez de Simon L. Real-time PCR designs to estimate nuclear and mitochondrial DNA copy number in forensic and ancient DNA studies. For Sci Int'l 2004; 139:141-149.
12. Walker J A, Kilroy G E, Xing J, Shewale J, Sinha S K, Batzer M A. Human DNA quantitation using Alu element based polymerase chain reaction. Anal Biochem 2003; 315:122-128.
13. Andreasson H, Gyllensten U, Allen M. Real-time PCR quantification of nuclear and mitochondrial DNA in forensic analysis. Biotechniques 2002; 33:402-411.
14. Maniatis T, Fritsch E. F., Sambrook J. Molecular cloning: A laboratory manual. Cold Spring Harbor, N.Y.: Cold Spring Harbor Laboratory, c1982.
15. Miller S A, Dykes D D, Polesky H F. A simple salting out procedure for extracting DNA from human nucleated cells. Nucl Acids Res 1988; 16:1215.
16. Micka K A, Amiott E A, Hockenberry T L, Sprecher C J, Lius A M, Rabbach D R. TWGDAM validation of a nine-locus and a four-locus fluorescent STR multiplex system. J Forensic Sci 1999; 44:1243-1257.
17. Morrison C, Gannon J. The impact of the PCR plateau phase on quantitative PCR. Biochim Biophys Acta 1994; 121:493-498.

EXAMPLE 2

Q-ACE Total Human and Male-Only DNA Quantitation Procedure: Combined Q-TAT and Capillary Electrophoresis The procedure that follows has been developmentally validated and internally validated by the Tulsa Police Department Forensic Laboratory Biology Section.

Background Information:

Knowing the approximate human DNA concentration within extracted forensic evidence samples facilitates successful DNA amplification for the purpose of forensic DNA profiling and is mandated by Standard 9.4 of the QAS (Quality Assurance manual). This requirement stems from the fact that forensic DNA evidence is generally of an extremely limited nature and that, whenever possible, at least half of this limited sample should be retained for future re-testing. Accurate quantification methods performed pre-DNA profiling help to ensure that optimal DNA profiling results will be obtained within one round of testing and that the maximum amount of evidence will remain for further testing. The Biology Section uses a sex-typing PCR-based multiplex described in Example 1 as Quantitative Template Amplification Technology (Q-TAT). This Examples describes quantitative analysis of the Q-TAT multiplex using capillary electrophoresis (CE). This combined methodology is referred to as Quantitative Amplification through Capillary Electrophoresis (Q-ACE). The Q-ACE method allows for picogram (pg) (one-trillionth of a gram) amounts of human DNA to be quantified by use of DNA-specific primers to the human X and/or Y chromosomes. A set of additional primers allows the amplification of an internal positive control (IPC). The following targets are amplified:

TABLE 1

Amplified targets.

| Target | Target information | Location | Amplicon size in bases | approximate size migration after addition of FAM dye tag on reverse primer only |
|---|---|---|---|---|
| SRY | sex-determining region Y gene | Yp11.3 | 111 | 109 |
| IPC | the pRL null plasmid from *Renilla luciferase* (sea pansy) | | 203 | 200 |
| X | amelogenin X | Xp22.31-p22.1 | 212 | 209 |
| Y | amelogenin Y | Yp11.2 | 218 | 216 |

The dynamic range of quantitative fluorescent detection by a CE device is measured in relative fluorescent units (RFU). RFU, for the purpose of this procedure, is expressed as a peak height value. The linear range for quantitative CE is from about 150RFU to approximately 6000RFU. These detected RFU values are representative of an amount of fluor-labeled DNA product passing the detector. Although the actual amount of DNA passing by the detector is unknown, but the amount of DNA pre-amplification (and pre-CE analysis) can be known for standard samples. When observing the detected RFU values of a standard curve made from a known quantity of female or male standard DNA, we have determined that the amount of DNA pre-amplification in a sample is directly proportional ($R^2=1$) to the detected peak height RFU of this sample during CE detection. Based upon this proportional relationship, the CE quantitative linear range stated above as 150RFU to 6000RFU has been determined to correspond to a pre-amplification DNA amount of between 35 pg to 700 pg. However, this range will fluctuate for every CE device because each device has different detectors with differing dynamic ranges of detection. With this knowledge, the amount of DNA in an unknown sample can be directly determined from the observed peak height of that sample collected during QCE.

Above 500-700 pg DNA, the fluorescence levels may become so great that the detector is overwhelmed. This level of fluorescence is known as the limit of linearity (LOL) of the device's detector. Thus, >700 pg DNA cannot be accurately quantified in undiluted form by a CE device. However, one can re-amplify unknown samples exhibiting >700 pg of DNA in a diluted form and then determine the fluorescence of the post-amplification DNA sample. When coupled with the ability to dilute an unknown DNA sample, CE detection has a dynamic quantitative range of 0.063 ng/uL to unlimited ng/uL.

INSTRUMENTATION: Pipetman P-1000, P-200, P-100, P-20, P-10, USA Scientific Mini-Fuge Centrifuge, ABI Prism 310 Genetic Analyzer and its ancillary equipment, Labconco Protector Fume Hood, Millipore Elix-S Purification System, Millipore Milli-Q Purification System, Compact Refrigerator, Compact Freezer, Napco 8000-DSE Autoclave, ABI 9700 thermal cycler, Temperature Verification Kit, Mini-Max II vortexer, an ABI Apple-based or PC-based GeneScan or GeneMapperID software.

Reagent Preparation:
Purchased Solutions:
pRL null vector (purchased from Promega Part #E2271)
2×Go-Taq Colorless DNA polymerase mixture (purchased from Promega Part #M7133)
National Institute of Standards and Technology Standard Reference Material (NIST SRM) 2372 human DNA quantitation standards (purchased from NIST)
FAM dye labeled primers (purchased from Invitrogen) as depicted in Table 2.

TABLE 2

FAM dye labeled primers

| Primer name | Sequence | SEQ ID NO: |
|---|---|---|
| AMEL forward | 5'-ACC TCA TCC TGG GCA CCC TGG-3' | 1 |
| AMEL reverse FAM | 5'-AGG CTT GAG GCC AAC CAT CAG-3'<br>3'-TCC GAA CTC CGG TTG GTA GTC-5' | 2 |
| SRY forward | 5'-ACG AAA GCC ACA CAC TCA AGA AT-3' | 3 |
| SRY reverse FAM | 5'-CTA CAG CTT TGT CCA GTG GC-3'<br>3'-GAT GTC GAA ACA GGT CAC CG-5' | 4 |
| pRL forward | 5'-AAG GTG GTA AAC CTG ACG TTG-3' | 5 |
| pRL reverse FAM | 5'-TTC ATC AGG TGC ATC TTC TTG-3'<br>3'-AAG TAG TCC ACG TAG AAG AAC-5' | 6 |

Lab-Generated Solutions:
A NIST female DNA dilution series; 2) A NIST male DNA dilution series 3) Sterile dH$_2$O Procedure for Preparing the Q-ACE Three Primer Mix:
When the six primers (3 primer pair sets) are received from Invitrogen, they will be combined into primer pair sets in the lab. Q-ACE Three Primer Mix Worksheet must be filled out for this procedure. Such a worksheet should include at least the following entries related to the primers: name, nmole amount, status, μl needed for 100×, final total of μl of primer pair, and number of 1 and/or 10 μl aliquots. In addition, the worksheet should contain the date, analyst initials, and lot number(s) of buffer(s) used. Record the nmole amount of dried primer in each primer tube from the packing slips. Staple these slips to the back of the worksheet.

Prepare the Q-ACE three primer master mix as per worksheet instructions, reproduced below. Log the information into the chemical inventory. The Q-ACE three primer mix must contain a final concentration of 10× amelogenin primer set, 10×SRY primer set, and 1×pRL primer set in sterile dH$_2$O.

Instructions for Preparation of Q-ACE Three Primer Master Mix

Record nmole amount for each primer. Calculate how many μl of liquid is needed to rehydrate a 100× solution of that primer. NOTE: If 53.8 nmoles of dried primer has been received, then you would add 538 µl of liquid to that primer to rehydrate 100× solution of that primer). Record the µl of liquid needed above. Determine which primer in each pairing has been received in the largest nmole quantity and in the smallest nmole quantity. Record a star for the largest one of each pair in the "status" column. Begin primer rehydration by making a 100× solution out of the "largest" primer in the pair using TE Buffer. Mix this solution very well. Now use this single primer solution instead of TE Buffer to rehydrate the "smallest" primer in the pair at 100×. In this way, both primers in a pair are resuspended at 100× together and this procedure makes a 100× solution of each primer pair. Record the final volume of each 100× primer pair in the appropriate row above. Now, use the 100× primer pairs to make as much TPM as possible. For every 100 µl of TPM, you must mix 100 µl of 100×AMEL primer set +10 µl of 100×SRY primer set +1 µl of 100×pRL primer set +79 µl dH$_2$O. Determine how much total TPM can be made from the primer sets above to completely consume the primer sets if the AMEL or SRY is the limiting primer set. Make the TPM in bulk and record the TPM lot number (six-digit date plus three letter initials) on the worksheet. Dispense the TPM into 300 µl aliquots and store frozen at −20° C. in a labeled tube rack. Use only one aliquot at a time. The aliquot in use can be thawed and stored at 4° C. until consumed. Place the worksheet in a Chemical Logbook Binder. The worksheet acts as a CHEMICAL LOGBOOK SHEET for the primers, primerpairs, and the TPM used in the Q-ACE procedure.

Procedure for Making a NIST Standard Dilution Series:

Label six microcentrifuge tubes A-1000 pg/µL, A-500 pg/µL, A-250 pg/µL, A-125 pg/µL, A-63 pg/µL, and A-32 pg/µL. Label six microcentrifuge tubes B1000 pg/µL, B 500 pg/µL, B-250 pg/µL, B-125 pg/µL, B-63 pg/µL, and B-32 pg/µL. Determine the nanogram amount (#) of male DNA per µL residing in the NIST A Standard tube. Add 1 µL of the NIST A Standard DNA to the A-1000 pg/µL tube and then add (#)-1 µL of sterile dH$_2$O to the A-1000 pg/µL tube. Add 25 µL of sterile dH$_2$O to the rest of the A-series tubes. Add 25 µL of tube A-1000 pg/µL solution to tube A-500 pg/µL to make 50 µL of a 500 pg/µL NIST A DNA solution. Add 25 µL of tube A-500 pg/µL solution to tube A-250 pg/µL to make 50 µL of a 250 pg/µL NIST A DNA solution. Add 25 µL of tube A-250 pg/µL solution to tube A-125 pg/µL to make 50 µL of a 125 pg/µL NIST A DNA solution. Add 25 µL of tube A-125 pg/µL solution to tube A-63 pg/µL to make 50 µL of a 63 pg/µL NIST A DNA solution. Add 25 µL of tube A-63 pg/µL solution to tube A-32 pg/µL to make 50 µL of a 32 pg/µL NIST A DNA solution. Make the NIST B DNA Dilution Series similarly.

Procedure for Making a Female and Male NIST Standard Curve for a Particular 310 CE Device:

Step 1: Record all information for this procedure onto a Q-ACE Amp Set-up and 310 Set-up Worksheet. Prepare the Q-ACE master mix. The recipe for this master mix is on the Q-ACE Amplification Set-Up Worksheet. The Q-ACE master mix in its final form must contain 1.2×DNA polymerase and buffer.

Step 2: Label thirteen total GeneAmp PCR tubes according to the worksheet. Six tubes must be labeled for each NIST A Serial Dilution and six tubes must be labeled for each NIST B Serial Dilution. One Q-ACE negative control blank tube must be labeled.

Step 3: Add 11.5 µl of appropriate master mix to each tube.

Step 4: Add 1 µl of each of the NIST A and B dilutions to the appropriate amp tube.

Step 5: A Q-ACE negative control blank tube must be made by adding 1 µL sterile dH$_2$O to the appropriate amp tube.

Step 6: Make sure the worksheet is completely filled out. Place the GeneAmp PCR tubes into the thermal cycler. Run the Q-ACE amplification cycle with the following sub-parts:

TABLE 3

| Q-ACE amplification cycle | | |
|---|---|---|
| Sub-program Type | Temperature | Time |
| CYCLE (30) | 98° C. | 10 sec |
|  | 55° C. | 60 sec |
|  | 72° C. | 30 sec |
| HOLD | 60° C. | 10 min |
| HOLD | 25° C. | ∞ |

Step 7: After amplification, prepare each sample for 310 analysis by following the 310 analysis procedure for Q-ACE samples on the worksheet. Include a 310 blank (see the "ABI Prism 310 Genetic Analyzer Capillary Electrophoresis Procedure"). No allelic ladder is needed for Q-ACE. Because the amplified products are labeled with the blue FAM dye, you may click only for LIZ-orange and FAM-blue to be collected on the five-dye sample sheet. Fill in Q-ACE sample tracking numbers. Make an injection list from the sample sheet. Make sure the sample sheet and injection list contain "Q-ACE" in the title and identify the particular 310 instrument in the title. Make sure that the run-time parameters are changed so that electrophoresis is 21 minutes. This reflects the minimum time it takes for Q-ACE peak data to be collected. Observe, record, and analyze data using 310 ABI Prism Collection Software version 2.1, GeneScan Analysis 3.1.2 Software, and the "Q-ACEfiler" genotyping macro, lovingly handcrafted by Jonathan P. Wilson. Print out the Q-ACEfiler EP's.

Step 8: Plot the Q-ACEfiler RFU data on a Q-ACE Standard Curve excel worksheet. A female standard curve must be plotted when estimating the amount of total human DNA needed for successful genomic DNA profiling (ie. Identfiler profiling). A female standard curve must be made by plotting the Amelogenin X amplicon fluorescence values against the corresponding known NIST B pg amount in each tube pre-amplification.

Step 9: Store the Standard Curve as an excel file named "MMDDYY-FML-(old/new)310-(male or female)". When Q-ACE data is gathered from unknown DNA samples using a 310 CE device, the pg DNA amount in those unknown samples must be calculated using a standard curve generated from the very same 310 CE device. The standard curves will be specific to each 310 device. Note that some 310 devices have a more or less sensitive dynamic range of RFU detection than other 310 devices (each CCD detector is different). To compensate for a lower LOL in some CE devices, the injection time for the standard curve samples and the unknown samples can be decreased from 5 seconds down to one second. The data gathered at an initial 5-second injection time will allow the analyst to decide if subsequent data must be gathered at a decreased injection time. Whatever the outcome, the injection time used to generate the standard curve for that CE device must be the same as the injection time used to calculated the DNA content of unknown samples for that standard curve on that specific CE device.

CONTROL RESULTS FOR STANDARD CURVES: Check the accuracy and precision of a male or female standard curve CONTROL RESULTS below) by the following conditions:

$R^2$ value of the line of regression must be between 0.97 and 1.00 the line of regression must have a slope that causes the Y-intercept value to fall below 150 RFU when the Limit of Quantification (LOQ) for the CE instrument (also referred to as the minimum interpretation threshold "MIT") is theoretically plugged in as 150 RFU, the test pg amount calculated using the standard curve must approach 35 but never exceed 35.

when the Limit of Detection (LOD) for the CE instrument (also referred to as the peak amplitude threshold "PAT") is theoretically plugged in as 50 RFU, the test pg amount calculated using the standard curve must not exceed 0.

A female standard curve must be calculated from the NIST B female DNA dilution series using the Amelogenin "X" amplicon's RFU values. The female standard curve must be used to calculate the amount of DNA in an unknown sample for later amplification using a genomic DNA profiling kit (ie. identifiler, Minifiler, Profiler, COfiler, etc.) A male standard curve must be calculated from the NIST A male DNA dilution series using the SRY amplicon's RFU values. The male standard curve must be used to calculate the amount of DNA in an unknown sample for later amplification using a male haplotype DNA profiling kit (ie. Yfiler). A new standard curve will have to be generated at least once a year or after any incidence of maintenance or use of a new matrix for that instrument. Procedure for Estimating the Amount of Total Human or Human Male-Only DNA in an Unknown Sample for a Particular 310 CE Device:

Step 1: Record all information for this procedure onto a Q-ACE Amp Set-up and 310 Set-up Worksheet. Prepare the Q-ACE master mix. The recipe for this master mix is on the Q-ACE Amplification Set-Up Worksheet. The Q-ACE master mix in its final form must contain 1.2×DNA polymerase and buffer.

Step 2: Label GeneAmp PCR tubes according to the worksheet. Tubes must be labeled for the NIST A 250 pg/μL Serial Dilution, the NIST B 250 pg/μL Serial Dilution, and one Q-ACE negative control blank.

Step 3: Add 11.5 μl of appropriate master mix to each tube.

Step 4: Add 1 μl of each of the NIST A 250 pg/μL male positive control sample, NIST B 250 pg/μL female positive control sample dilutions to the appropriate amp tubes.

Step 5: Make the Q-ACE negative control blank tube by adding 1 uL sterile dH2O to the appropriate amp tube.

Step 6: Make the Q-ACE samples to be quantified by adding 1 μL of the appropriate unquantified sample to the appropriate amp tube.

Step 7: Make sure the worksheet is completely filled out. Place the GeneAmp PCR tubes into the thermal cycler. Run the Q-ACE amplification cycle with the following sub-parts:

TABLE 4

Q-ACE amplification cycle

| Sub-program Type | Temperature | Time |
| --- | --- | --- |
| CYCLE (30) | 98° C. | 10 sec |
| | 55° C. | 60 sec |
| | 72° C. | 30 sec |
| HOLD | 60° C. | 10 min |
| HOLD | 25° C. | ∞ |

Step 8: After amplification, prepare each sample for 310 analysis by following the 310 analysis procedure for Q-ACE samples on the worksheet, including a 310/CE blank (see the "ABI Prism 310 Genetic Analyzer Capillary Electrophoresis Procedure"). No allelic ladder is needed for Q-ACE. Because the amplified products are labeled with the blue FAM dye, you may click only for LIZ-orange and FAM-blue to be collected on the five-dye sample sheet. Fill in Q-ACE sample tracking numbers. Make an injection list from the sample sheet. Make sure the sample sheet and injection list contain "Q-ACE" in the title and identify the particular 310 instrument in the title. Make sure that the run-time parameters are changed so that electrophoresis is 21 minutes. This reflects the minimum time it takes for Q-ACE peak data to be collected. Make sure that a female and/or male standard curve is available for the CE instrument used. Make sure that the samples are injected for the same time as the injection time used to generate the standards curve. Observe, record, and analyze data using 310 ABI Prism Collection Software version 2.1, GeneScan Analysis 3.1.2 Software, and the "Q-ACEfiler" genotyping macro. Print out the Q-ACEfiler EP's.

Step 9: Plot the Q-ACEfiler RFU data for the unknown samples on a Q-ACE Standard Curve excel worksheet. The appropriate female standard curve data must be used to estimate the amount of total human DNA needed for successful genomic DNA profiling (i.e. Identfiler or Minifiler profiling). The appropriate male standard curve data must be used to estimate the amount of human male-only DNA needed for successful male haplotype DNA profiling (i.e. Yfiler profiling). The worksheet auto-populates the estimated DNA amounts in the unknown samples. The Q-ACE female and male estimated pg/μL value is within a range of pg/μL values that have been determined to be less than a % CV of 30. Peaks must be apparent in the NIST-traceable female and NIST-traceable male Q-ACE positive controls for all relevant amplicons in the QTAT assay as described in the Table in the Background Information section of this procedure. Inform and consult the Biology Section Technical Leader if these conditions are not met or if concerns about the male DNA control arise. The negative QTAT control (blank) should only have an IPC peak present. See Appendix for how acceptable QTAT controls should appear.

Step 10: Print out the appropriate completed Q-ACE Standard Curve worksheet(s) to include in the casefile. Once printed, the data does not need to be stored electronically.

Step 11: Print out the appropriate completed Q-ACE Standard Curve worksheet(s) to include in the casefile. Once printed, the data does not need to be stored electronically.

Important Testing Considerations:

During developmental validation we determined that the % CV for any particular CE device's electrophoretic injection and fluorophore detection is achievable at less than 1% if the instrument is carefully set-up. The integrity of the closed system for electrophoresis (i.e. the "block") is the most critical factor in keeping the % CV low for the CE instrument. If the "block" is more than two to three days old or has had a buffer change without a capillary change, the % CV can increase to over 10%. Once an instrument is set up, the buffer that originally has circulated through the polymer in the system should not be changed or re-hydrated until quantitative CE (QCE) data is completely gathered. The "block" can be re-hydrated or rejuvenated according to each laboratory's own policies regarding qualitative DNA analysis (i.e. regular allele size-typing). We have demonstrated that QCE is sensitive to "block integrity", whereas qualitative CE used to size-profile alleles is not (not shown).

During developmental validation the % CV for pipetting and dilution was determined to be less than 1%. Using a pipetting device to measure out less than 1 μl of liquid is not acceptable, due to the limitations of the pipetting device. This is why the dilution schemes and recipes are laid out the way they are. Pipetting less than 1 μl of liquid will raise the % CV above 1%.

If a Q-ACE sample has truncated peaks in the null dilution and truncated peaks in the ½5th dilution, then too large of an original sample has been taken. For example, a DNA extract with QTAT-QCE value of 20 ng/μl means that enough DNA to run 20 separate DNA amplifications was isolated in this sample. In theory, this would mean that at least 20 times more evidence or original sample was consumed than was necessary to obtain a DNA profile. If a sample has more DNA than this, it is considered wasteful. The analyst should, at this point, make an effort to better estimate the density of the original cell content of the sample being tested so that samples this concentrated are not routinely isolated. Consult with the Biology Section Technical Leader to improve proper sample size estimation. If it does occur, however, that a sample has Q-ACE results greater than 20 ng, then it is acceptable for the analyst to dilute that sample more and then repeat quantitation.

Special handling needs are required for Hi-Di formamide. Opened Hi-Di formamide is to be kept in lab three. Formamide may act as a potential teratogen when inhaled or absorbed into the skin. All analyzed samples, tubes, and pipette tips containing formamide waste are to be placed into 50-ml Falcon tubes for disposal into the biohazardous waste receptacles. In this way, formamide vapor/fumes are minimized.

The use of refrigerated instead of frozen Hi-Di formamide was developmentally validated for the Q-ACE procedure without any adverse effect on data quality.

CONCLUSION: Use of the foregoing protocols resulted in rapid, accurate, reliable determination of the quantity, quality, gender of origin and presence or absence of PCR inhibitors for all samples tested.

EXAMPLE 3

A method for simultaneously quantifying the amounts of human and male-only DNA within a sample by amplification of that sample with fluorophore-tagged human-specific DNA primers was described in Example 1 (1). Post-amplification, the fluorescent peak heights of the products of amplification can be quantified using capillary electrophoresis with fluorescent detection. Amounts of peak height fluorescence can then be used to determine the amount of DNA residing in an unknown sample pre-amplification by comparison to a standard curve of peak height fluorescence created from the amplification of DNA solutions of known quantity (1). Because this method employs the amplification of gender-specific amplicons, the DNA quantity, gender, and/or relative amount of male and total human DNA can be simultaneously determined from 1 μl of any unknown DNA sample. In this study, we present the developmental validation of an improved multiplex version of the original assay that incorporates two more amplicons. The improved assay continues to accurately quantify total human and male-only DNA in samples while demonstrating increased sensitivity for detecting male DNA within forensic mixtures. These improvements result in an assay that can simultaneously gender-type and quantify the male and total human DNA content of forensic unknown samples using only amplification and capillary electrophoresis with fluorescent detection.

Introduction

Human DNA quantification is now a mandatory requirement for all forensic laboratories within the United States that perform DNA-typing of human DNA samples from criminal evidence (2). This requirement stems from the fact that forensic DNA evidence is generally of an extremely limited nature and that, whenever possible, at least half of this limited sample should be retained for future re-testing. Accurate quantification methods performed pre-DNA profiling help to ensure that optimal DNA profiling results will be obtained within one round of testing and that the maximum amount of evidence will remain for further testing or future re-testing. As a result of the limited nature of forensic DNA evidence, many DNA quantification methods have recently arisen, evolved, and changed in order to provide additional information beyond a mere estimation of DNA concentration. Ideal forensic DNA quantification methods should be human-specific so that DNA profiling will not be attempted on non-human DNA samples. Ideal forensic DNA quantification methods should be very sensitive and also provide information concerning levels of chemical inhibitors or DNA degradation that may be present in a forensic sample. Non-human-specific DNA quantification methods like spectrophotometry or fluorometry are no longer widely considered able to provide enough information because they are not human specific. Although the yield gel can provide information concerning DNA degradation, its level of sensitivity and its inability to provide any other specific information overshadows the information it does provide about DNA samples. Quantitative DNA hybridization techniques have been able to provide human specificity and a greater level of sensitivity, but have not been able to provide information concerning inhibition or degradation, which may explain the demise of one quantitative DNA hybridization method utilized by many forensic DNA laboratories, QuantiBlot® (Applied Biosystems, Foster City, Calif.). Quantification methods employing qPCR with DNA concentration estimates made either real-time (3-7) or post-amplification (1, 8) can provide human specificity, sensitivity, and information regarding degradation and inhibition. The ability to detect the presence of chemical inhibitors in a forensic DNA sample is invaluable in that it allows steps to be taken to further purify the DNA sample before DNA profiling is attempted. Varying methods of real-time qPCR can provide this information as well as more information concerning the gender or mixture status of the human DNA within some samples. But, until recently, separate tests had to be performed to obtain total human quantification information and then male-only quantification information. The introduction of flourophore-quenching technology (9) to qPCR technology has recently overcome the need for separate tests for gender and mixture assessment during DNA quantification by making it possible to multiplex during real time qPCR. Recently, the Plexor™ HY qPCR System (Promega Corporation, Madison, Wis.) became the first commercially available real-time qPCR system capable of simultaneously quantifying total human and male-only DNA within a DNA sample. It also follows that ideal quantification methods should decrease the time of analysis, increase the ease of analysis by being amenable to the current trend towards the automation of forensic DNA analysis, and even decrease the cost of analysis. Finally, the most ideal DNA quantification method would provide one more level of information to the forensic DNA analyst—the ability to direct DNA profiling by predicting the success or the futility of various types of DNA profiling options. Several quantification methods exist that can inform the analyst about the male DNA content of a forensic sample (10, 11, 12). Whether the information is obtained within one or two rounds of testing, the information provided by the use of primers specific to the X and/or Y chromosomal material within human DNA samples during quantification can generate information that may greatly facilitate an analyst's decision to proceed with genomic DNA-profiling or male-only DNA profiling (13). Knowing gender-specific information about a sexual assault sample, for instance, would allow the analyst to be able to reasonably expect that a Y-chromosomal specific DNA profiling procedure would yield successful results on this sample. However, a quantification method that could let the analyst know that a forensic sample does not contain enough male DNA for successful profiling with the detection sensitivities currently available in varying DNA testing kits would be even more valuable. Information of this nature would allow an analyst to stop further analysis on that sample, thus saving the time and resources most analysts now spend on attempting DNA profiling techniques on samples that, with current technology, will not yield case-solving DNA profiling results.

A post-amplification qPCR assay which was referred to as Q-TAT (quantitative template amplification technology) was described in Example 1 (1). This assay (which we refer to here as the original assay) quantifies the amount of human and male-only DNA in a sample by amplification of the Amelogenin locus on the X and Y chromosomes by the use of fluorophore-tagged human-specific DNA primers (1). Post-amplification, the peak height of the resulting 212-basepair X-amplicon and the 216-basepair Y-amplicon (if present) is quantitatively analyzed by determining the relative fluorescence peak height of each amplicon using a capillary electrophoresis device coupled with fluorescent detection (CEFD). The peak height fluorescence of the X amplicon or the X and Y amplicons can then determine the amount of DNA residing in the unknown sample pre-amplification by comparison to a standard curve of peak height fluorescence gathered from a standard dilution of a male or a female DNA sample of known quantity (1). Because this method amplifies the X amplicon or the X and Y amplicons of the Amelogenin locus, the gender or mixture status of the unknown DNA sample can be determined at the same time as the relative amounts of Y-chromosomal material (the amount of Y amplicon fluorescence) and relative amounts of total human chromosomal material (the amount of X amplicon fluorescence plus the amount of Y amplicon fluorescence) are determined. This information can be obtained by the consumption of only 1 µl of any unknown DNA sample. In this study, we present the developmental validation of an improved multiplex version of the original assay.

We developmentally validated an improved multiplex assay based upon the original assay (1) in our laboratory by necessity. Prior to our decision to try to implement the original assay, we were using the QuantiBlot® method supplied by Applied Biosystems to meet the quantification standard. When Applied Biosystems announced that it would be discontinuing the QuantiBlot® Kit, the prospect of performing a developmental validation on this method for use in the Tulsa Police Department Forensic Lab Biology Section suddenly seemed less daunting. By April of 2007, we decided that the advantages of the original assay would be worth the time and potential expense of developmental validation. In summary, the original assay's advantages were as follows. The original assay could provide simultaneous quantification information concerning the total human DNA in an unknown sample as well as the Y-only DNA in an unknown sample. No other method at the time could do this. Currently, the only commercially-available quantification method able to perform simultaneous total human and Y-only information is the Plexor™ HY qPCR System (Promega Corporation, Madison, Wis.) released in August of 2007 (11). The original assay required no additional technology other than that needed for human DNA profiling. In other words, it only required basic polymerase chain reaction (PCR) and the ability to analyze the amplification products using CEFD. All other quantification methods, to date, require the mastery of technologies other than basic PCR and CEFD only. PCR and CEFD are already required for the DNA profiling step, so no new equipment or supplies would be needed. Because no new equipment or supplies would be needed to implement this quantification method, the time involved in general quality assurance practices and quality control activities would dramatically decrease. In other words, all of the ancillary consumable supplies and reagents would not be purchased or generated for this method and therefore would not need to be tracked, logged, and handled according to stringent national quality assurance standards. And, finally, it appeared that this assay would be easily amenable to automation.

The original assay did, however, have some distinct disadvantages that would have to be overcome before our laboratory could use the procedure on actual casework. The following disadvantages would have to be addressed by our developmental validation. The original assay as published had a coefficient of variation (CV) of about thirty percent that was not characterized or understood. The original assay, as published, relied heavily upon sample analysis using CEFD, but the effect of the dynamic range of the CEFD device on the reported quantification values had not been addressed. These effects would need to be completely determined and controlled for prior to using the assay on actual casework. The effect of utilizing differing CEFD devices had not been evaluated and the generation of standard curve data was not standardized. The original assay could not detect the presence of PCR inhibitors nor could it provide accurate gender-typing or Y-only quantification values if the Amelogenin Y template present in a sample DNA extract had a primer-binding site mutation sufficient to stop primer annealing. And finally, once the original assay contained the multiplex of additional primers required for the detection of inhibition and the fail-safe ability to detect male DNA in a sample, the original amplification parameters would need to be optimized for the improved multiplex assay.

The developmental validation of an improved multiplex assay presented here has resulted in an improved multiplex assay that has overcome all of the disadvantages of the original assay. The original assay (1) has been modified to include two additional fluorophore-tagged primer sets and a non-human DNA target. One of the added primer sets flanks the SRY gene (14,15) which maps to the human Y-chromosome Yp11.3 (12,16). The single 111-basepair amplicon resulting from amplification with this primer set allows for two major improvements in the original assay. 1-2% of males have mutations in the Y-chromosomal Amelogenin gene (17). In certain males, the original assay may not exhibit a detectable Amelogenin Y amplicon. Together, the Amelogenin Y and SRY amplicons provide redundant indicators of "maleness", thus controlling for male primer-binding mutations at a greater level than the original assay. Furthermore, the addition of the SRY primer set dramatically increases the sensitivity of detection of male DNA in unknown samples. The Amelogenin primer set from the original assay amplifies a diploid DNA target. In females, this target is homozygous (X, X) and in males this target is heterozygous (X, Y). The SRY primer set in the improved assay amplifies a haploid target only in males. Because there is no homologue to SRY on the X chromosome, the SRY target has less chance of stochastic "dropout" during amplification in the presence of female DNA. As a result, the Amelogenin amplicons in a mixture are better predictors of genomic DNA profiling success, while the SRY amplicon is a better predictor of DNA haplotype profiling success. The other added primer set amplifies a 200-basepair region of the non-human DNA template that we have added to the original assay. The non-human DNA template and its primer set act as an internal positive control (IPC) for successful DNA amplification. If the non-human DNA template is not amplified and a 200-nucleotide long amplicon is not visualized in the questioned DNA sample post-amplification, then chemical inhibitors are suspected to be present in the questioned sample. The sample can be further purified or diluted and re-quantified prior to attempting DNA profiling on that sample. The non-human DNA template consists of the commercially available plasmid (the pRL-null vector from Promega Corporation, Madison, Wis.) from the marine organism *Renilla rentiformis* (a coelenterate known as the sea pansy). The plasmid, containing the 200 base pair amplicon that the additional primer set was designed to amplify, was selected because of its expected scarceness at crime scenes.

Materials and Methods
DNA Extraction

When necessary, DNA was extracted from sample material by one of two methods. One method employed a treatment with a solution containing 2% SDS, 20 µg/µL Proteinase K, 10 mM Tris-Cl (pH 8.0), 1 mM EDTA, and 0.2 M NaCl. Samples were incubated in this solution at 56° C. for at least 1 hour and then extracted with DNA-grade phenol:chloroform:isoamyl alcohol (25:24:1) (Sigma-Aldrich, St. Louis, Mo.). DNA was purified, concentrated, and de-salted using a Centricon device (Millipore Corporation, Billerica, Mass.). The other DNA extraction method employed the DNA IQ™ System with Differex™ or Tissue and Hair Extraction Kit pre-treatment kits, as necessary (Promega Corporation, Madison, Wis.). Extracted and purified DNA was stored at −20° C.

Analyzed DNA Samples

The NIST Standard Reference Material® (SRM) 2372 Human DNA Quantitation Standard was utilized in this study. The NIST SRM 2372 Standard contains three standard samples (13). We utilized two of the standard samples to generate standard curves and verify the accuracy of the improved multiplex assay. The NIST SRM 2372 Standard A is an all-male DNA sample containing 52.4 ng/µl DNA. The NIST SRM 2372 Standard B is an all-female DNA sample containing 53.6 ng/µl DNA. In all instances in which a standard curve was generated, the DNA Standard solution was diluted in such a way as to generate a series of six DNA solutions containing 1000 pg/µl, 500 pg/µl, 250 pg/µl, 125 pg/µl, 63 pg/µl, and 32 pg/µl of DNA material. All dilutions were prepared using sterile deionized $H_2O$ from a Millipore Elix and Milli-Q water system (Millipore Corporation, Billerica, Mass.). The QuantiBlot® Standard A DNA, which is 9947A female DNA containing DNA at a concentration of 2 ng/µl was purchased from Applied Biosystems (Foster City, Calif.) as part of a QuantiBlot® Kit. This sample was utilized in this study as a pure female mock DNA evidence sample. A human NIST-traceable male DNA sample from our laboratory was utilized in this study as a pure male mock DNA evidence sample. This male DNA sample was extracted in our lab from a 1.5 mm punch of a bloodstained FTA® Card (Whatmann, Incorporated, Florham Park, N.J.) and then its DNA concentration was quantified by the QuantiBlot® method as approximately 1 ng/µl. In all instances in which a standard dilution series of these pure samples was generated, the two DNA standard solutions were diluted in a series of halves as ½, ¼, ⅛, 1/16, 1/32, and so on. All dilutions were prepared using sterile deionized $H_2O$ from a Millipore Elix and Milli-Q water system (Millipore Corporation, Billerica, Mass.). The non-human primate samples were prepared from liquid blood draws that were then spotted onto an FTA® Card (Whatmann, Incorporated, Florham Park, NJ) and graciously provided to us by the Tulsa Zoo and Living Museum in Tulsa, Okla. All other DNA samples used in this study were prepared from materials available to us in our laboratory.

DNase I Digestions

The NIST SRM Standard A male DNA sample was diluted to 1000 pg/µl. Aliquots of this solution were combined with a volume of RNase-free DNase I (1 U/µl) (Promega Corp., Madison, Wis.) so that the final concentration of DNase I was 0.004 U/µl in a total volume of 157 µl. The final reaction mix was immediately aliquoted into nine separate tubes that were allowed to incubate for zero, one, two, three, four, five, fifteen, thirty, and sixty minutes. At the end of the incubation period, the appropriate amount of Stop Buffer (Promega Corp., Madison, Wis.) was added to each tube and the tube was heated at 65° C. for 10 minutes to halt enzyme activity. 1 µl of these digests were amplified with the improved multiplex assay and analyzed by CEFD.

EDTA Treatment

A volume of the NIST SRM Standard A male DNA sample was mixed with a volume of 0.5 M EDTA solution to make eleven mixtures containing 1000 pg/µL DNA in increasing final milli-molar amounts of EDTA per µL. The mixtures were constructed so that the addition of 1 µL to the improved multiplex amplification reaction would give a final amplification reaction volume of 12.5 µL containing 1000 pg of input DNA in a final concentration of 0.0 mm EDTA, 0.1 mm EDTA, 0.2 mm EDTA, 0.3 mm EDTA, 0.4 mm EDTA, 0.5 mm EDTA, 0.6 mm EDTA, 0.7 mm EDTA, 0.8 mm EDTA, 0.9 mm EDTA, and 1.0 mm EDTA. 1 µL of these samples were amplified with the improved multiplex assay and analyzed by CEFD.

PCR Amplification for the Improved Multiplex Assay

Samples were amplified using an ABI 9700 thermal cycler (Applied Biosystems, Foster City, Calif.). The basic amplification scheme for the original assay reported previously (1) was optimized and dramatically shortened. The original thermal cycling parameters were optimized using both the AmpliTaq® Gold (Applied Biosystems, Foster City, Calif.) and 2×GoTaq® Colorless Mastermix (Promega Corporation, Madison, Wis.) DNA polymerases. The optimized thermocycling parameters for the improved multiplex assay consist of a three-temperature cycle comprised of ten seconds at 98° C., sixty seconds at 55° C., and thirty seconds at 72° C. This three-temperature cycle is repeated 30 times, is followed by a ten-minute hold at 60° C., and then is followed by an infinite hold at room temperature (25° C.). These thermo-cycling parameters may be used interchangeably with either DNA polymerase listed above, but AmpliTaq® Gold requires an initial 11-minute hold at 96° C. to activate it. In our hands, the e2TAK DNA polymerase commercially available from TaKaRa Bio (Madison, Wis.) was not able to carry out optimal amplification of the improved multiplex assay at the thermal cycling parameters described above.

All primer sequences were synthesized by Invitrogen, Incorporated (Carlsbad, Calif.). The six primer sequences as ordered from Invitrogen included the three reverse primer sequences labeled with the blue fluorophore dye, FAM, and the three unlabeled forward primer sequences as follows:

```
                                            (SEQ ID NO: 7)
AMEL forward = 5'-ACC TCA TCC TGG GCA CCC TGG-3'

(SEQ ID NO: 8)
AMEL reverse = 5'-AGG CTT GAG GCC AAC CAT CAG-3'

(SEQ ID NO: 9)
SRY forward =  5'-ACG AAA GCC ACA CAC TCA AGA AT-3'
```

-continued

SRY reverse = 5'-CTA CAG CTT TGT CCA GTG GC-3' (SEQ ID NO: 10)

pRL forward = 5'-AAG GTG GTA AAC CTG ACG TTG-3' (SEQ ID NO: 11)

pRL reverse = 5'-TTC ATC AGG TGC ATC TTC TTG-3' (SEQ ID NO: 12)
FAM =

The primer sequences used to amplify the Amelogenin X and Y amplicons in the original assay were directly derived from publicly available sequence information used in the Promega Sex-Typing Kit (Promega Corporation, Madison, Wis.) (15). The primer sequences used to amplify the SRY amplicon in the improved multiplex assay were derived from the published sequence of the sex-determining region Y (SRY) gene (16) as well as published primer sequences used to amplify the SRY amplicon in other male-only human DNA quantification assays (11) (12). In the improved multiplex assay, the non-human DNA template material was added to each of the samples pre-amplification during the addition of the "master mix". The non-human DNA template material consists of the addition of the pRL null vector purchased from Promega Corporation (Madison, Wis.) that is diluted for use with sterile deionized $H_2O$ from a Millipore Elix and Milli-Q water system (Millipore Corporation, Billerica, Mass.). The optimal concentration of the primer sets, the pRL null vector, and the AmpliTaq® Gold (Applied Biosystems, Foster City, Calif.) within the master mix for amplification was previously optimized (18) for a reaction containing 12.5 µL final volume (11.5 µL master mix plus the addition of 1 µL questioned DNA sample) as 1.0 µM of Amelogenin primers, 1.0 µM of SRY primers, 0.1 µM of pRL primers, 0.5 pg of pRL plasmid. In this study, we opted to use the 2×GoTaq® Colorless Mastermix as our source of DNA Polymerase. The final optimal concentration of GoTaq® Colorless Mastermix was determined in this study to be 1.2× after addition of 7.5 µL of 2×GoTaq® Colorless Mastermix to the 12.5 µL total reaction volume.

Genetic Analysis of Samples Amplified by the Improved Multiplex Assay

The products of amplification resulting from the improved multiplex assay were analyzed using an ABI Prism 310 Genetic Analyzer (Applied Biosystems, Foster City, Calif.). 1.5 µL of amplified sample was mixed with 24.5 µL HiDi formamide (Applied Biosystems, Foster City, Calif.) and 0.5 µL GS-500 LIZ size standard (Applied Biosystems, Foster City, Calif.) according to recommendations of the supplier. Prepared samples were then electrokinetically injected for five seconds, four seconds, three seconds, two seconds, or one second depending upon the particular instrument utilized and the nature of the experiment performed. After injection, samples were allowed to electrophoresis for 21 minutes. Relative fluorescence unit (RFU) data (peak-height) was collected using the Macintosh-based 310 Collection Software with 5-dye collection. The original assay used a 4-dye platform for the detection of the FAM-labeled amplicons (1). We could distinguish no change in the detection of FAM-labeled amplicons using a 5-dye platform. In both platforms, the size standard is a dye having no spectral overlap with FAM. The GeneScan® Analysis version 3.1.2 software program was set to the manufacturer's default settings with a peak amplitude threshold set at 50 relative fluorescence units (RFUs). Alleles were then size-called and labeled with peak-height RFU using a Genotyper® version 2.5.2 software macro developed in our laboratory for describing and characterizing the four potential products of amplification resulting from the improved multiplex assay.

Generation of Standard Curves and Data Analysis for the Improved Multiplex Assay A standard curve for the improved multiplex assay was created by plotting the pre-amplification amount of DNA within a NIST SRM 2372 Standard A or B sample dilution series as described above against the peak-height RFU gathered for each sample in the dilution series with CEFD. For estimation of the DNA concentrations in unknowns, the peak height RFU value for each amplicon was compared against the standard curve data to determine a corresponding picogram amount of DNA for a peak of that RFU. To determine the total human DNA content within an unknown tube, the Amelogenin X and/or Y amplicon's peak-height RFU was compared to a female Amelogenin X standard curve to determine picogram amounts. To determine the amount of male DNA within an unknown sample, the SRY amplicon's peak height RFU in comparison to a male SRY standard curve determined the picogram amount in that sample. The percent coefficient of variation (CV) for a run of samples via CEFD was determined by running the 250 pg/µL NIST SRM 2372 Standard B female three times during any run, to sum the peak-height RFU for the Amelogenin X amplicon, and determine the mean, standard deviation, and percent CV for those three runs to determine the percent CV for electrophoretic injection for the CEFD instrument during the run. The same 250 pg/µL NIST SRM 2372 Standard B female sample was compared to the female Amelogenin X standard curve to ensure that the picogram amount estimated to be within that sample never exceeded a total CV of thirty percent (inclusive of the percent CV of the CEFD instrument used in the run).

DNA Quantification Using QuantiBlot®, Quantifiler®, and Quantifiler® Y

Estimates of DNA concentration in crime scene samples were produced using blotting/hybridization methods incorporated into the QuantiBlot® kit using colorimetric detection (Applied Biosystems, Foster City, Calif.). The highest concentration of quantity made by this method was estimated as 8 ng/µL (a two-fold intensity increase from the 2 ng/µL QuantiBlot® Standard A DNA sample supplied with the QuantiBlot® kit). The lowest concentration of quantity made by this method was estimated as $\leq 0.125$ ng/µl (the fourth dilution in a two-fold dilution series of the 2 ng/µL QuantiBlot® Standard A DNA sample supplied with the QuantiBlot® kit). No attempt was made to estimate DNA sample concentration below 0.125 ng/µL as any sample exhibiting less than this amount would require amplification of the full 10 µL allowable for later DNA profiling with the AmpFlSTR® Identifiler™ and/or the AmpFlSTR® Yfiler™ PCR Amplification Kits (Applied Biosystems, Inc, Foster City, Calif.). Actual casework DNA samples were also quantified by Sorenson Forensics, Inc. (Salt Lake City, Utah) using the Quantifiler® kit and the Quantifiler® Y kit from Applied Biosystems, Inc. (Foster City, Calif.) with all quantification data graciously provided to us after their analyses.

PCR Amplification and Genetic Analysis for Generating DNA Profiles

Some samples of purified and quantified DNA were diluted so that approximately 1 ng of DNA from the sample was targeted for amplification using an ABI 9700 thermal cycler (Applied Biosystems, Foster City, Calif.) in a 25-µL reaction volume using the AmpFlSTR® Identifiler™ PCR Amplification Kit and/or the AmpFlSTR® Yfiler™ PCR Amplification Kit (Applied Biosystems, Inc, Foster City, Calif.) according to manufacturer's specifications. Products of amplification were analyzed using an ABI Prism 310 Genetic Analyzer (Applied Biosystems, Foster City, Calif.). 1.5 µL of amplified sample was mixed with 24.5 µL HiDi formamide (Applied Biosystems, Foster City, Calif.) and 0.5 µL GS-500 LIZ size standard (Applied Biosystems, Foster City, Calif.) according to recommendations of the supplier. Prepared samples were then electrokinetically injected for five seconds and allowed to electrophoresis for 28 minutes using a five-dye platform. Data was collected using the Macintosh-based 310 Collection Software with 5-dye collection, analyzed with the GeneScan® Analysis version 3.1.2 software, and then size-called and labeled using the manufacturer-supplied macros for the Genotyper® version 2.5.2 software.

Results

Figure 5A:
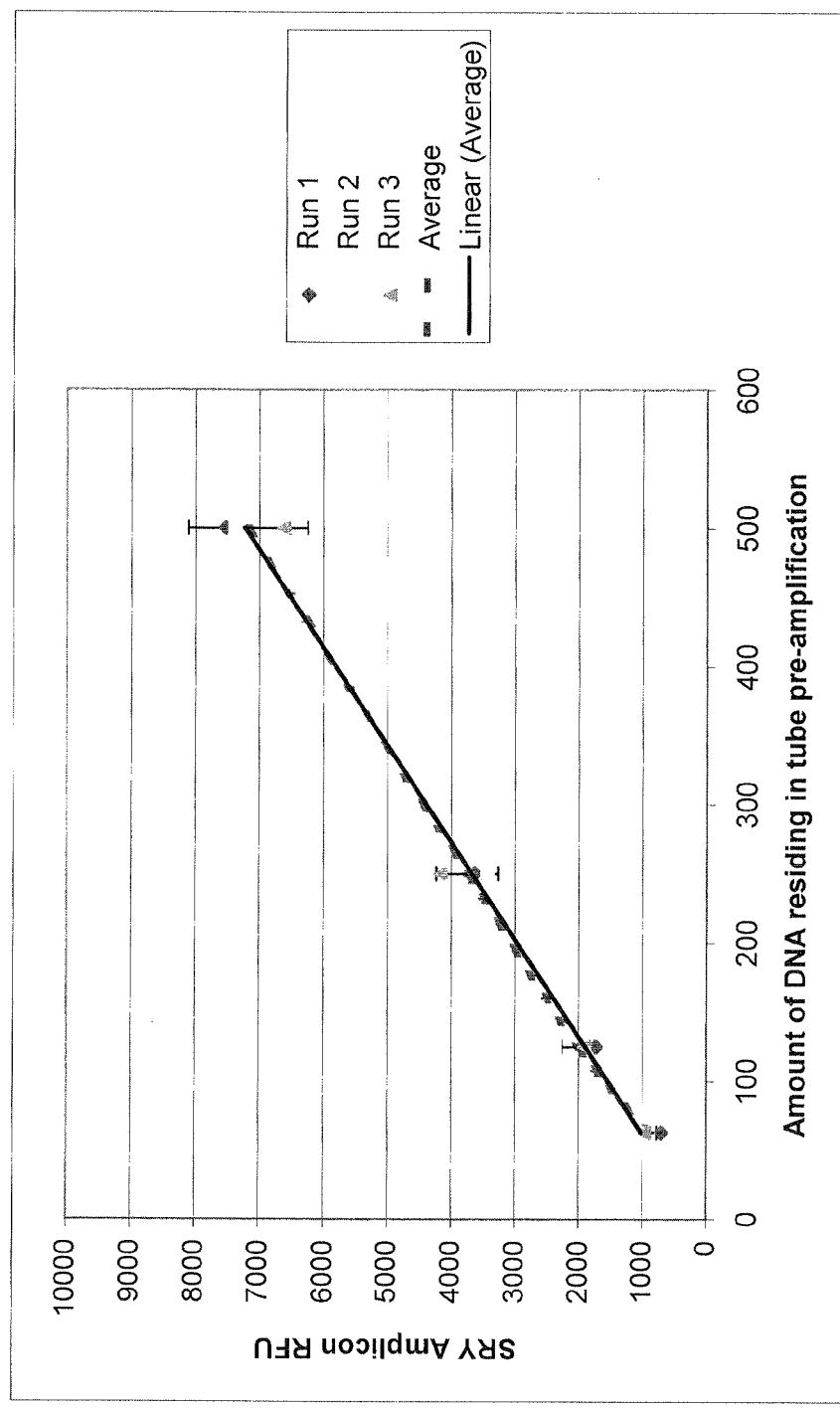
FIGS. 5A-B. Perfect Standard Curve A, This standard curve was produced using the NIST SRM 2372 Standard A male sample assayed by the improved multiplex assay from three independent analyses. Standard curves were produced by using the same samples of Standard A male described in the FIG. 4a legend, but the range was collapsed to the data points from the 63 pg/μL, 125 pg/μL, 250 pg/μL, and the 500 pg/μL dilutions only. At each data point, the fluorescence incorporated into the SRY amplicon from three separate assays and the mean of the three assays is shown along with error bars reflecting a coefficient of variation of 12.98% at all concentrations of input reference DNA. A linear regression line of the data from the average of the three separate assays ($R^2=0.9984$) is also shown. B, This standard curve was produced using the NIST SRM 2372 Standard B female sample assayed by the improved multiplex assay from three independent analyses. Standard curves were produced by using the same samples of Standard B female described in the FIG. 4b legend, but the range was collapsed to the data points from the 63 pg/μL, 125 pg/μL, 250 pg/μL, and the 500 pg/μL dilutions only. At each data point, the fluorescence incorporated into the X amplicon from three separate assays and the mean of the three assays is shown along with error bars reflecting a coefficient of variation of 25.66% at all concentrations of input reference DNA. A linear regression line of the data from the average of the three separate assays ($R^2=0.998$) is also shown.
Figure 5B:
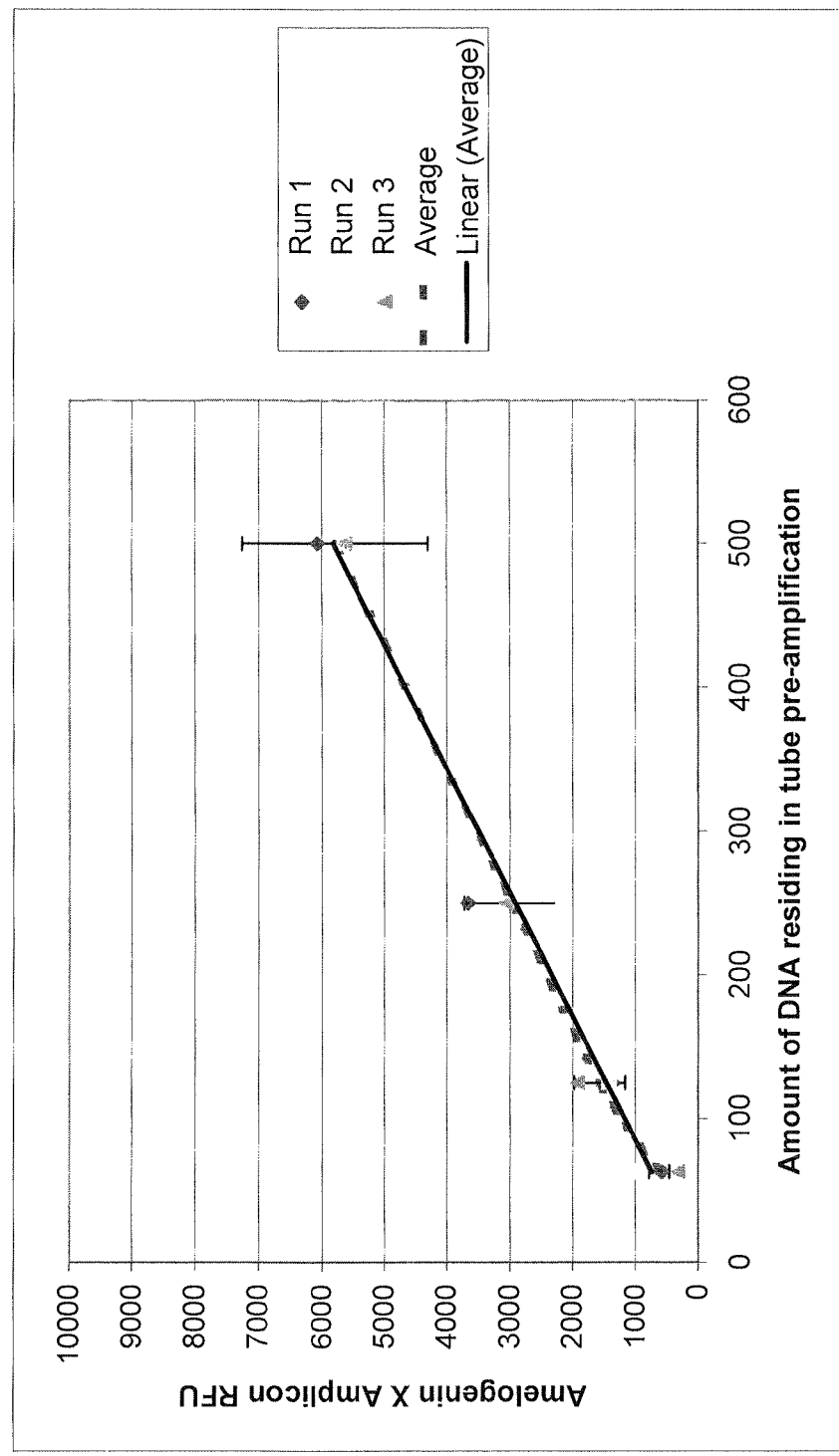
Figure 6A:
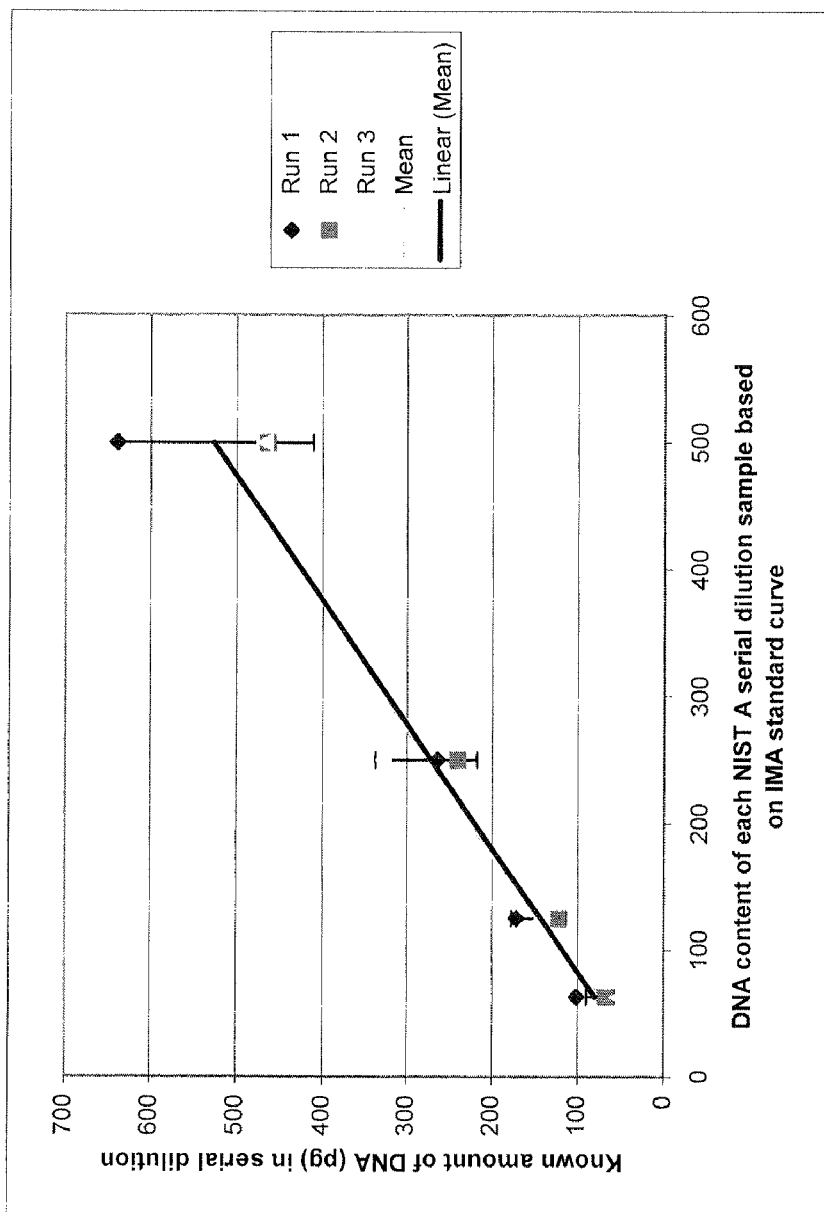
FIGS. 6A-C. Accuracy of the Improved Multiplex Assay. A, Standard curves were produced by using the same dilutions of the NIST Standard A male as described in the FIG. 5b legend. At each data point, the total human DNA content of the four NIST Standard A dilutions (63 pg/μL, 125 pg/μL, 250 pg/μL, and 500 pg/μL) were compared to the standard curve presented in FIG. 5b by summing the fluorescence of the Amelogenin X and Amelogenin Y amplicons from three separate assays. The mean estimated concentration of the three assays is shown along with error bars reflecting a coefficient of variation of 21.55% at all concentrations of input reference DNA. A linear regression line of the data from the average of the three separate assays ($R^2=0.9992$) is also shown. B, Standard curves were produced by using the same dilutions of the NIST Standard B female as described in the FIG. 5b legend. At each data point, the total human DNA content of the four NIST Standard B dilutions (63 pg/μL, 125 pg/μL, 250 pg/μL, and 500 pg/μL) were compared to the standard curve presented in FIG. 5b by summing the fluorescence of the Amelogenin X and Amelogenin Y (absent in this sample) amplicons from three separate assays. The mean of the three assays is shown along with error bars reflecting a coefficient of variation of 13.95% at all concentrations of input reference DNA. A linear regression line of the data from the average of the three separate assays ($R^2=0.9985$) is also shown. C, Standard curves were produced by using the same dilutions of the NIST Standard A male as described in the FIG. 5a legend. At each data point, the total human DNA content of the four NIST Standard A dilutions (63 pg/μL, 125 pg/μL, 250 pg/μL, and 500 pg/μL) were compared to the standard curve presented in FIG. 5a by the fluorescence of the SRY amplicon from three separate assays. The mean of the three assays is shown along with error bars reflecting a coefficient of variation of 26.05% at all concentrations of input reference DNA. A linear regression line of the data from the average of the three separate assays ($R^2=0.9979$) is also shown.
Figure 6B:
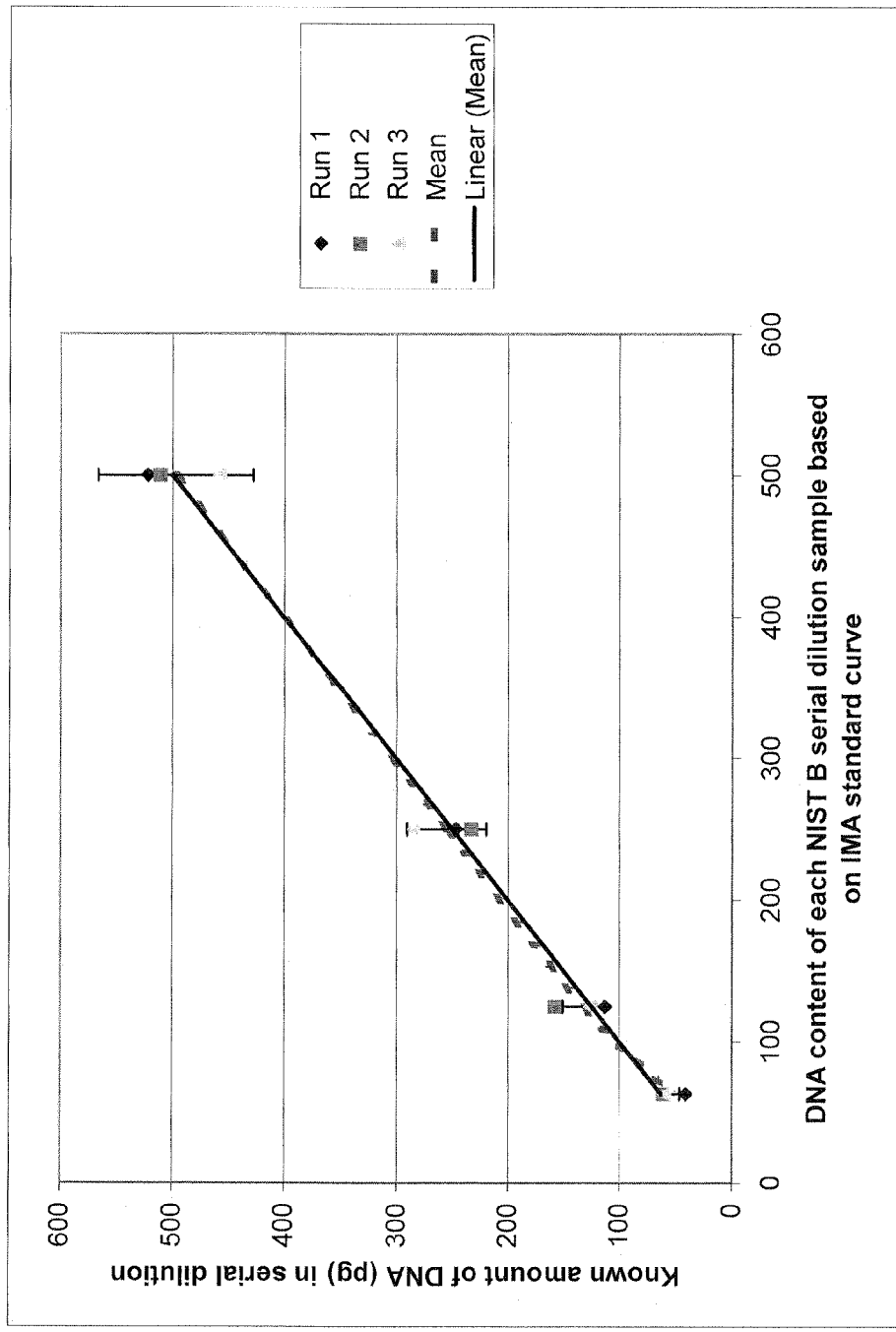
Figure 6C:
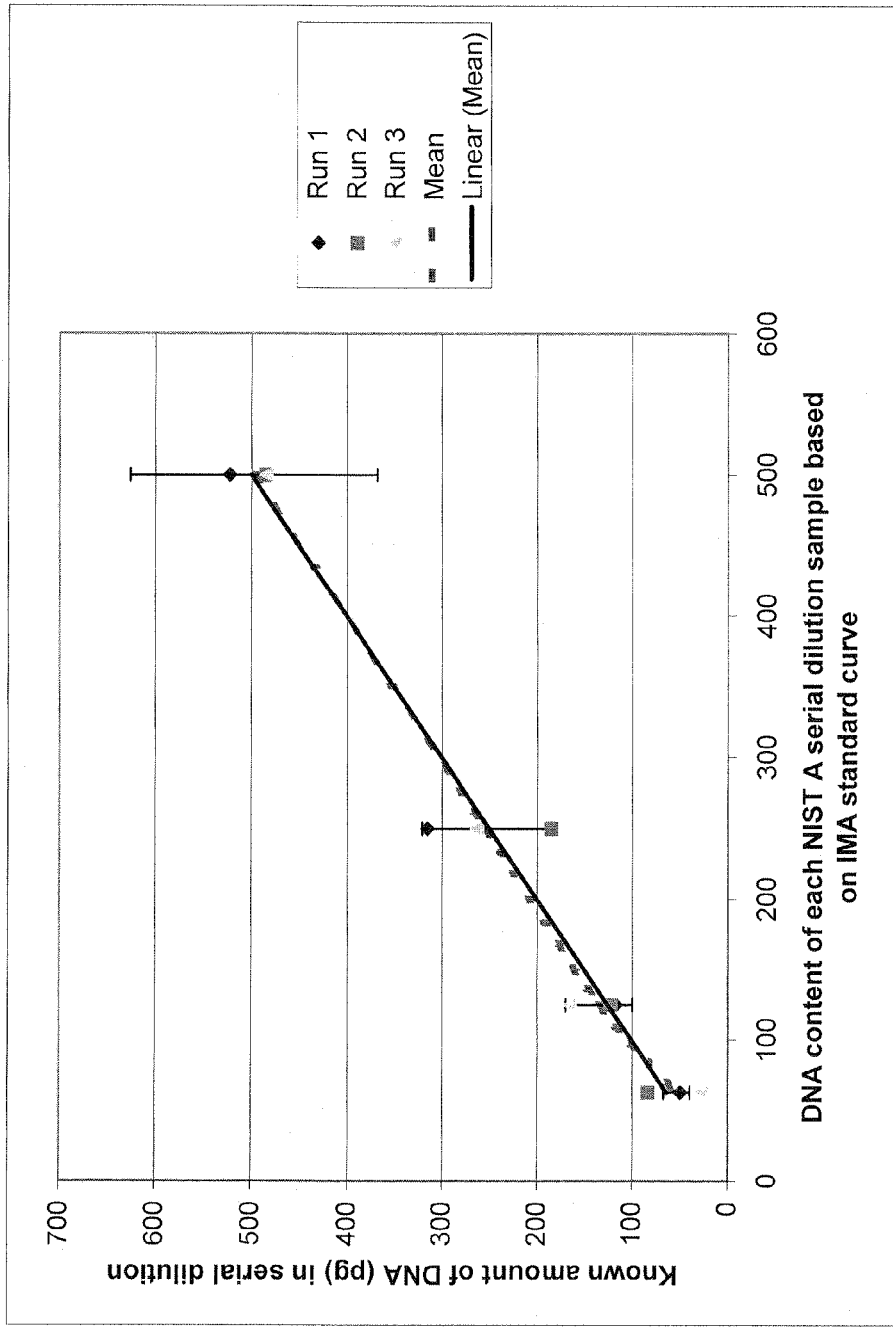

The original assay and the improved multiplex assay both function on several theoretical premises. The first is that the amount of DNA residing in a sample pre-amplification will amplify with the same kinetics of amplification dependent upon the amount of input DNA and that the amplification kinetics of a basic polymerase chain reaction (PCR) will result in a reproducible amount of end-point amplification product. The second premise is that the end-point products of amplification can be analyzed by CEFD and that during CEFD analysis, a certain amount of the product will be reproducibly diluted for introduction into the CEFD device, this diluted product will be reproducibly electrokinetically injected into the capillary of the CEFD device, and the DNA product as it passes the detection mechanism will emit a reproducible amount of fluorescence. This fluorescence will be reproducibly collected by the CEFD device. If these premises hold true, then the fluorescence of the amplification product of a DNA sample will be directly proportional to the amount of DNA residing in a sample pre-amplification. The incidence of fluorescence for a dilution series of DNA samples of varying DNA content can be plotted as a standard curve and the standard curve can be used to determine the amount of input DNA that must have resided in any unknown sample pre-amplification by knowing its level of fluorescence during CEFD analysis. However, over ten separate amplifications a standard curve generated from the original assay had a reported $R^2$ value of 0.9751 and a CV of about thirty percent (1). The source of the CV was not characterized or understood. If a dilution series ranging from 32 pg/µL to 1000 pg/µL of the NIST SRM 2372 Standard A male is amplified using the improved multiplex assay and run on a CEFD device the average fluorescence (peak height RFU) that is gathered from the SRY amplicon for every dilution in the series results in a standard curve that can be seen in FIG. 7a. Similarly, if a dilution series ranging from 32 pg/µL to 1000 pg/µL of the NIST SRM 2372 Standard B female is amplified using the improved multiplex assay and run on a CEFD device the average fluorescence (peak height RFU) that is gathered from the Amelogenin X amplicon for every dilution in the series results in a standard curve that can be seen in FIG. 7b. We expected that the data points would represent a one to one relationship between the amount of fluorescence and the amount of input DNA pre-amplification. In other words, we expected an $R^2$ value of 1.0 and we expected that the line of regression (seen as a bold line) in FIG. 7 should mirror the plotted line of the average of the fluorescence data gathered at each dilution (dotted line). But as one can see, the relationship did not appear to be linear based upon the data plotted in FIG. 7 or in the previously published original assay (1). We then determined that our data was probably being skewed because the dynamic range of the assay was out of the linear range for the CEFD device. We determined from the raw CEFD data that the peak height RFU estimates were truncated for the 1000 pg DNA samples. Truncation of peaks would indicate that the limit of linearity (LOL) for the CEFD device was being exceeded. We also decided to not use sample dilutions of less than 63 pg to generate our standard curves because the limit of quantification (LOQ) for the CEFD device we were using was anywhere from 35 pg to 100 pg (19, 20). The standard curve that resulted from plotting a dilution series ranging from 63 pg/µL to 500 pg/µL for the NIST SRM 2372 Standard A male and the NIST SRM 2372 Standard B female versus the average fluorescence (peak height RFU) that is gathered from the appropriate amplicon for every dilution in the series results in the standard curves that can be seen in the male SRY standard curve in FIG. 5a and the female Amelogenin X standard curve in FIG. 5b. After accounting for the linear and dynamic range of the CEFD device, a valid linear relationship between the male SRY standard curve was exhibited with an $R^2$ value of 0.9984 in FIG. 5a and a valid linear relationship between the female X standard curve was exhibited with an $R^2$ value of 0.9980 in FIG. 5b. We then evaluated the accuracy of the improved multiplex assay standard curves to determine the amount of total human and male-only DNA residing in samples of known concentration. In FIG. 6a, the female X standard curve was used to determine the total human DNA content of a dilution series of known DNA made from the NIST SRM 2372 Standard A male. In FIG. 6b, the female X standard curve was used to determine the total human DNA content of a dilution series of known DNA made from the NIST SRM 2372 Standard B female. In FIG. 6c the male SRY standard curve was used to determine the male-only DNA content of a dilution series of known DNA made from the NIST SRM 2372 Standard A male. FIG. 6a exhibited an $R^2$ value of 0.9992, FIG. 6b exhibited an $R^2$ value of 0.9985, and FIG. 6c exhibited an $R^2$ value of 0.9979 demonstrating that the improved multiplex assay functions with a very high degree of accuracy. In Table 5 the percent CV was examined for the data sets used to generate the three FIG. 6 graphs.

TABLE 5

Reproducibility of the Improved Multiplex Assay

| # Sample | Run 1 | Run 2 | Run 3 | µ | σ | CV |
|---|---|---|---|---|---|---|
| 1 NIST A 1000 pg Amel (X + Y) RFU | 13612 | 12321 | 12470 | 12801 | 706.3 | 5.52% |
| IMA total human estimated pg of DNA | 950 | 859 | 870 | 893 | 49.67 | 5.56% |
| 2 NIST A 500 pg Amel (X + Y) RFU | 9198 | 6716 | 6765 | 7559.67 | 1419 | 18.77% |
| IMA total human estimated pg of DNA | 639 | 464 | 468 | 523.667 | 99.9 | 19.08% |
| 3 NIST A 250 pg Amel (X + Y) RFU | 3869 | 3524 | 4777 | 4056.67 | 647.2 | 15.95% |
| IMA total human estimated pg of DNA | 264 | 240 | 328 | 277.333 | 45.49 | 16.40% |
| 4 NIST A 125 pg Amel (X + Y) RFU | 2572 | 1888 | 2142 | 2200.67 | 345.8 | 15.71% |
| IMA total human estimated pg of DNA | 172 | 124 | 142 | 146 | 24.25 | 16.61% |
| 5 NIST A 63 pg Amel (X + Y) RFU | 1572 | 1073 | 872 | 1172.33 | 360.4 | 30.74% |
| IMA total human estimated pg of DNA | 102 | 67 | 53 | 74 | 25.24 | 34.11% |

TABLE 5-continued

Reproducibility of the Improved Multiplex Assay

| # Sample | Run 1 | Run 2 | Run 3 | μ | σ | CV |
|---|---|---|---|---|---|---|
| 6 NIST A 32 pg Amel (X + Y) RFU | 635 | 483 | 535 | 551 | 77.25 | 14.02% |
| IMA total human estimated pg of DNA | 36 | 25 | 29 | 30 | 5.568 | 18.56% |
| Average σ of Total Human RFU for # 1-6 | | | | | 592.7 | 16.79% |
| Average σ of Total Human DNA (pg) for # 1-6 | | | | | 41.69 | 18.39% |
| Average σ of Total Human RFU for # 2-5 | | | | | 693.1 | 20.30% |
| Average σ of Total Human DNA (pg) for # 2-5 | | | | | 48.72 | 21.55% |
| $R^2$ value of pg for # 1-6 | 0.9719 | 0.9980 | 0.9822 | 0.9914 | 0.013 | 1.33% |
| $R^2$ value of pg for # 2-5 | 0.9810 | 0.9999 | 0.9394 | 0.9992 | 0.031 | 3.10% |
| 1 NIST B 1000 pg Amel (X + Y) RFU | 7385 | 7450 | 6270 | 7035.00 | 663.31 | 9.43% |
| IMA total human estimated pg of DNA | 511 | 516 | 433 | 486.67 | 46.54 | 9.56% |
| 2 NIST B 500 pg Amel (X + Y) RFU | 7532 | 7376 | 6624 | 7177.33 | 485.51 | 6.76% |
| IMA total human estimated pg of DNA | 522 | 511 | 458 | 497.00 | 34.22 | 6.89% |
| 3 NIST B 250 pg Amel (X + Y) RFU | 3629 | 3428 | 4175 | 3744.00 | 386.55 | 10.32% |
| IMA total human estimated pg of DNA | 247 | 233 | 285 | 255.00 | 26.91 | 10.55% |
| 4 NIST B 125 pg Amel (X + Y) RFU | 1729 | 2373 | 1910 | 2004.00 | 332.13 | 16.57% |
| IMA total human estimated pg of DNA | 113 | 158 | 126 | 132.33 | 23.16 | 17.50% |
| 5 NIST B 63 pg Amel (X + Y) RFU | 699 | 986 | 971 | 885.33 | 161.54 | 18.25% |
| IMA total human estimated pg of DNA | 41 | 61 | 60 | 54.00 | 11.27 | 20.87% |
| 6 NIST B 32 pg Amel (X + Y) RFU | 376 | 667 | 423 | 488.67 | 156.22 | 31.97% |
| IMA total human estimated pg of DNA | 18 | 38 | 21 | 25.67 | 10.79 | 42.02% |
| Average σ of Total Human RFU for # 1-6 | | | | | 364.21 | 15.55% |
| Average σ of Total Human DNA (pg) for # 1-6 | | | | | 25.48 | 17.90% |
| Average σ of Total Human RFU for # 2-5 | | | | | 341.43 | 12.98% |
| Average σ of Total Human DNA (pg) for # 2-5 | | | | | 23.89 | 13.95% |
| $R^2$ value of pg for # 1-6 | 0.7912 | 0.8112 | 0.7270 | 0.7837 | 0.04 | 5.61% |
| $R^2$ value of pg for # 2-5 | 0.9999 | 0.9880 | 0.9784 | 0.9985 | 0.01 | 1.08% |
| 1 NIST A 1000 pg SRY RFU | 7602 | 7577 | 7283 | 7487.33 | 177.40 | 2.37% |
| IMA total male estimated pg of DNA | 655 | 652 | 627 | 644.67 | 15.37 | 2.38% |
| 2 NIST A 500 pg SRY RFU | 6066 | 5629 | 5623 | 5772.67 | 254.05 | 4.40% |
| IMA total male estimated pg of DNA | 522 | 484 | 484 | 496.67 | 21.94 | 4.42% |
| 3 NIST A 250 pg SRY RFU | 3659 | 2156 | 3062 | 2959.00 | 756.78 | 25.58% |
| IMA total male estimated pg of DNA | 315 | 185 | 263 | 254.33 | 65.43 | 25.73% |
| 4 NIST A 125 pg SRY RFU | 1366 | 1421 | 1921 | 1569.33 | 305.79 | 19.49% |
| IMA total male estimated pg of DNA | 117 | 122 | 165 | 134.67 | 26.39 | 19.60% |
| 5 NIST A 63 pg SRY RFU | 578 | 968 | 313 | 619.67 | 329.48 | 53.17% |
| IMA total male estimated pg of DNA | 49 | 83 | 26 | 52.67 | 28.68 | 54.45% |
| 6 NIST A 32 pg SRY RFU | 456 | 267 | 456 | 393.00 | 109.12 | 27.77% |
| IMA total male estimated pg of DNA | 38 | 22 | 38 | 32.67 | 9.24 | 28.28% |
| Average σ Male-Only RFU for # 1-6 | | | | | 322.10 | 22.13% |
| Average σ Male-Only DNA (pg) for # 1-6 | | | | | 27.84 | 22.48% |
| Average σ Male-Only RFU for # 2-5 | | | | | 411.53 | 25.66% |
| Average σ Male-Only DNA (pg) for # 2-5 | | | | | 35.61 | 26.05% |
| $R^2$ value of pg for # 1-6 | 0.8973 | 0.9456 | 0.9133 | 0.9288 | 0.025 | 2.65% |
| $R^2$ value of pg for # 2-5 | 0.9780 | 0.9673 | 0.9699 | 0.9979 | 0.006 | 0.56% |

Table 5 shows NIST SRM 2372 Standard A and B at the concentrations produced by the serial dilution scheme described in the Materials and Methods. Three separate amplifications were performed for each concentration of Standard A and Standard B and injected for five seconds on an ABI Prizm 310 Genetic Analyzer. The mean RFU height, standard deviation, and coefficient of variation were calculated for the sum of the Amelogenin X and Amelogenin Y amplicons and for the SRY amplicon from the three separate amplifications. The average RFU height of the sum of the Amelogenin X and Amelogenin Y amplicons after the three amplifications was used to construct a standard curve to produce the total human DNA estimate within each dilution. The average RFU height of the SRY amplicon after the three amplifications was used to construct a standard curve to produce the male-only DNA estimate within each dilution. The average standard deviation and coefficient of variation for each dilution was calculated for the RFU height of the relevant amplicon(s) and estimated amount of DNA for the 32 pg/μL-1000 pg/μL range of data as well as for the 63 pg/μL-500 pg/μL range of data. The $R^2$ value for each amplification and for the average of the three amplifications for the amount of DNA was calculated, along with the standard deviation and coefficient of variation.

For Table 5, the percent CV was calculated for each picogram amount of input DNA ranging from 32 pg/μL to 1000 pg/μL for each standard curve analysis in FIG. 6. The percent CV was also calculated for each total fluorescence value of the relevant amplicons observed to calculate either total human (sum of fluorescence from the Amelogenin X and Amelogenin Y amplicons) or male-only (fluorescence of SRY amplicon) DNA concentration for each amount of input DNA ranging from 32 pg/μL to 1000 pg/μL. When calculating the amount of total human DNA in the NIST SRM 2372 Standard A male DNA ranging from 32 pg/μL to 1000 pg/μL the average percent CV is 16.79% for RFU, 18.39% for picogram amount of DNA. If graphed, the linear relationship of these points has an average $R^2$ value of 0.9914. For this same sample, if the range of DNA concentrations narrows from 63 pg/μL to 500 pg/μL the average percent CV is 20.30% for RFU, 21.55% for picogram amount of DNA. If graphed, the linear relationship of these points has an average $R^2$ value of 0.9992. When calculating the amount of total human DNA in the NIST SRM 2372 Standard B female DNA ranging from 32 pg/μL to 1000 pg/μL the average percent CV is 15.55% for RFU, 17.90% for picogram amount of DNA and the linear relationship of these points has an average $R^2$ value of 0.7837. This same sample with a narrowed range demonstrate an average percent CV is 12.98% for RFU, 13.95% for picogram amount of DNA, and an average $R^2$ value of 0.9985. When calculating the amount of male-only DNA in the NIST SRM 2372 Standard A male DNA ranging from 32 pg/µL to 1000 pg/µL the average percent CV is 22.13% for RFU, 22.48% for picogram amount of DNA. If graphed, the linear relationship of these points has an average $R^2$ value of 0.9288. This same sample with a collapsed range has an average percent CV of 25.66% for RFU, 26.05% for picogram amount of DNA, and an average $R^2$ value of 0.9979. We decided from this data that the standard curves for the improved multiplex assay should be generated from the 63 pg/µL, 125 pg/µL, 250 pg/µL, and the 500 pg/µL dilutions of standard DNA reference material as these samples generated better $R^2$ values.

Data concerning the reproducibility of the improved multiplex assay and the ability to estimate the picogram amount of input DNA in a male and a female sample at various dilutions of that sample with an improved multiplex assay standard curve, is presented in FIG. 14 in tabular form.

For FIG. 14, the concentration of DNA within the samples was not precisely known (see the Materials and Methods section for information concerning general concentration of these samples) so these samples were serial diluted by halves and subjected to amplification and analysis using the improved multiplex assay. The percent CV was calculated for estimated picogram amounts of DNA in 1 µL of each serial dilution and the fluorescence amounts of the relevant amplicons for each serial dilution of the male sample and female sample as indicated in FIG. 14. When calculating the amount of total human DNA in all dilutions of the female sample, the average percent CV is 23.77% for RFU, and 21.03% for picogram amount of DNA (FIG. 14). When calculating the amount of total human DNA in all dilutions of the male sample, the average percent CV is 23.16% for RFU, and 21.36% for picogram amount of DNA (FIG. 14). When calculating the amount of male-only DNA in all dilutions of the male sample, the average percent CV is 21.06% for RFU, and 20.49% for picogram amount of DNA (FIG. 14).

The CV for the improved multiplex assay as a whole was approximately 20% from the accuracy data presented in Table 5 with a range of 13% to 26%. We next wanted to determine the percent CV contributed by each component of the improved multiplex assay. Several opportunities exist in the improved multiplex assay for introducing variation into the estimation of DNA quantity in a sample. We theorized that the potential existed for the introduction of variance during sample pipetting (during the creation of a dilution series or the dilution of amplified sample for CEFD analysis), during the PCR amplification step (stochastic effects), during the electrokinetic injection of a sample into the CEFD device, and during the detection and collection of peak height data by the CEFD device. The twenty pipetting devices utilized in our laboratory are calibrated in triplicate every year. These devices have an average documented CV of 0.16%. Even considering the additive pipetting error seen in the creation of serial dilutions, pipetting percent CV seemed to be no greater than 1% in our laboratory. This left 19% of the 20% average CV seen in the improved multiplex assay unaccounted for. Next, we determined the percent CV introduced during electrokinetic injection and fluorescent detection on five CEFD devices. To determine the percent CV for a CEFD device, we serially injected (eighteen times in a row) one sample of the amplification products from an AmpFlSTR® Identifiler™ DNA profiling reaction performed on the Indentifiler™ female positive control on five CEFD devices. By determining the average peak-height fluorescence and size-calling data of the TH01 9.3 allele exhibited by this sample during the eighteen analyses of this single sample by each device, we determined the percent CV of a CEFD device for size-calling and for electrokinetic injection and fluorescence detection of a sample. The results are presented in tabular form in FIG. 15. Our conclusion was that the percent CV for any particular CEFD device can be kept below 5% with proper attention to instrument set-up and maintenance. To determine the instrumental percent CV for every standard curve and sample run performed in this study, we chose to serially inject the NIST SRM 2372 Standard B female 250 pg/µL dilution three times, once near the beginning of a run, once in the middle of a run, and once near the end of a run. The average peak height fluorescence of the Amelogenin X amplicon in this sample would be used to determine the CEFD percent CV for all sample data gathered during that run. The highest CEFD CV noted for any of the sample runs used to generate the improved multiplex assay data presented in this study was 5.68% with the average CEFD CV being 3.33% over all runs (data not shown).

PCR was the only remaining component for the introduction of variation to the improved multiplex assay. Stochastic effects were expected to cause a certain amount of variation of amplified product to arise from a specific amount of input DNA. Due to these stochastic effects, the limit of detection for the PCR reaction has already been documented for qualitative DNA analysis (DNA profiling based upon a qualitative assessment of amplicon appearance or drop-out after size-migration through a CEFD device) at around 35 pg of total input DNA (20, 21), but what would be the percent CV for the PCR reaction itself? If we look back to the data presented in Table 5, the percent CV for each picogram amount of input DNA is given and the average, as stated previously is approximately 20% (range of 13% to 26%). If pipetting and dilution CV is approximately 1% and CEFD detection is approximately 5%, then approximately 14% CV remains with a range of remaining CV of 7% to 20%. We theorize that the PCR reaction itself has a CV of 10-15% when the input DNA is between 63 pg and 500 pg. The data generated by our improved multiplex assay also indicates that the PCR CV increases beyond 10-15% when the input DNA is below 63 pg. An increased CV for input DNA below 63 pg is also seen in other PCR-based quantification methods, namely the Quantifiler® and Quantilfer® Y kits (10). The effect of introducing more than 500 pg of input DNA into the PCR reaction is unknown for the improved multiplex assay because of the limit of linearity of the CEFD device.

Figure 7A:
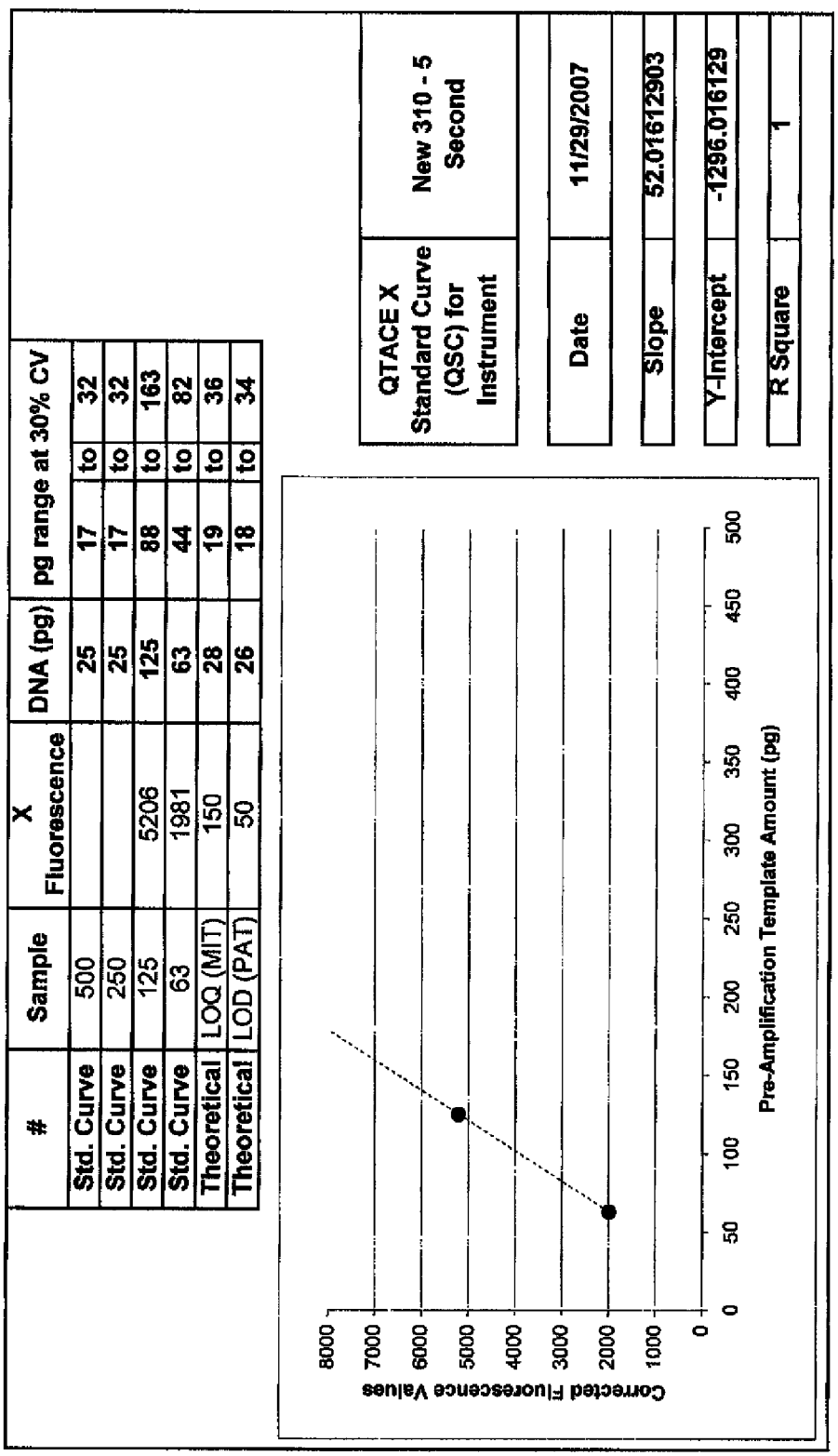
FIGS. 7A-E. Standard curve results gathered by a "sensitive" CEFD and the effect of decreasing electrokinetic injection time. A dilution series of NIST SRM 2372 Standard B was made as described in the Materials and Methods. The dilution series was injected for five seconds, four seconds, three seconds, two seconds, and one second on the sensitive ABI Prizm 310 Genetic Analyzer. A standard curve was generated from the data gathered for each injection time. A, the five-second standard curve; B, the four-second standard curve; C, the three-second standard curve; D, the two-second standard curve; E, the one-second standard curve. For each standard curve, the slope of the line of regression, the y-intercept of the line of regression, and the $R^2$ value of the data were calculated. The dilutions that had truncated peaks do not have a value in the table. The LOQ (MIT) is the "limit of quantification" for the CEFD device sometimes referred to as the "match interpretation threshold" by DNA analysts.
Figure 7B:
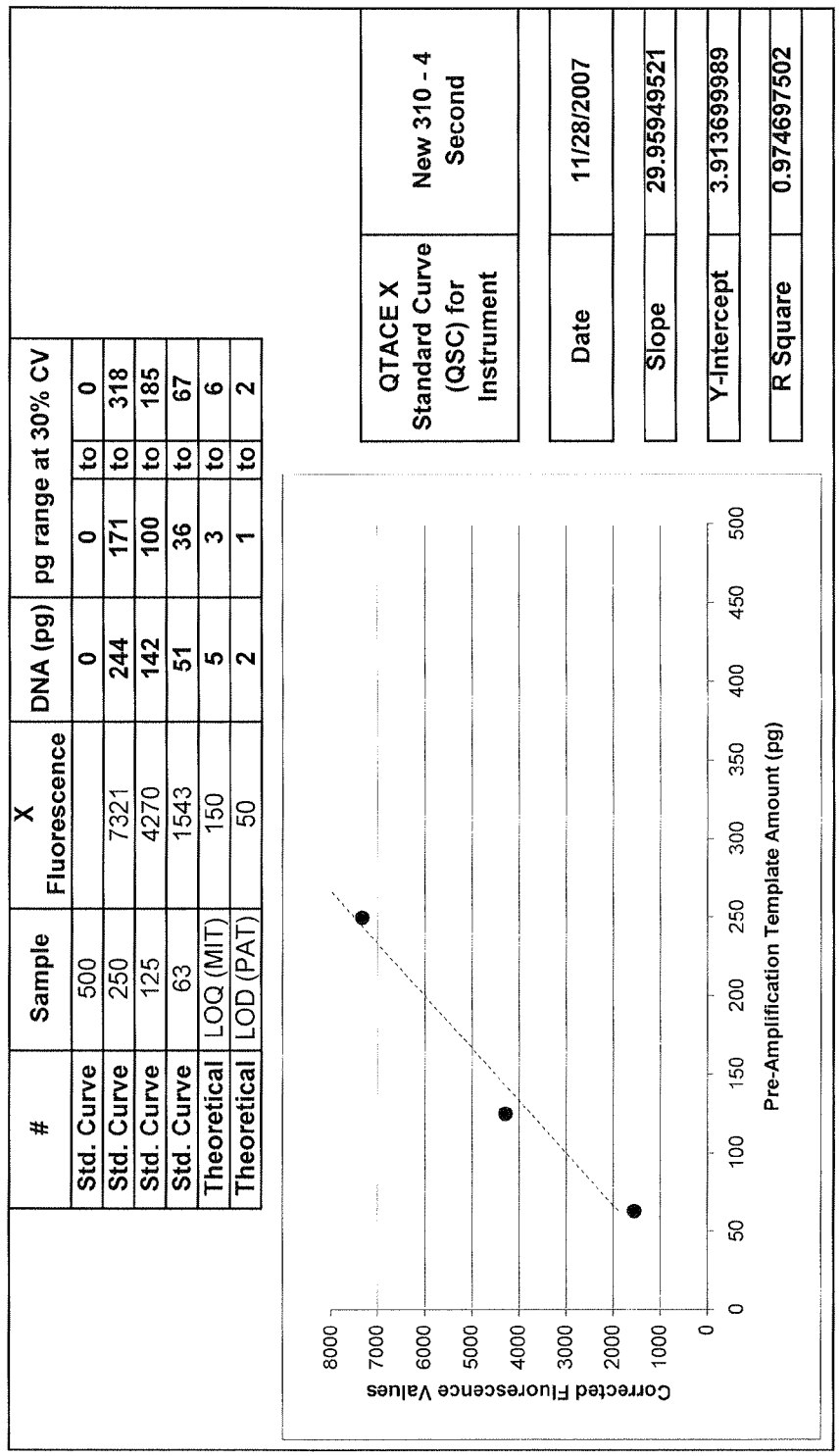
Figure 7C:
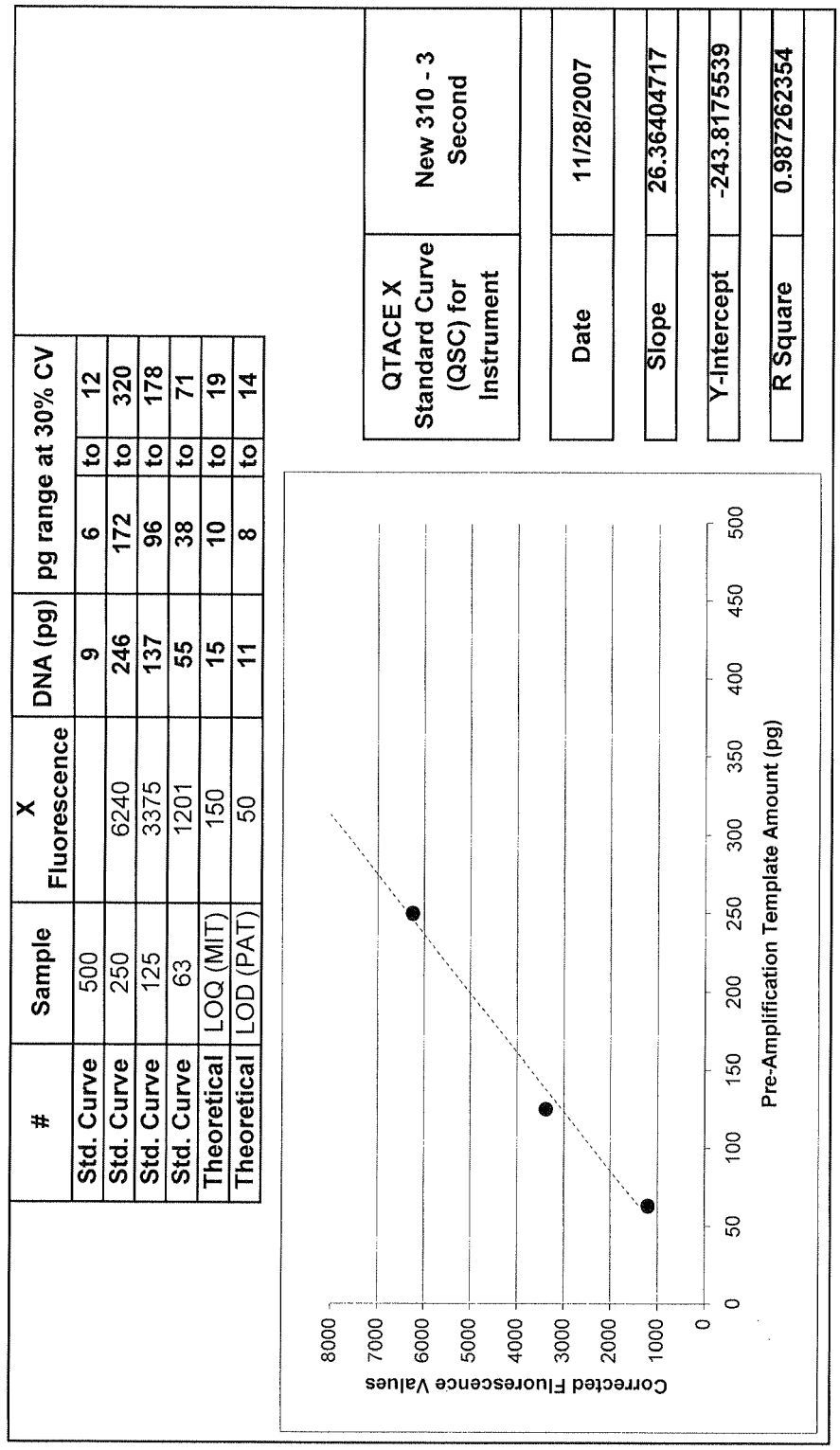
Figure 7D:
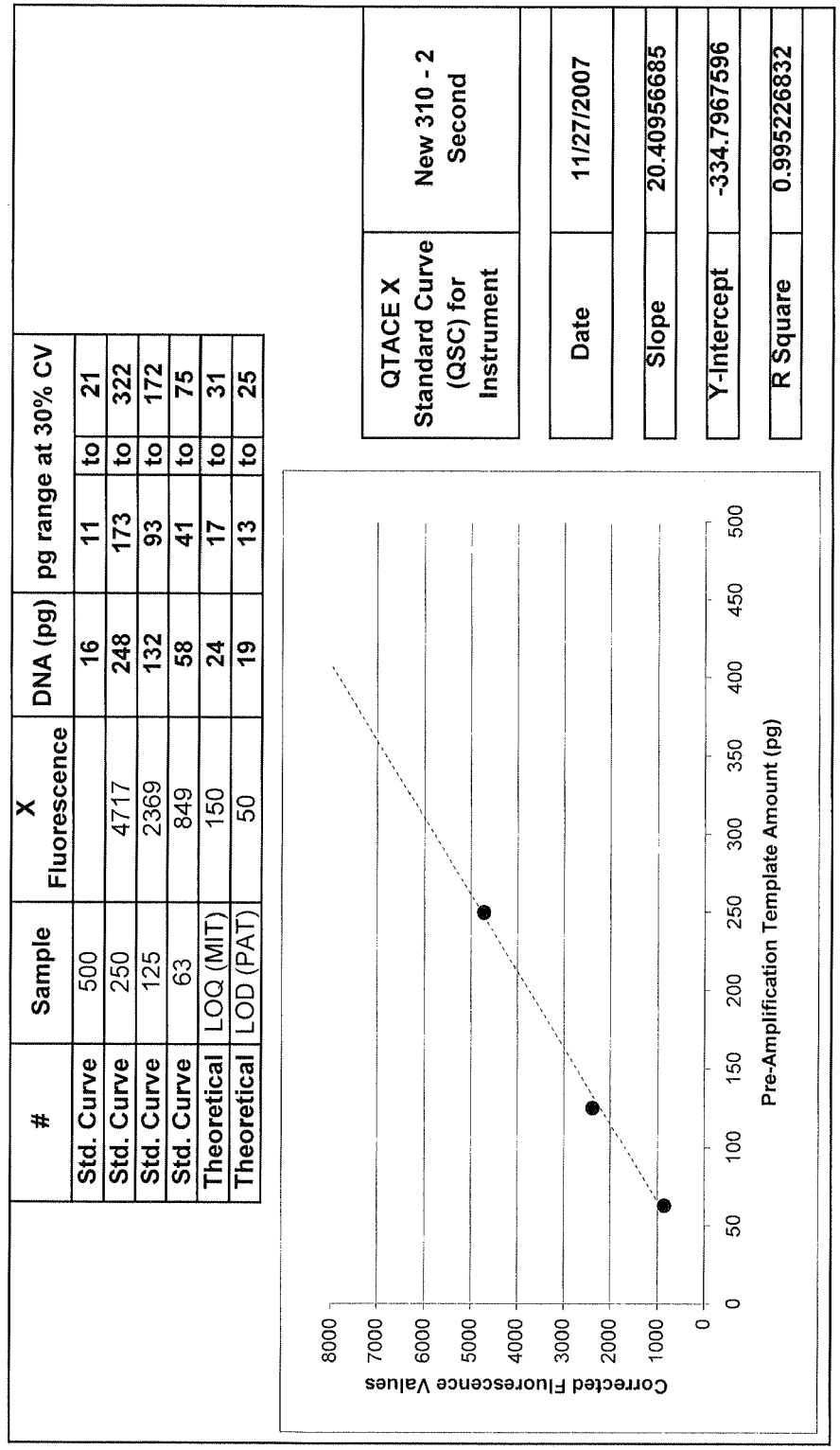
Figure 7E:
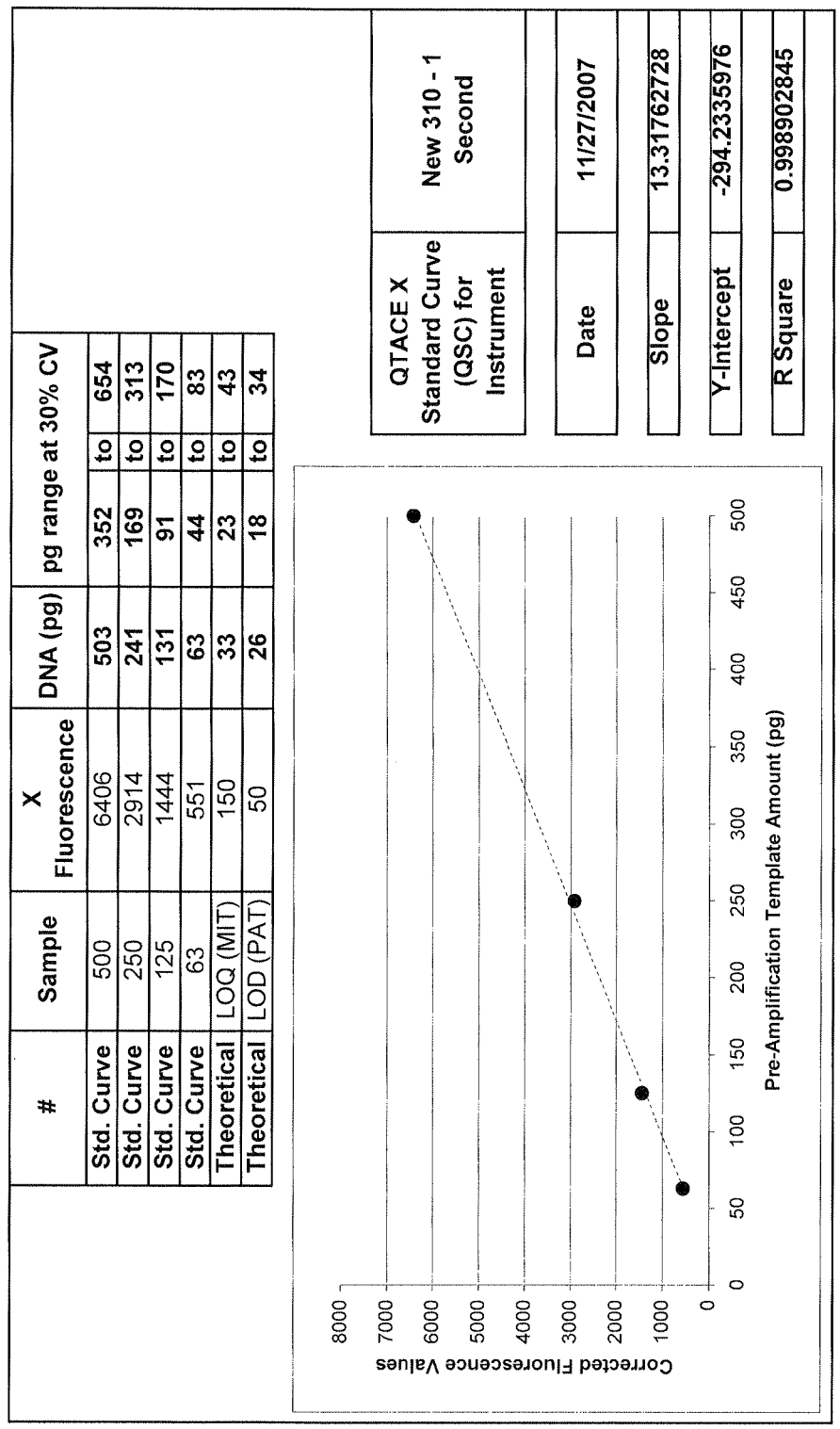

During our study we noted that some CEFD devices are more sensitive in detecting fluorescence than others. Increased sensitivity translates to a lowered LOL for a CEFD device. An input DNA of <500 pg will appear truncated if a CEFD device with a lowered LOL is used for analysis. In this instance, we developmentally validated using electrokinetic injection times of less than five seconds on CEFD devices with an increased sensitivity. The results of a shortened electrokinetic injection time on a sensitive CEFD device are presented in FIG. 7. In FIG. 7*a* the effects of increased CEFD sensitivity on the generation of a standard curve from 63 pg, 125 pg, 250 pg, and 500 pg input standard DNA reference material is shown. The result of increased sensitivity on this CEFD device is to gather truncated peak height RFU data. Truncation makes the peak height RFU value invalid. FIGS. 7*b*, 7*c*, 7*d*, and 7*e* show the standard curves generated from the same input DNA amounts with decreasing electrokinetic injection times of 4, 3, 2, and 1 second, respectively. Based upon the information presented in FIGS. 4-7, Tables 5, and FIGS. 14 and 15, we determined how best to evaluate the quality of an improved multiplex assay standard curve. We determined that a good standard curve must have an $R^2$ value of >0.98 and that the limit of detection for the PCR reaction should be used as another means of assessment. As discussed earlier, the limit of detection for the PCR reaction is already well documented for qualitative DNA analysis at around 35 pg of total input DNA which corresponds to an average CEFD peak height RFU of 150 (20, 21). To use this value for assessing the quality of a standard curve, the RFU value of 150 is plugged into the standard curve. The picogram amount plus thirty percent (the upper bound picogram amount if the percent CV equals 30% at an RFU of 150 should be calculated by the standard curve as an input DNA of less than 35 pg. The limit of detection (LOD) for the CEFD device defaults at 50 RFU. If a value of 50 RFU is entered into a standard curve, the picogram amount given should also correspond to the amount of DNA within a "blank" sample, since 50 RFU is the default LOD for a CEFD device. Using these assessments, the best standard curve data generated in FIG. 7 would be the standard curves generated from the 2- and 3-second electrokinetic injection times for that CEFD device.

Figure 8:
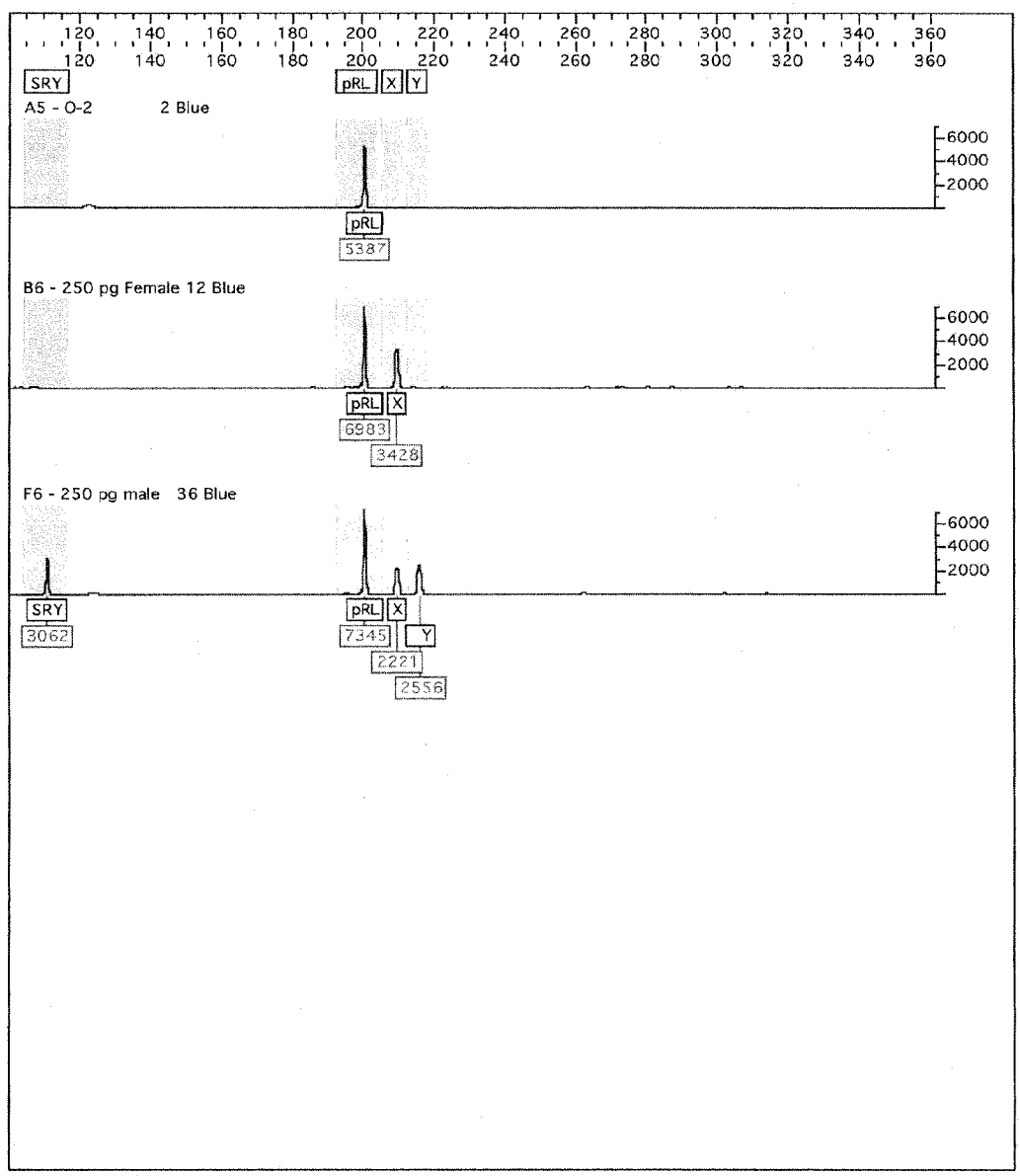
FIG. 8. Example Electropherogram of the four amplicons produced by the improved multiplex assay in the NIST SRM 2372 Standard A male, the NIST SRM 2373 Standard B female, and a blank sample. A Genotyper® 2.5.2 macro was built that would correctly call and label each amplicon in the improved multiplex assay. The data shown from top to bottom is a blank sample consisting of sterile deionized $H_2O$, the NIST SRM 2372 Standard B at a concentration of 250 pg/μL, and the NIST SRM 2372 Standard A at a concentration of 250 pg/μL.

With the ability to evaluate the quality of an improved multiplex assay standard curve, we began to examine the specificity and sensitivity of the improved multiplex assay based upon the appearance of the four possible amplicons in the assay (see FIG. 8). When amplicons were apparent, the peak height RFU for the relevant amplicons were compared to the female Amelogenin X amplicon-derived standard curve (to determine total human DNA quantity in a sample) or the male SRY amplicon-derived standard curve (to determine male-only DNA quantity in a sample) (standard curves are presented in FIGS. 5a and 5b). The original assay utilized only one primer set to evaluate the diploid Amelogenin amplicons (X and Y). We wanted to determine the effect of a multiplex of primer sets on the ability to analyze the peak height RFU of each amplicon. To do this, we amplified 250 pg of the NIST SRM 2372 Standard B female, the NIST SRM 2372 Standard A male, and a blank (sterile deionized $H_2O$). The improved multiplex assay amplifies differing amplicons depending upon the gender of the amplified sample (FIG. 8). In all cases, the internal positive control (IPC) template DNA (pRL null vector) was added to each sample. Table 6A presents the peak height RFU data gathered for the male, female, and blank DNA samples using each possible primer singleplex, primer duplex, or primer triplex (improved multiplex assay) as indicated. Table 6B presents the average singleplex, duplex, and triplex RFU values obtained for each amplicon except the IPC. The CV column of Table 6B indicates that all peak height variation among each reaction varied no more than 16.97% for any amplicon, no matter which reaction was carried out.

TABLE 6A

Peak height RFU data

| Amplicons | Relative Flourescence Units in Height | | | |
|---|---|---|---|---|
| | SRY | pRL | X | Y |
| NIST SRM 2372 B (250 pg) | | | | |
| pRL | ø | 5368 | ø | ø |
| Amelogenin | ø | ø | 5241 | ø |
| SRY | ø | ø | ø | ø |
| SRY + pRL | ø | 7377 | ø | ø |
| pRL + Amelogenin | ø | 6960 | 4683 | ø |
| SRY + Amelogenin | ø | ø | 5535 | ø |
| Tri-Plex | ø | 8000 | 4366 | ø |
| NIST SRM 2372 A (250 pg) | | | | |
| pRL | ø | 5031 | ø | ø |
| Amelogenin | ø | ø | 2346 | 2860 |
| SRY | 3347 | ø | ø | ø |
| SRY + pRL | 2863 | 7491 | ø | ø |
| pRL + Amelogenin | ø | 7484 | 2947 | 1553 |
| SRY + Amelogenin | 4555 | ø | 2118 | 2540 |
| Tri-Plex | 4321 | 7368 | 2278 | 2697 |
| Water | | | | |
| pRL | ø | 5769 | ø | ø |
| Amelogenin | ø | ø | ø | ø |
| SRY | ø | ø | ø | ø |
| SRY + pRL | ø | 6820 | ø | ø |
| pRL + Amelogenin | ø | 7670 | ø | ø |
| SRY + Amelogenin | ø | ø | ø | ø |
| Tri-Plex | ø | 7505 | ø | ø |

TABLE 6B

Average singleplex, duplex, and triplex RFU values

| | | Relative Fluorescence Units | | | | | |
|---|---|---|---|---|---|---|---|
| Sample | Amplicon | Singleplex RFU | Duplex Avg. RFU | Triplex RFU | μ | σ | CV |
| NIST A | Amelogenin X | 5241 | 5109 | 4366 | 4905 | 471.72 | 9.62% |
| NIST B | Amelogenin X | 2346 | 2533 | 2278 | 2386 | 132.05 | 5.54% |
| | Amelogenin Y | 2860 | 2047 | 2697 | 2535 | 430.12 | 16.97% |
| | Amelogenin X + Y | 5206 | 4580 | 4975 | 4920 | 316.56 | 6.43% |
| | SRY | 3347 | 3709 | 4321 | 3792 | 492.32 | 12.98% |

Figure 9:
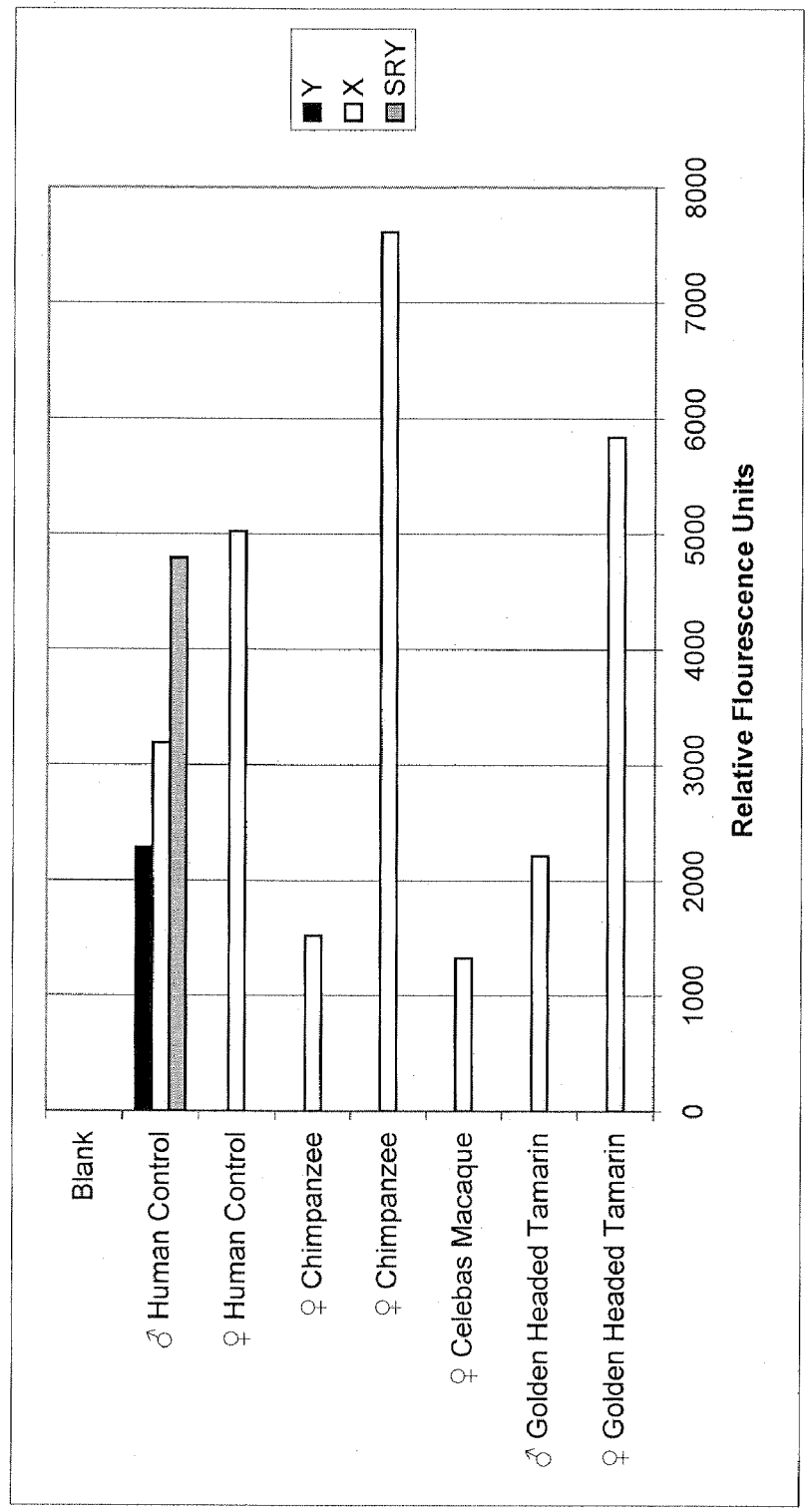
FIG. 9. Specificity of the Improved Multiplex Assay on a panel of primate blood samples
Five non-human primate blood samples were quantified using the improved multiplex assay. The Amelogenin X amplicon was produced in all primate samples. The single male non-human primate sample did not exhibit production of the Amelogenin Y or the SRY amplicons.

The non-human primate specificity of the Amelogenin primer set (17) and the non-human primate specificity of the original assay (Example 1) and (1) has been previously demonstrated. The SRY primer set used in the improved multiplex assay amplifies a region on the SRY gene that has demonstrated high levels of human-specificity when used in other PCR reactions (22). The human-specificity of the improved multiplex assay as compared to three types of non-human primates is presented in FIG. 9. The Amelogenin X amplicon is produced with varying efficiencies among the five non-human primates tested. The male non-human primate sample did not exhibit Amelogenin Y amplicon production, nor did it exhibit SRY amplicon production.

Figure 10A:
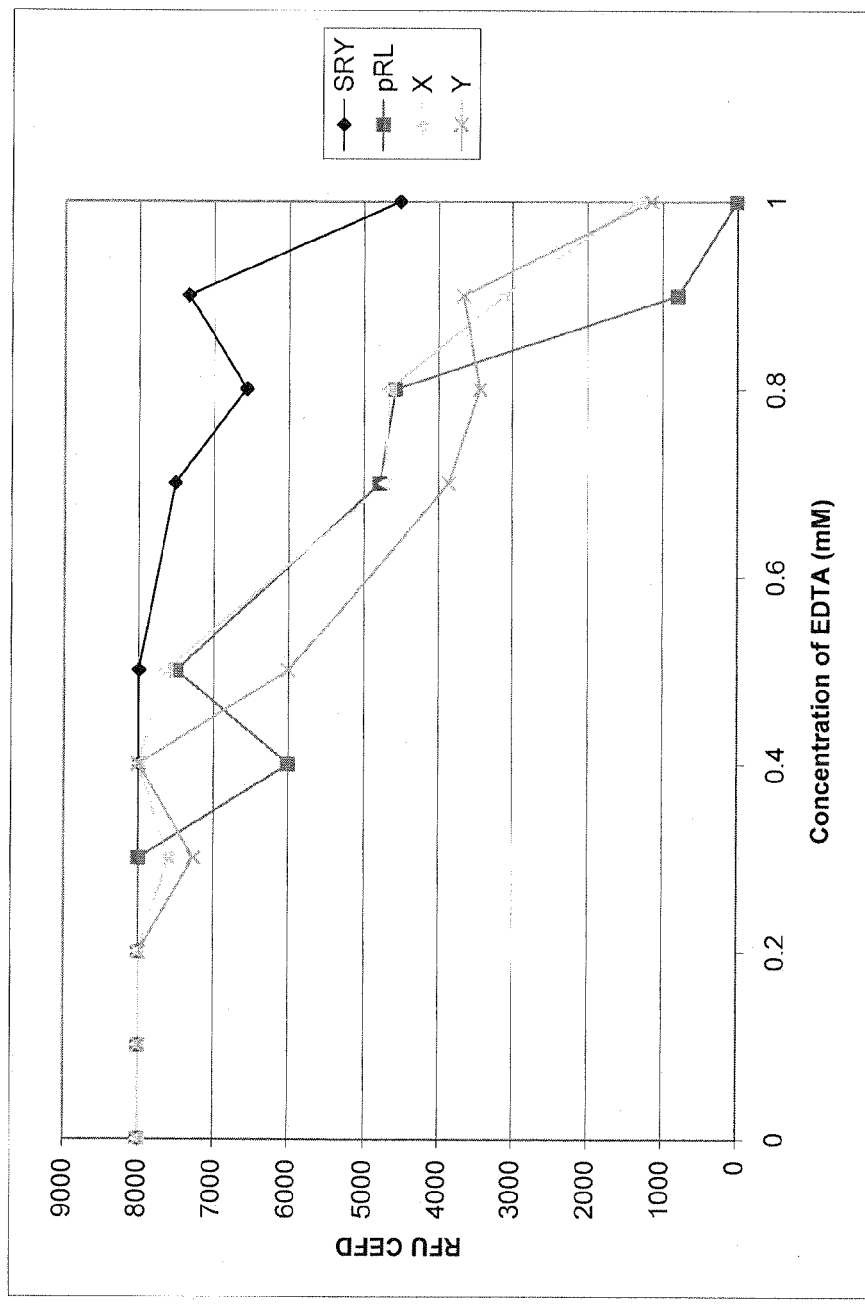
FIG. 10A-B. The Effect of EDTA Concentration on the Improved Multiplex Assay. A, the amplicon peak-height RFU intensities for each of the four amplicons of the improved multiplex assay post-amplification with increasing mM amounts of EDTA were graphed; B, the ratio of peak-height RFU intensities of all four amplicons to the peak-height intensity of the pRL amplicon was graphed with increasing mM amounts of EDTA. The pRL ratio to itself is, thereby, a constant 1.0. The ratio of Amelogenin Y intensity to pRL intensity is less than one between 0.5 and 0.8 mM EDTA concentration, but after 0.8 mM EDTA concentration, all amplicons are of greater intensity then pRL, indicating that pRL is the first amplicon to completely "drop out" when a chemical inhibitor is present in a DNA sample.
Figure 10B:
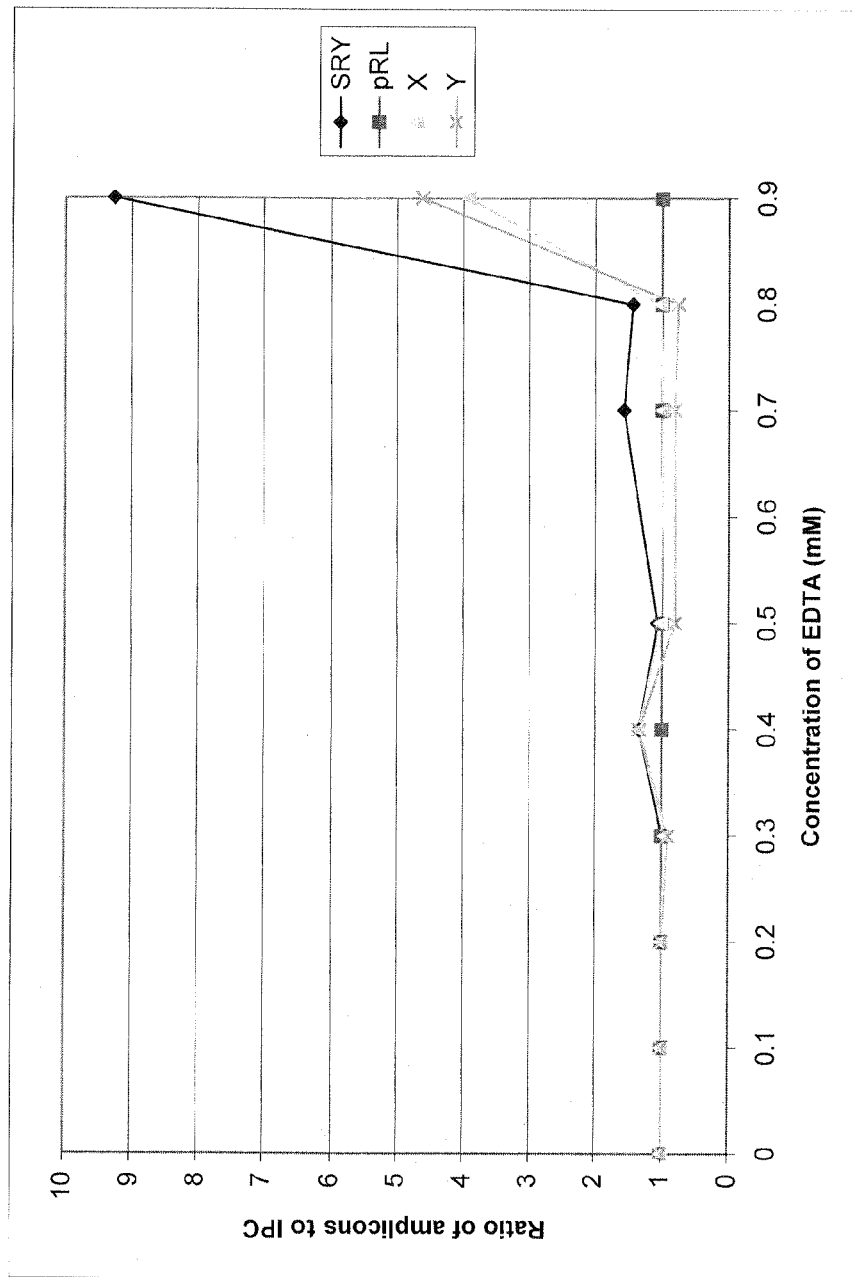

The original assay could not detect the presence of PCR inhibitors. With the addition of the IPC (the pRL plasmid and its corresponding primer set) the improved multiplex assay can very sensitively indicate inhibition with many known inhibitors of PCR (18). FIG. 10a demonstrates the decreasing amounts of peak-height RFU obtained in a male DNA sample treated with increasing amounts of EDTA, a known PCR amplification inhibitor. In FIG. 10b the ratio of the Amelogenin X, Amelogenin Y, and SRY amplicon peak height RFU to the peak height RFU of the IPC is shown. At a final concentration of 0.8 mM EDTA in the PCR reaction, the IPC begins to exhibit much less peak height RFU in relation to the other amplicons. At the 0.9 mM EDTA final concentration, the IPC has vanished. The IPC of the improved multiplex assay appears to be more sensitive to inhibition than the other amplicons, which would allow inhibition to be detected by the IPC in this assay before the effects were as apparent in the other amplicons.

Figure 11A:
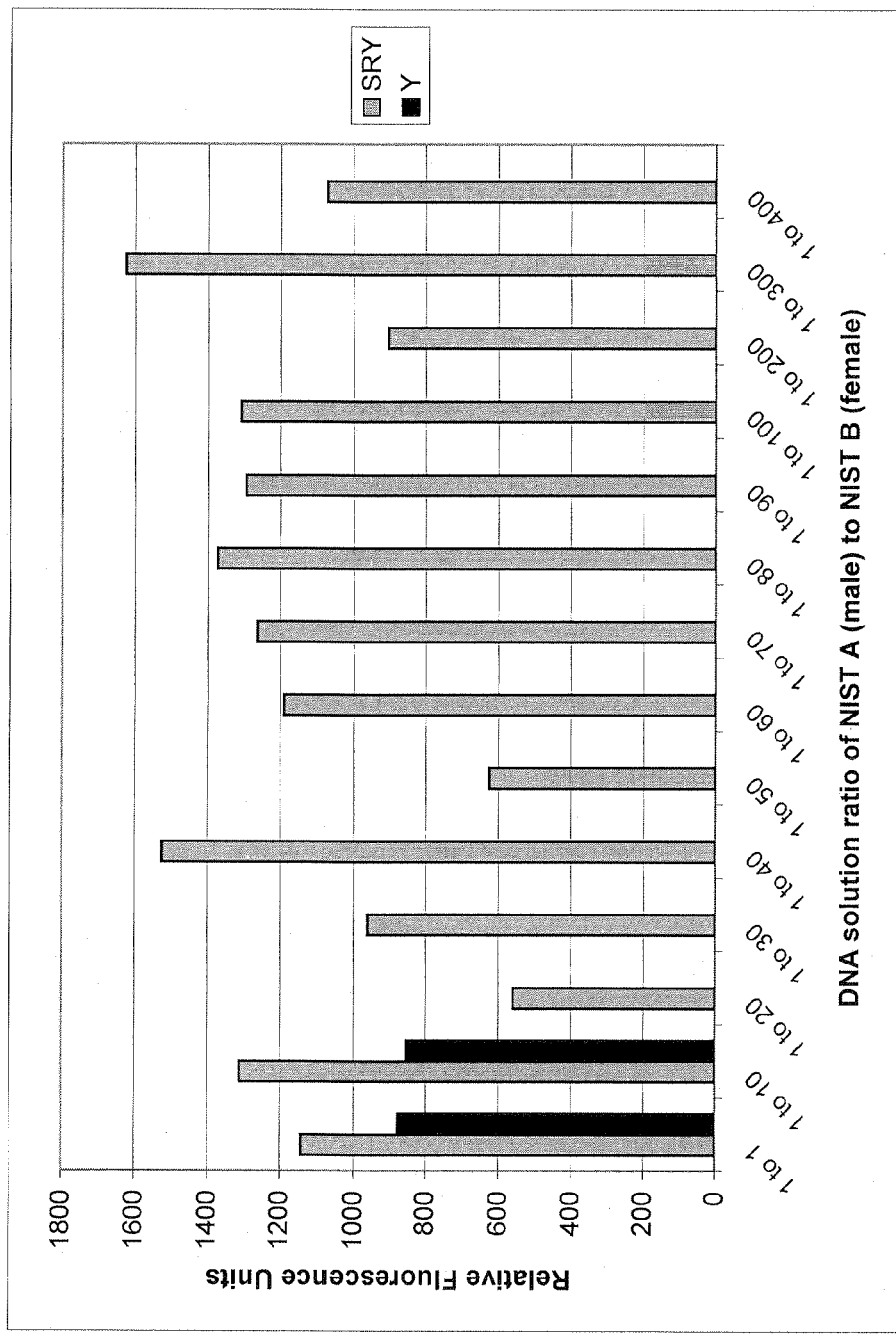
FIG. 11A-B. Sensitivity to detect Male-only DNA in a Preponderance of Female DNA. A, the RFU peak-height intensities of the Amelogenin Y and SRY amplicons were observed in DNA to DNA samples in which the male DNA concentration stayed at a constant 125 pg/μL and the female DNA concentration increased. The Amelogenin Y amplicon "drops out" after a 1 in 10 ratio of male to female DNA. The SRY amplicon does not appear to drop out even when 400 times more female DNA is present in the sample. B, the RFU peak-height intensities of the Amelogenin Y and SRY amplicons were observed in whole male blood to whole female blood ratios as indicated and then dried onto FTA paper. A single hole punch (1.5 mm in radius) of the dried mixture was then DNA extracted and analyzed with the improved multiplex assay. The male blood concentration was not constant in these ratios. The Amelogenin Y amplicon "drops out" after a 1 in 20 ratio of male to female DNA. The SRY amplicon "drops out" when 100 times more female blood was mixed with the male blood.
Figure 11B:
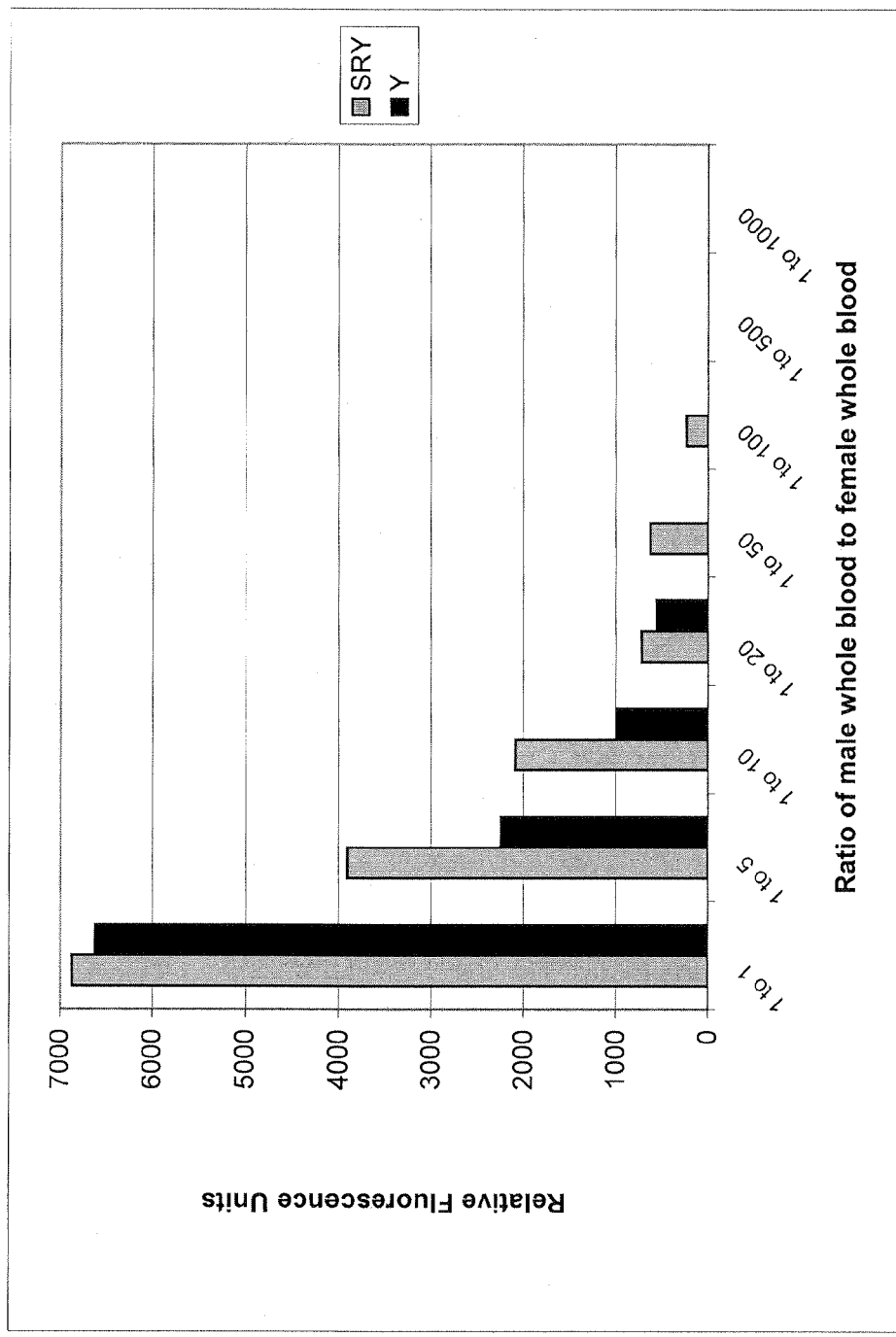

The addition of the SRY amplicon to the multiplex assay allowed for an increase in the ability of this assay to detect the presence of male DNA far beyond the ability of the original assay. Two studies were done to determine the ability of the SRY amplicon and the Amelogenin Y amplicon to detect male DNA in a preponderance of female DNA. FIG. 11a shows the results obtained when exact ratios of the NIST SRM 2372 Standard A male DNA was mixed with increasing amounts of NIST SRM 2372 Standard B female DNA. Each solution was created so that the concentration of the male DNA was a constant 125 pg/μL while admixed female DNA increased at the ratios to the male DNA as shown. In these pure DNA liquid mixtures, the Amelogenin Y amplicon was not able to be detected in the 1:20 ratio or greater. Note that a 1:20 ratio of male to female DNA is a ratio of 1:41 for the Amelogenin Y amplicons to the Amelogenin X amplicons and a ratio of 1 to nothing for the SRY amplicons. In FIG. 11b the same experiment was carried out, but the mixtures were created by mixing ratios of male and female whole human blood, drying this blood, and then extracting the DNA from a consistent sample size of the blood mixtures. In this experiment, the Amelogenin Y amplicon was not able to be detected in the 1:50 ratio or greater. This experiment indicates the increased sensitivity of the SRY amplicon to detect male DNA in mixed samples.

But how do these ratios translate into the ability to successfully profile the Y chromosomal haplotype using the Yfiler™ PCR Amplification Kit? Table 7 demonstrates the YSTR profiling results obtained using the improved multiplex assay's quantification estimate of the male-only DNA content of these mixed samples to target the amount of input DNA (1000 pg) for successful YSTR profiling results according to the manufacturer (23). The average peak height RFU observed for the six minimal European haplotypes reflect the RFU values that would be expected from these DNA samples post-amplification if the estimated input DNA value was indeed accurate.

TABLE 7

Dilution scheme for Yfiler profiling based on quantification values estimated by IMA for 12 samples

| Sample | IMA Estimate of Male DNA in 1 uL | Dilution Recipe in TE | | | pg of DNA in 10 uL | Average RFU of the seven European Minimal Haplotype from Y Filer profiling |
|---|---|---|---|---|---|---|
| 1 to 1 (whole blood) | 1850 | 1 | in | 17 | 1028 | 5073 |
| 5 to 1 (whole blood) | 337 | 4 | in | 9 | 1037 | 4981 |
| 10 to 1 (whole blood) | 179 | 12 | in | 9 | 1023 | 5611 |
| 20 to 1 (whole blood) | 61 | | | | 610 | 4139 |
| 50 to 1 (whole blood) | 53 | | | | 530 | 3483 |
| 100 to 1 (whole blood) | 20 | | | | 200 | 1081 |
| 500 to 1 (whole blood) | 0 | | | | | 193 |
| 1000 to 1 (whole blood) | 0 | | | | | 154 |
| 1 to 1 (DNA solution) | 97 | | | | 970 | 5840 |
| 1 to 50 (DNA solution) | 53 | | | | 530 | 5522 |
| 1 to 100 (DNA solution) | 112 | 10 | in | 1 | 1018 | 1441 |
| 1 to 400 (DNA solution) | 92 | | | | 920 | 2501 |

The ability of the original assay to provide accurate quantification of total human DNA in forensic samples was confirmed (1). In this study, the concentration of DNA in eleven actual casework samples was evaluated by the improved multiplex assay by comparing the quantification values determined by the Amelogenin X and/or Amelogenin Y amplicons to the quantification values determined during Quantifiler® analysis (see Table 8).

TABLE 8

Dilution scheme for Yfiler profiling based on quantification values estimated by IMA for 11 actual cases

| Sample Number | IMA Estimate of Total Human DNA | Quantifiler Estimate of Total Human DNA | Mean (μ) Estimate of Total Human DNA | Dilution Recipe in TE | | | pg of DNA in 10 uL | Identifiler EP | Most Accurate Estimate |
|---|---|---|---|---|---|---|---|---|---|
| 1 | 3725 | 4409 | 4067 | 1 | in | 39 | 1017 | over-amplified | Quantifiler |
| 2 | 451 | 1103 | 777 | 2 | in | 13 | 1036 | over-amplified | Quantifiler |
| 3 | 3650 | 2616 | 3133 | 1 | in | 30 | 1011 | slightly over-amplified | IMA |
| 4 | 6 | 1396 | 701 | 2 | in | 12 | 1001 | under-amplified | IMA |
| 5 | 531 | 606 | 568.5 | 2 | in | 9 | 1034 | slightly over-amplified | Quantifiler |
| 6 | 13075 | 10400 | 11737.5 | 1 | in | 116 | 1003 | over-amplified | IMA |

TABLE 8-continued

Dilution scheme for Yfiler profiling based on quantification values estimated by IMA for 11 actual cases

| Sample Number | IMA Estimate of Total Human DNA | Quantifiler Estimate of Total Human DNA | Mean (μ) Estimate of Total Human DNA | Dilution Recipe in TE | | | pg of DNA in 10 uL | Identifiler EP | Most Accurate Estimate |
|---|---|---|---|---|---|---|---|---|---|
| 7 | 80 | 734 | 407 | 4 | in | 12 | 1018 | under-amplified | IMA |
| 8 | 1425 | 864 | 1144.5 | 2 | in | 20 | 1040 | over-amplified | IMA |
| 9 | 990 | 1046 | 1018 | 1 | in | 9 | 1018 | over-amplified | Quantifiler |
| 10 | 750 | 757 | 753.5 | 2 | in | 13 | 1005 | under-amplified | IMA |
| 11 | 976 | 1041 | 1008.5 | 1 | in | 9 | 1009 | slightly over-amplified | Quantifiler |

In order to make this comparison, the total human DNA concentration quantification results for both methods were averaged together. This average quantification value was used to calculate the amount of DNA sample to add to an Identifiler™ (Applied Biosystems, Foster City, Calif.) amplification to target the addition of 1 ng of total human DNA in 10 μL according to recommendations from the supplier (24). According to the kit supplier, an Identifiler amplification targeting the addition of 0.5 to 1.25 ng/μL would yield DNA profiling results with peak heights of between 1000 to 3000 RFU. The rationale was that if the higher quantification estimate was more valid than the lower quantification estimate between the two estimates, then the resulting Identifiler™ profiling results would appear to be over-amplified (peaks above 3000 RFU). And, conversely, if the lower quantification estimate was more valid than the higher quantification estimate between the two estimates, then the resulting Identifiler™ profiling results would appear to be under-amplified (peaks below 1000 RFU). The dilution scheme and best estimate results obtained from the Identifiler™ profiling of the average of the total human DNA quantification results from the improved multiplex assay and Quantifiler® are presented in Table 8. Six out of eleven times (55%), the improved multiplex estimate appears to provide the better estimate of successful DNA profiling. The ability of the improved multiplex assay to provide accurate quantitation of male-only DNA in forensic samples by use of the results from the SRY amplicon was then assessed. The concentration of male-only DNA in eight of the actual casework samples presented in Table 8 was further evaluated by comparing the quantification values determined by the SRY amplicon of the improved multiplex assay to the quantification values determined during Quantifiler® Y analysis (see Table 9).

In order to make this comparison, the male-only DNA quantification results for both methods were averaged together. This average quantification value was used to calculate the amount of DNA sample to add to a Yfiler™ (Applied Biosystems, Foster City, Calif.) amplification to target the additional of 1 ng of total human DNA in 10 μL according to recommendations from the supplier (23). According to the supplier, an Yfiler™ amplification targeting the addition of 1 ng/μL would yield DNA profiling results with peak heights of between 1000 to 3000 RFU. The rationale was that if the higher quantification estimate was more valid than the lower quantification estimate between the two estimates, then the resulting Yfiler™ haplotype would appear to be over-amplified (peaks above 3000 RFU). And, conversely, if the lower quantification estimate was more valid than the higher quantification estimate between the two estimates, then the resulting Yfiler™ haplotype would appear to be under-amplified (peaks below 1000 RFU). The dilution scheme and best estimate results obtained from Yfiler™ haplotyping of the average of the male-only DNA quantification results from the improved multiplex assay and Quantifiler® Y are presented in Table 9. Five out of eight times (62%), the improved multiplex assay appears to provide the better estimate for successful YSTR haplotyping.

Theoretically, in a pure male DNA samples, the SRY male-only DNA quantity estimate should be the same as the total human DNA quantity estimate. However, a common stochastic effect of PCR amplification is that smaller amplicons are amplified more frequently than larger amplicons. This effect will cause an elevation of the peak height RFU estimation from a smaller amplicon post-amplification than the peak height RFU estimation from a larger amplicon post-amplification. This disparity probably occurs at a ratio similar to the

TABLE 9

Dilution scheme for Yfiler profiling based on average quantification values estimated by IMA and Quantifiler for 8 actual casework samples

Figure 12A:
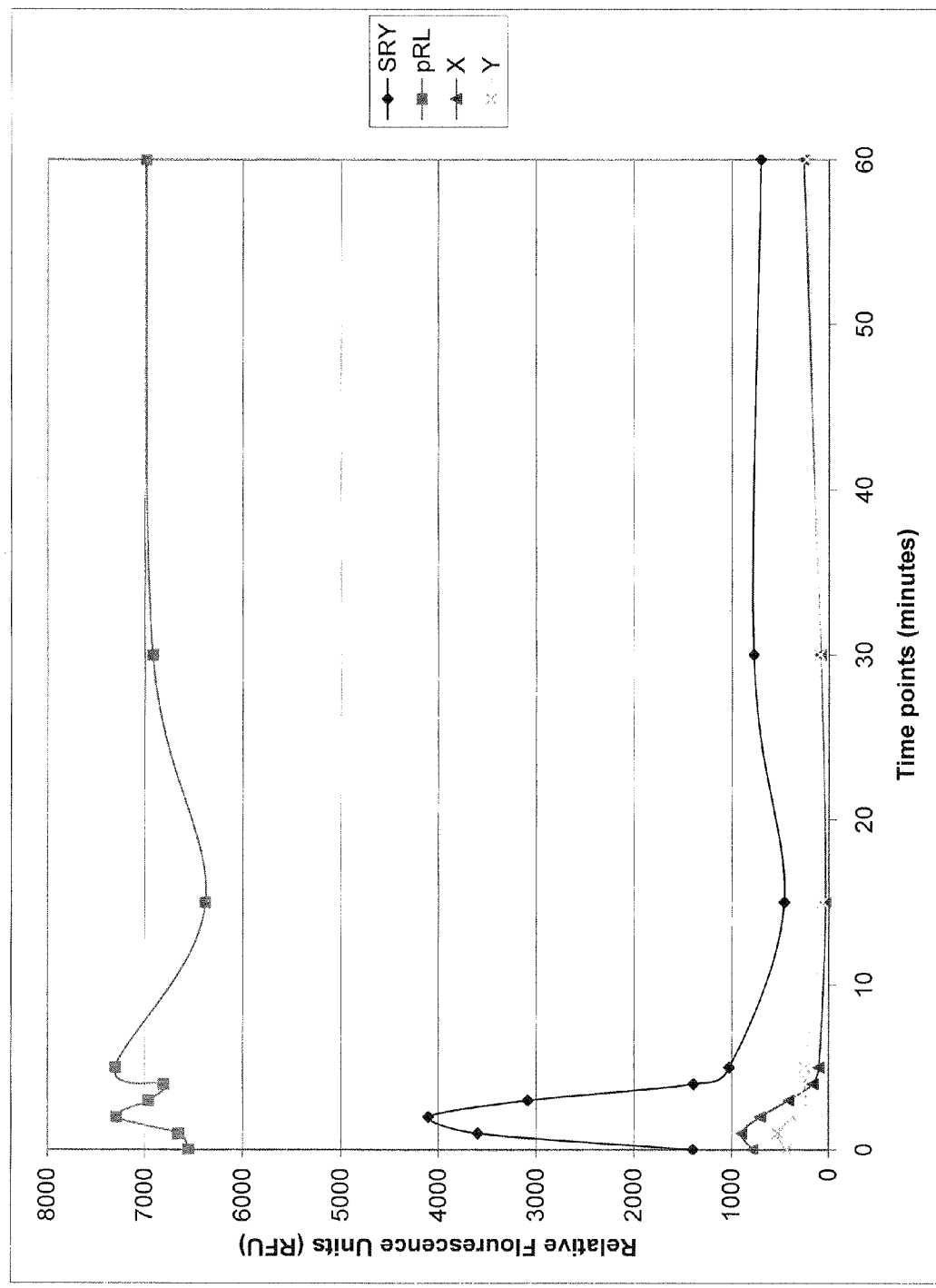
FIG. 12A-B. The Effect of a DNA Degradation Timecourse upon the Four Amplification Products of the Improved Multiplex Assay. A, the amplicon peak-height RFU intensities were graphed for each of the four amplicons of the improved multiplex were gathered post-amplification from a DNase I digestion of a pure male DNA sample subjected to increasing time periods of digestion. B, the ratio of the peak-height RFU intensity of the SRY amplicon at each time-period of digestion to the peak-height intensity of the sum of the Amelogenin X and Amelogenin Y amplicons at each time period of digestion was graphed. The time zero ratio is between 1 and 1.5. The ratio of these amplicons rises to above 3.0 between the one and five-minute time periods of digestion and between the five and thirty-minute time periods of digestion. At these time periods the improved multiplex assay is showing that the pure male sample DNA fragments are less than 200 basepairs in length but more than 100 base-pairs in length.
Figure 12B:
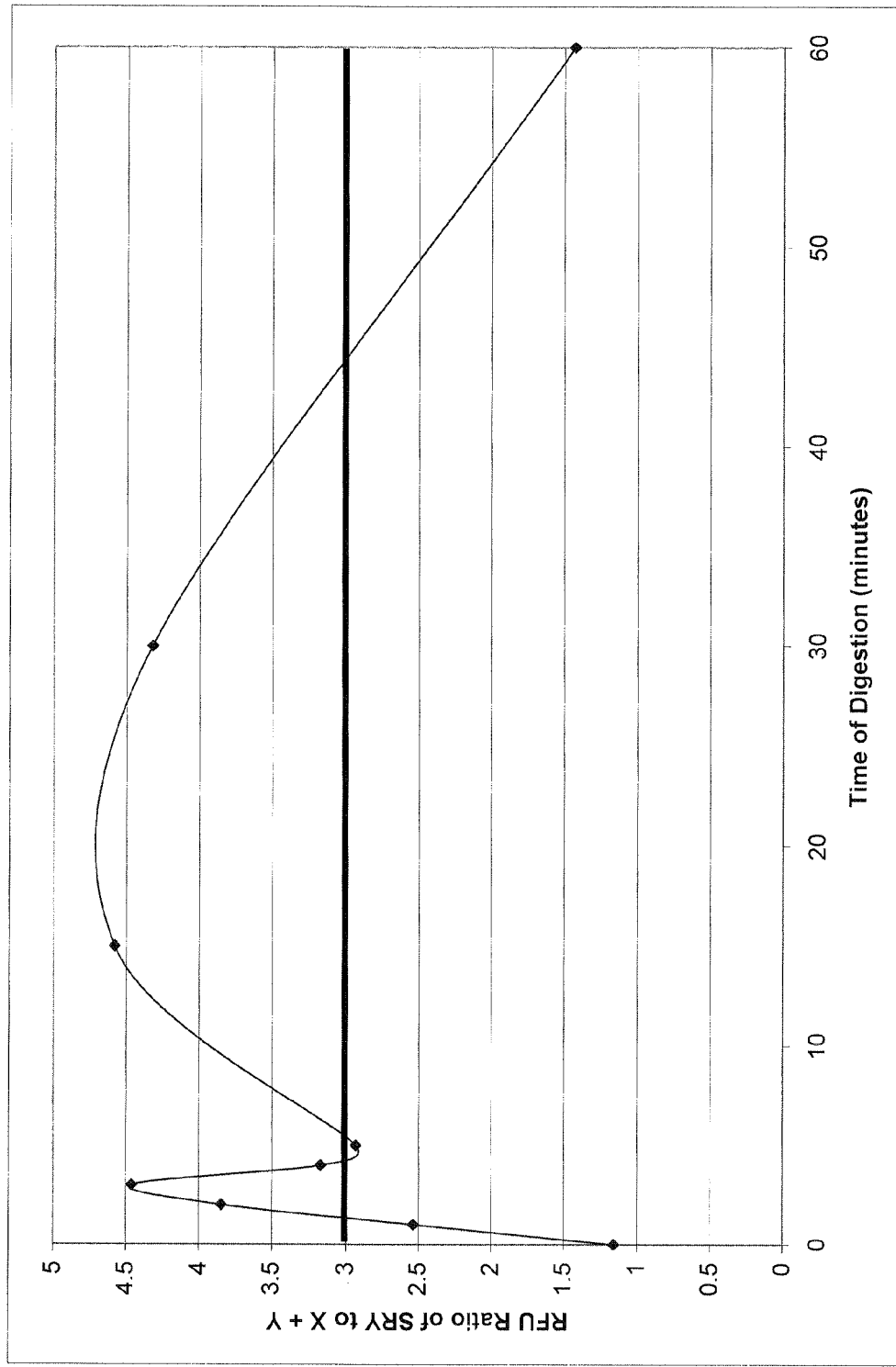

| Sample Number | IMA Estimate of Male-Only DNA | Quantifiler Y Estimate of Male-Only DNA | Mean (μ) Estimate of Male-Only DNA | Dilution Recipe in TE | | | pg of DNA in 10 uL | Identifiler EP | Most Accurate Estimate |
|---|---|---|---|---|---|---|---|---|---|
| 1 | 4225 | 2936 | 3581 | 1 | in | 34 | 1023 | over-amplified | IMA |
| 2 | 474 | 459 | 467 | 3 | in | 11 | 1000 | over-amplified | IMA |
| 3 | 2025 | 2125 | 2075 | 1 | in | 19 | 1038 | over-amplified | Quantifiler |
| 4 | 66 | 80 | 73 | | | | 730 | slightly under-amplified | IMA |
| 5 | 554 | 935 | 745 | 2 | in | 12 | 1064 | over-amplified | Quantifiler |
| 6 | 462 | 912 | 687 | 2 | in | 11 | 1057 | over-amplified | Quantifiler |
| 7 | 613 | 181 | 397 | 3 | in | 8 | 1083 | over-amplified | IMA |
| 8 | 602 | 504 | 553 | 2 | in | 9 | 1005 | over-amplified | IMA | allele peak height imbalance seen between diploid alleles amplified by one primer set. Normal peak height imbalance can easily have an imbalance ratio of 60% to 40% or, in other words, a larger peak to smaller peak ratio of 1.5 (25). If a DNA sample is amplified at specific time points while it is undergoing DNA degradation, amplicons will be seen to arise from smaller pieces of template DNA more frequently during a time period of DNase I digestion than amplicons arising from larger-sized template DNA. In partially degraded DNA samples, this disparity between the fluorescence of a smaller amplicon post-amplification and the fluorescence of a larger amplicon post-amplification will be seen during the specific time periods when larger template DNA would be too degraded to function as templates during amplification, but smaller DNA templates would still be able to function as templates during amplification. With these factors in mind, the addition of the SRY primer set to the improved multiplex assay appears to be able to assess degradation in pure male DNA samples. FIG. 12a demonstrates the decreasing amounts of peak-height RFU obtained in a male DNA sample subjected to DNase I enzymatic digestion over increasing periods of digestion time. The SRY amplicon is smaller than the Amelogenin X amplicon and Amelogenin Y amplicon by approximately 100 basepairs and appears to suffer the effects of DNase I digestion much later than do the other amplicons, as expected. The estimated picograms of male-only DNA derived from comparison of the SRY amplicon to the male-only SRY standard curve can be compared to the estimated picograms of total human DNA derived from the sum of the fluorescence of the Amelogenin X and Amelogenin Y amplicons compared to the total human X standard curve. As stated earlier, in a pure male sample, these estimates should be within a ratio of around 1.5 if stochastic effects are taken into account. But, if the male-only DNA estimate for each time point based on the SRY amplicon is truly within a degraded DNA sample, then the ratio of the male-only DNA estimate (SRY peak height RFU) to the total human DNA estimate (Amelogenin X+Amelogenin Y peak height RFU) should begin to significantly increase. A ratio of 3.00 would represent a ratio of male-only DNA to total human DNA of 75% to 25%. A graph of this ratio over increasing periods of digestion time is presented in FIG. 12b. Note that at time zero of digestion, the ratio of the SRY peak height RFU to the Amelogenin X+Y peak height RFU is between 1.0 and 1.5, as expected. After time zero, each area in the graphed ratio rising above 3.00 represents a time period of digestion in which SRY peak height RFU was 75% or greater than the Amelogenin X+Y peak height RFU. The time points when the graphed ratios rise above 3.00 indicate that the sample had degraded to the point that it contained mostly DNA fragments that were larger than 100 basepairs but shorter than 200 basepairs.

Discussion

The improved assay that we validate in this study fulfills all of the criteria desirable in an ideal quantification method. The improved multiplex assay successfully detects chemical inhibitors of DNA amplification indicating that additional purification of the DNA sample will be needed before successful DNA profiling can be performed. The improved assay is human specific. When the human-specificity of the improved multiplex assay is compared to three types of non-human primates, only the Amelogenin X amplicon is produced with any consequence. The male non-human primate sample did not exhibit Amelogenin Y amplicon production, nor did it exhibit SRY amplicon production. The improved multiplex assay may give false positive results for Amelogenin X in the presence of non-human primate DNA material, but it does not appear that the Amelogenin Y or SRY amplicons will give false male-DNA results for forensic samples. The improved multiplex assay detects "maleness" in a redundant fail-safe way. The SRY amplicon can easily detect 125 pg/µL of male DNA in a sample with up to 400 times more female DNA present in the sample. There appears to be no limit to the ability of the SRY amplicon to present itself in an unlimited quantity of female DNA as long as 125 pg/µL of male DNA resides in the sample. Amelogenin Y provides a redundant indication of maleness down to about a 1:20 ratio of male to female DNA or stain material. In certain population groups, males may exhibit unusually high levels of Y chromosomal mutation that may obliterate the primer binding site for the Amelogenin primer set in this assay (C, I, H). For these males, the improved multiplex assay would still be able to detect the presence of the SRY amplicon as an indicator of maleness. Qualitatively, the presence of male DNA could be detected by either the Amelogenin Y amplicon or the SRY amplicon although these amplicons have varying sensitivities of detection in mixtures. We chose to base our male-only DNA quantification upon the SRY amplicon because of its increased sensitivity as a haploid amplicon with no female counterpart to cause stochastic interference. However, in the presence of an SRY primer-binding mutation the Amelogenin Y amplicon can be quantified by using the Amelogenin X standard curve to estimate the picogram amount of DNA in the single Amelogenin Y amplicon and multiplying this value times two (Y+Y) to estimate the total of male-only DNA in a sample regardless of a pure or mixed sample and regardless of the amount of Amelogenin X amplicon. This method of determining male-only DNA quantity in a sample is just a less sensitive method for determining male-only DNA in mixed samples.

Figure 13:
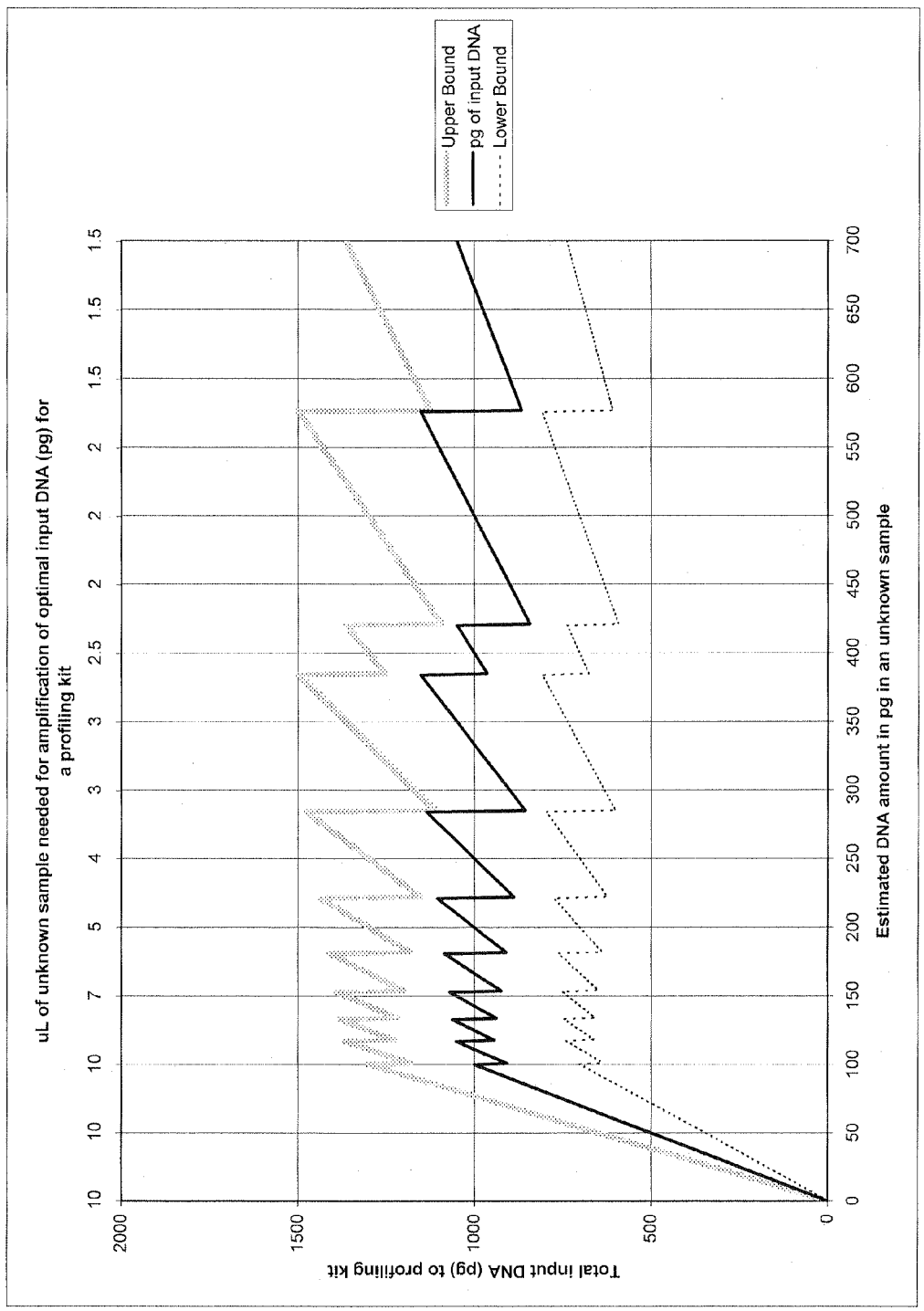
FIG. 13. Graphic Representation of Estimated Concentration of DNA from Any Quantification Method that Exhibits a Percent CV of ±30% versus the Actual Amount of Input DNA Targeted for the Identifiler™ or Yfiler™ DNA Testing Reactions. This is a graphic representation of any DNA quantification method with a CV of 30% to target 1000 pg in 10 µl for profiling with any DNA kit requiring the input of 1000 pg DNA in 10 µl when the DNA testing kit has a successful range of input DNA of between 500 pg to 1500 pg.

The improved multiplex assay is very sensitive in detecting human and male-only DNA in samples. We have determined that the limit of detection for the improved multiplex assay must lie just below an input DNA of 63 pg. In FIG. 13 we graph the amount of DNA estimated within a sample against the amounts of DNA sample at each estimate that would need to be input into an AmpFlSTR® Identifiler™ PCR reaction or an AmpFlSTR® Yfiler™ PCR reaction. The AmpFlSTR® Identifiler™ PCR Amplification Kit manual says that the analyst should target the addition of 0.5 to 1.25 ng in a total volume of 10 µL. This corresponds to the addition of 10 µL of a 50-125 pg/µL DNA sample. The AmpFlSTR® Yfiler™ PCR Amplification Kit manual says that the analyst should target the addition of 1 ng in a total volume of 10 µL. This corresponds to the addition of 10 µL of a 100 pg/µL DNA sample. The AmpFlSTR® MiniFiler™ PCR Amplification Kit manual says that the analyst should target the addition of 0.5-0.75 ng in a total volume of 10 µL (29). This corresponds to the addition of 10 µL of a 50-75 pg/µL DNA sample. As demonstrated by the graph in FIG. 13, if the amount of DNA estimated in the sample was ≦100 pg/µL, then 10 µL of that sample would need to be amplified to target the ideal input DNA for either Identifiler™ or Yfiler™ DNA testing even with a quantification method having a CV of 30% (see upper and lower bound lines in FIG. 13).

Moreover, the sensitivity and performance of the improved multiplex assay is very relevant. Quantification methods are more desirable if they can best predict the success of later DNA profiling of a particular forensic evidence sample by having a dynamic range that overlaps the optimal DNA concentration range of later DNA-profiling procedures. The improved multiplex assay has the same amplification parameters and diploid versus haploid stochastic efficiencies as the commercially available genomic DNA profiling kits. The Amelogenin X and Amelogenin Y amplicons amplify within the size range and stochastic efficiency of the Identifier™ DNA profiling kit. The ratio of Amelogenin X to Amelogenin Y in mixed samples very accurately mirrors the amplification ratios that will be seen between the major and minor, male and female contributors when the mixture is genomically DNA profiled. The SRY amplicon amplifies within the size range and stochastic efficiency of the commercially available male Y-chromosome DNA haplotyping kits such as Y-filer (Applied Biosystems, Foster City, Calif.). The SRY amplicon in the improved multiplex assay is 111 nucleotides in length. The lengths of the haplotypes profiled by Y-STR profiling are 100-300 nucleotides in length. The Quantifiler® Y kit bases its estimation of male-only DNA upon the amplification of an SRY amplicon only 60 nucleotides in length. This shorter SRY amplicon made the Quantifiler® Y assay more sensitive in detecting male DNA in a sample, but later profiling of these samples would not yield successful Yfiler™ haplotyping results (personal communication with an Applied Biosystems representative) The shorter SRY amplicon was a good predictor of male DNA in a sample, but was not a good predictor of successful YSTR testing (30). The Quantifiler® Y Kit is undergoing modification to adjust the SRY primers so that the SRY amplicon is a longer length that approximates the 100-300 nucleotide amplified haplotypes of the Yfiler™ PCR Amplification Kit (30). We believe that the SRY amplicon in our improved multiplex assay is not only a sensitive detector of male DNA in a sample, it is also an accurate predictor of successful YSTR haplotyping (see Tables 7, 8, and 9).

The improved multiplex assay has been determined by our analyses to have a dynamic range of 63 pg to 500 pg detection of input DNA in 1 µL. When coupled with the ability to dilute input DNA the dynamic range becomes unlimited (see Table 10). Within only four dilutions, a sample containing anywhere from 63 pg/µL DNA to 100,000 pg/µL DNA can be quantified using the improved multiplex assay—every possible DNA quantitation result can be anticipated to fall within one of the dilution schemes in the Table 10. The need for dilution necessitates repeat sample analysis, which can become costly and time consuming, but the improved multiplex assay is extremely low cost, fast, hands-free, and low maintenance. Current DNA profiling technology relies upon a basic PCR amplification followed by CEFD analysis. The improved multiplex assay relies upon these same two technologies. For this reason, the assay is extremely cheap to initiate at a DNA profiling laboratory and additional space is not required. No new instrumentation is needed. Analysts do not have to spend time training for the proper usage of new equipment and learning new technology. Validation is very straight-forward. Because virtually no new reagents are required for this assay, time and resources are not spent upon quality assurance practices and quality control activities. The original assay amplification cycle has been optimized and shortened. The procedure has been validated in this study using a thermo-stable DNA polymerase that costs approximately thirty cents a reaction. The three primer sets can be ordered online and manufactured for less than sixty cents. This translates into a set of reagents that cost less than one dollar per sample. DNA samples requiring quantification can be amplified in less than an hour and forty-five minutes. Sample analysis takes twenty-one minutes per sample on a ABI Prizm® 310 Genetic Analyzer, but a multicapillary CEFD device or a DNA chip device could dramatically decrease the time involved to perform the improved multiplex assay. The improved multiplex assay is very hands-off. Analysts performing the improved multiplex assay perform tasks that would be easily automated. The generation of standard curves and sample dilutions is completely amenable to automation. Because the improved multiplex assay can both gender-type and quantitate DNA samples containing any male DNA, the improved multiplex assay can serve as a qualitative screening method. This, coupled with automation and a low cost, would potentially allow for a high volume and low cost ability to screen large amounts of evidentiary items such as the burgeoning backlog of sexual assault evidence collection kits and other evidence that some forensic laboratories are currently experiencing.

TABLE 10

Exemplary dilution schemes
Calculated Total Human DNA in pg/uL

| | Null | 1:10 Dilution | 1:100 Dilution | 1:200 Dilution |
|---|---|---|---|---|
| <63 | <63 | Too Dilute | Too Dilute | Too Dilute |
| 63 | 63 | Too Dilute | Too Dilute | Too Dilute |
| 125 | 125 | Too Dilute | Too Dilute | Too Dilute |
| 250 | 250 | Too Dilute | Too Dilute | Too Dilute |
| 500 | 500 | <63 | Too Dilute | Too Dilute |
| 750 | truncated | 75 | Too Dilute | Too Dilute |
| 1,000 | truncated | 100 | Too Dilute | Too Dilute |
| 1,500 | truncated | 150 | Too Dilute | Too Dilute |
| 2,000 | truncated | 200 | Too Dilute | Too Dilute |
| 2,500 | truncated | 250 | Too Dilute | Too Dilute |
| 5,000 | truncated | 500 | <63 | Too Dilute |
| 10,000 | truncated | truncated | 100 | <63 |
| 15,000 | truncated | truncated | 150 | 75 |
| 20,000 | truncated | truncated | 200 | 100 |
| 30,000 | truncated | truncated | 300 | 150 |
| 40,000 | truncated | truncated | 400 | 200 |
| 50,000 | truncated | truncated | 500 | 250 |
| 60,000 | truncated | truncated | truncated | 300 |
| 70,000 | truncated | truncated | truncated | 350 |
| 80,000 | truncated | truncated | truncated | 400 |
| 90,000 | truncated | truncated | truncated | 450 |
| 100,000 | truncated | truncated | truncated | 500 |

Figure 15:
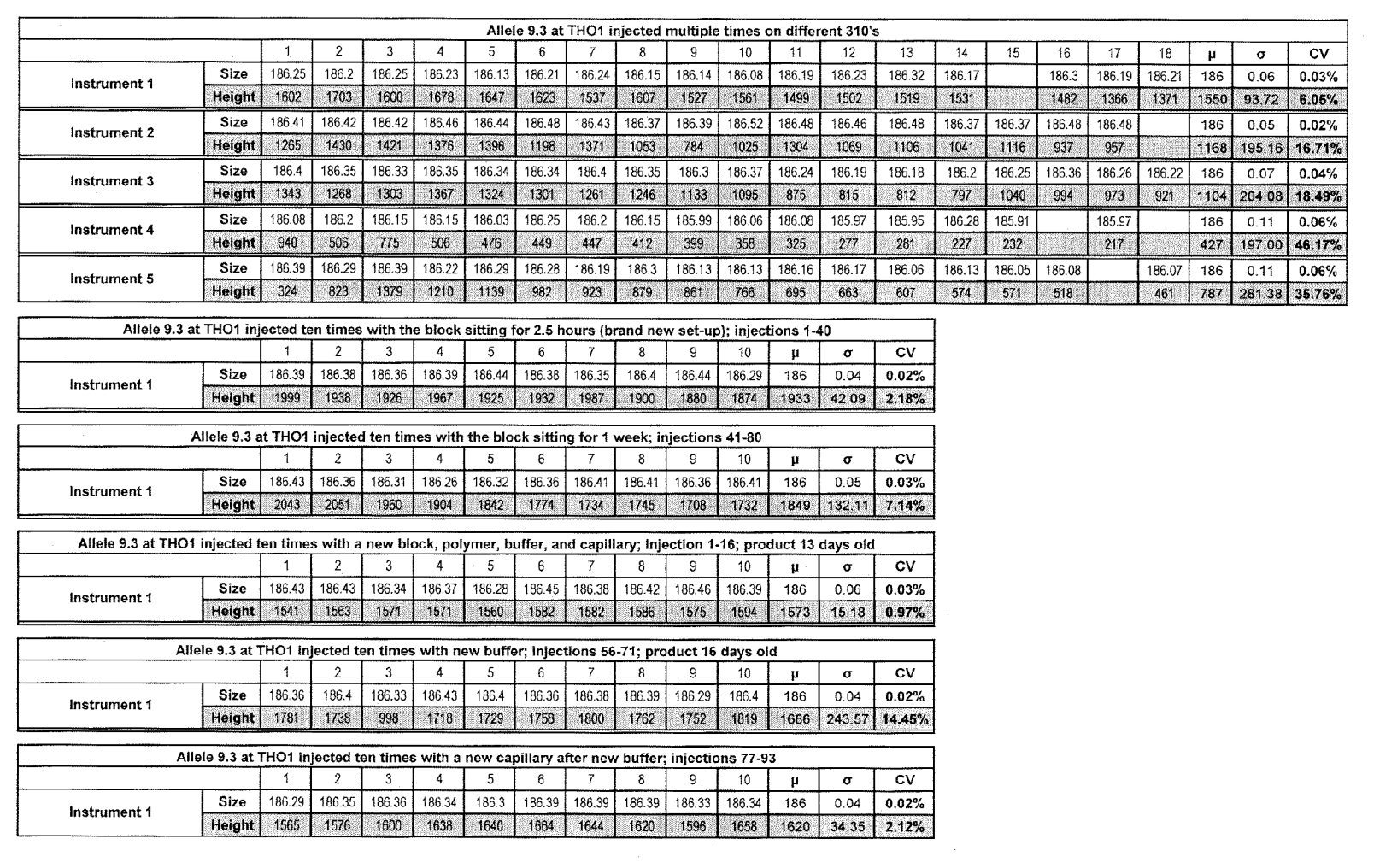

Current research in this laboratory is focused upon the ability of the improved multiplex assay to detect DNA degradation levels in some samples. From FIG. 12b it appears that the improved multiplex assay can detect the effects of degradation. However, because the SRY amplicon is critical in assessing the level of degradation, degradation can only be assessed for the male component of DNA samples. We are intrigued that no other quantitation method provides information diagnosing the level of DNA degradation or average DNA fragment length within a sample save the yield gel. If DNA degradation levels that preclude the success of regular DNA testing procedures can be determined in a DNA sample, then an early decision can be made to use DNA testing procedures that are more successful on degraded samples such as the newly introduced AmpFlSTR® MiniFiler™ PCR Amplification Kit (Applied Biosystems, Foster City, Calif.). Further improvement of the improved multiplex assay may be achieved by addition of a 100 bp amplicon that can estimate total human DNA concentration for the detection of degradation in male, female, and mixed samples. We are also interested in the effect of an undiagnosed high percent CV for detecting peak height RFU among CEFD devices utilized in forensic mixture profiling. We are interested in the effect of high quantitative percent CV values on the accuracy of determining major and minor contributors to mixtures. To the best of our knowledge, the CEFD device was designed for accu rately size-calling DNA fragments (26). Determining the percent CV for a CEFD device's size-calling ability is a routine quality control and instrumental validation activity for laboratories performing DNA profiling with CEFD devices. Determining the percent CV of a CEFD device for accurately quantifying any particular DNA fragment has not, to the best of our knowledge, been adequately addressed by the forensic community, although the quantitative use of CEFD has been published (27, 28). In FIG. 15, the percent CV for any particular CEFD device to detect peak-height fluorescence within a single DNA sample did not appear to be very reproducible for some instruments. The percent CV for peak-height fluorescence ranged from 6.05% to 46.17%. And, as expected, the percent CV for the detection of peak-height fluorescence has no correlation with the percent CV of the same instrument for size-calling ability. In other words, even if a CEFD device has a very low CV for size-calling, it may have a very high CV for detecting peak height RFU and we were quite unaware of this fact until this study.

REFERENCES FOR EXAMPLE 3

1 Allen R W and Fuller V. Quantitation of human genomic DNA through amplification of the amelogenin locus. J. Forensic Sci. 51:76-81 (2006).
2 DNA Advisory Board, Federal Bureau of Investigation. Quality assurance standards for forensic DNA testing laboratories. Washington, D.C.: Federal Bureau of Investigation, 2000. See website located at fbi.gov/hq/lab/fsc/back-issu/july2000/codis2a.htm#Introduction
3 Sifis M E, Both K, Burgoyne L A. A more sensitive method for the quantitation of genomic DNA by Alu amplification. J. Forensic Sci. 47:589-592 (2002).
4 Nicklas J A, Buel E. Development of an Alu based, real-time PCR method for quantitation of human DNA in forensic samples. J. Forensic Sci. 48:936-944 (2003).
5 Alonso A, Marten P, Albarran C, Garcia O. Fernandez de Simon L. Real-time PCR designs to estimate nuclear and mitochondrial DNA copy number in forensic and ancient DNA studies. Forensic Sci. Intl. 139:141-149 (2004).
6 Walker J A, Kilroy G E, Xing J, Shewale J, Sinha S K, Batzer M A. Human DNA quantitation using Alu element based polymerase chain reaction. Anal Biochem. 315:122-128 (2003).
7 Andreasson H, Gyllensten U, Allen M. Real-time PCR quantification of nuclear and mitochondrial DNA in forensic analysis. Biotechniques. 33:402-411 (2002).
8 Nicklas J A, Buel E. Development of an Alu based, QSY7-labeled primer PCR method for quantitation of human DNA in forensic samples. J. Forensic Sci. 48:282-191 (2003).
9 Sherrill C B et al. "Nucleic acid analysis using an expanded genetic alphabet to quench fluorescence" J. Am. Chem. Soc. 126:4550-6 (2004).
10 Quantifler Human® DNA Quantification Kit and Quantifiler® Y Human Male DNA Quantification Kit User's Manual. Applied Biosystems, Foster City, Calif. 2006.
11 Plexor® HY System Protocol available on the website located at promega.com/catalog/catalogproducts.asp?catalog_name=Promega_Products&category_name=Plexor+HY+System
12 Horsman K M et al. Development of a human-specific real-time PCR assay for the simultaneous quantitation of total genomic and male DNA. J. Forensic Sci. 51 (4):758-765 (2006).
13 Costa et al, "The Plexor® HY System Not Solely a Quantitation Technique" Profiles in DNA. 10(2):6-9 (2007).
14 NIST SRM 2372 certificate of analysis available online at the website located at srmors.nist.gov/certificates/2372.pdf?CFID=12275797&CFTOKEN=63a215f7f42727ee86EE05AA-DC86-5331-44B90635C57DEEB1&jsessionid=b4308629b170806a2945
15 Sullivan K M, Mannucci A, Kimpton C P, Gill P. A Rapid and Quantitative DNA Sex Test: Fluorescence-Based PCR Analysis of X-Y Homologous Gene Amelogenin. BioTechniques. 15(4):636-641 (1993).
16 Su H and Lau Y C. Identification of the transcriptional unit, structural organization, and promoter sequence of the human sex-determining region Y (SRY) gene, using a reverse genetic approach. Am. J. Hum. Genet. 52:24-38 (1993).
17 Santos F R, Pandya A, and Tyler-Smith C. Reliability of DNA-based sex tests. Nature Genet. 18:103 (1998).
18 Benson G. "Improved Quantitation of Human DNA using Quantitative Template Amplification Technology" M.S. Thesis submitted to faculty of Oklahoma State University. C2007.
19 Moretti T R, Baumstark A L, Defenbaugh D A, Keys K M, Brown A L, Budowle B. Validation of STR typing by capillary electrophoresis. J. Forensic Sci. 46(3):661-676 (2001).
20 Butler J M, McCord B A. Validation Aspects to Consider in Bringing a New STR Kit On-line. AAFS 2006 Workshop #6. Seattle, Wash. Feb. 20, 2006. Down-loadable from the website located at cstl.nist.gov/biotech/strbase/training.htm
21 Butler J M. Introduction to Low Copy Number (LCN) DNA Testing Issues. MAAFS 2006 LCN Workshop. Richmond, Va. May 3 d, 2006. Available on the web site located at cstl.nist.gov/div831/strbase/pub_pres/LCNintro_MAAFSworkshop_May2006.pdf
22 McKeown B, Strickley J, and Riordan A. Gender assignment by PCR of the SRY gene: An improvement on Amelogenin. Prog. In Forensic Genet. 8:433-435 (1999).
23 AmpFlSTR® YFiler™ PCR Amplification Kit User's Manual. Applied Biosystems, Foster City, Calif. 2006.
24 AmpFlSTR® Identifiler™ PCR Amplification Kit User's Manual. Applied Biosystems, Foster City, Calif. 2001.
25 Clayton, T. M., Whitaker, J. P., Sparkes, R., Gill, P. "Analysis and Interpretation of Mixed Forensic Stains using DNA STR Profiling". Forensic Science International 91:55-70 (1998).
26 Lazaruk, Katherine et al. Genotyping of Forensic Short Tandem Repeat (STR) Systems Based on Sizing Precision in a Capillary Electrophoresis Instrument. PE Applied Biosystems, Foster City, Calif. 1998.
27 Butler, J. M., McCord, B. R., Jung, J. M., Wilson, M. R., Budowle, B., Allen, R. O. Quantitation of PCR products by capillary electrophoresis using laser fluorescence. J. Chromatogr. B 658: 271-280 (1994).
28 Weir, B. S., Triggs, C. M., Starling, L., Stowell, L. I., Walsh, K. A. J., and Buckleton, J. "Interpreting DNA Mixtures." Journal of Forensic Sciences. 42:213-222 (1997).
29 AmpFlSTR® MiniFiler™ PCR Amplification Kit User's Manual. Applied Biosystems, Foster City, Calif. 2007.
30 Padilla M. Quantifiler® Duo: A Multiplexed System for Quantitative and Qualitative Assessment of Total Human and Human Male DNA in Forensic Samples. MAFS 2007 Presentation. Traverse City, Mich. Sep. 27, 2007.

We claim:

1. A method for determining, in a sample, using a single multiplex PCR reaction, each of: a quantity of genomic DNA from a male donor and a quantity of genomic DNA from a female donor, a ratio between said quantity of genomic DNA from said male donor and said quantity of genomic DNA from said female donor, extent of genomic DNA degradation, and presence of PCR inhibitors, comprising the steps of i) creating a reaction mix by combining an aliquot of said sample and DNA encoding a non-human reporter gene;

ii) amplifying said reaction mix in a single multiplex PCR reaction using a plurality of primer sets comprising:

a) a first primer set comprising synthetic oligonucleotide primers directed against human male and female amelogenin genetic loci;

b) a second primer set comprising synthetic oligonucleotide primers directed against a human Y-chromosome specific gene or a human X-chromosome specific gene, or both;
  wherein amplicons produced from said human Y-chromosome specific gene and said human X-chromosome specific gene are shorter than amplicons produced from said human male and female amelogenin genetic loci; and
  c) a third primer set comprising synthetic oligonucleotide primers directed against said non-human reporter gene;
iii) detecting PCR amplicons produced in said step of amplifying; and
iv) making an assessment of:
  a) said quantity of genomic DNA from a male donor and said quantity of genomic DNA from a female donor,
  b) said ratio between said quantity of genomic DNA from said male donor and said quantity of genomic DNA from said female donor,
  c) said extent of genomic DNA degradation, and
  d) said presence of PCR inhibitors in said sample based on quantities of non-human PCR amplicons detected in said detecting step,
wherein said step of making an assessment of said extent of genomic degradation includes a step of
i. calculating a ratio of:
  PCR amplicons produced by amplifying said human Y-chromosome specific gene and said human male amelogenin genetic locus; and
  PCR amplicons produced by amplifying said human X-chromosome specific gene and said human female amelogenin genetic locus.

2. The method of claim 1, wherein said step of making an assessment determines gender of a donor of said genomic DNA based on the presence or absence of amplicons produced by amplification of said human Y-chromosome specific gene and said human X-chromosome specific gene being shorter than amplicons produced by amplification of said human male and female amelogenin loci.

3. The method of claim 1, wherein said Y-chromosome specific gene is Sex-Determining RegionY (SRY).

4. The method of claim 1, wherein said non-human reporter gene is a luciferase gene.

5. The method of claim 1, wherein one of said synthetic oligonucleotide primers in said first primer set, said second primer set and said third primer set includes a detectable label.

6. The method of claim 5, wherein said detectable label is fluorescent.

7. The method of claim 1, wherein said step of detecting amplicons is carried out using capillary electrophoresis.

8. The method of claim 1, wherein said sample is a forensic sample.

9. The method of claim 1, further comprising the step of, if said ratio is between 1 and 1.5, concluding that said genomic DNA in said sample is not degraded.

10. The method of claim 1, wherein said X-chromosome specific gene is hypoxanthine-guanine phosphoribosyl transferase (HGPRT).

11. A method for determining an extent of genomic DNA degradation in a sample, using a single multiplex PCR reaction, comprising the steps of
i) creating a reaction mix comprising said sample;
ii) amplifying said reaction mix in a single multiplex PCR reaction using a plurality of primer sets comprising:
  a) a first primer set comprising synthetic oligonucleotide primers directed against a first genetic locus on a chromosome;
  b) a second primer set comprising synthetic oligonucleotide primers directed against a second genetic locus on said chromosome; wherein amplicons produced from said second genetic locus are shorter than amplicons produced from said first genetic locus; and
iii) detecting PCR amplicons produced in said step of amplifying; and
iv) making an assessment of said extent of genomic DNA degradation by calculating a ratio of:
  PCR amplicons produced by amplifying said first genetic locus; and
  PCR amplicons produced by amplifying said second genetic locus.

12. The method of claim 11, further comprising the step of, if said ratio is between 1 and 1.5, concluding that said genomic DNA in said sample is not degraded.

13. The method of claim 11, further comprising the step of, if said ratio is 3 or greater, concluding that said genomic DNA in said sample is degraded.

14. The method of claim 11, wherein said first genetic locus is a human amelogenin locus.

15. The method of claim 11, wherein said second genetic locus is a human Y-chromosome specific gene or a human X-chromosome specific gene.

16. The method of claim 11, wherein said reaction mix further comprises DNA encoding a reporter gene, and wherein said method further comprises the steps of:
  amplifying said reporter gene using a third primer set comprising synthetic oligonucleotide primers directed against said reporter gene; and,
  determining the presence or absence of PCR inhibitors in said sample based on amplification of said reporter gene.

17. The method of claim 11, wherein said chromosome is the Y chromosome.

18. The method of claim 11, wherein said first genetic locus is SRY and said second genetic locus is amelogenin.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 1
acctcatcct gggcaccctg g                                               21

<210> SEQ ID NO 2
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 2
aggcttgagg ccaaccatca g                                               21

<210> SEQ ID NO 3
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 3
acgaaagcca cacactcaag aat                                             23

<210> SEQ ID NO 4
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 4
ctacagcttt gtccagtggc                                                 20

<210> SEQ ID NO 5
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 5
aaggtggtaa acctgacgtt g                                               21

<210> SEQ ID NO 6
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 6
ttcatcaggt gcatcttctt g                                               21

<210> SEQ ID NO 7
<211> LENGTH: 21
<212> TYPE: DNA

-continued

```
<213> ORGANISM: Artificial
<220> FEATURE:
<223> OTHER INFORMATION: synthetic oligonucleotide primer

<400> SEQUENCE: 7
acctcatcct gggcaccctg g                                                   21

<210> SEQ ID NO 8
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 8
aggcttgagg ccaaccatca g                                                   21

<210> SEQ ID NO 9
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 9
acgaaagcca cacactcaag aat                                                 23

<210> SEQ ID NO 10
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 10
ctacagcttt gtccagtggc                                                     20

<210> SEQ ID NO 11
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 11
aaggtggtaa acctgacgtt g                                                   21

<210> SEQ ID NO 12
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 12
ttcatcaggt gcatcttctt g                                                   21
```